(12) United States Patent
Penninger et al.

(10) Patent No.: US 12,193,943 B2
(45) Date of Patent: Jan. 14, 2025

(54) GUIDES AND INSTRUMENTS FOR IMPROVING ACCURACY OF GLENOID IMPLANT PLACEMENT

(71) Applicant: HOWMEDICA OSTEONICS CORP., Mahwah, NJ (US)

(72) Inventors: Charles L. Penninger, Warsaw, IN (US); Shawn M. Gargac, Fort Wayne, IN (US); Robert Benjamin Rice, Warsaw, IN (US); Anne Marie Schlamb, Leesburg, IN (US); George S. Athwal, London (CA); Robert D. Graham, Austin, TX (US); Marine Godelu, Grenoble (FR)

(73) Assignee: HOWMEDICA OSTEONICS CORP., Mahwah, NJ (US)

( * ) Notice: Subject to any disclaimer, the term of this patent is extended or adjusted under 35 U.S.C. 154(b) by 14 days.

(21) Appl. No.: 18/365,510

(22) Filed: Aug. 4, 2023

(65) Prior Publication Data
US 2024/0041609 A1    Feb. 8, 2024

Related U.S. Application Data

(63) Continuation of application No. 17/248,788, filed on Feb. 8, 2021, now Pat. No. 11,766,336, which is a
(Continued)

(51) Int. Cl.
*A61F 2/46* (2006.01)
*A61B 17/17* (2006.01)
(Continued)

(52) U.S. Cl.
CPC ........ *A61F 2/4081* (2013.01); *A61B 17/1778* (2016.11); *A61F 2/4612* (2013.01);
(Continued)

(58) Field of Classification Search
CPC .................. A61F 2/4612; A61F 2/4081; A61F 2002/4085; A61F 2002/302; A61F 2002/4677; A61B 17/1778
See application file for complete search history.

(56) References Cited

U.S. PATENT DOCUMENTS

| 6,155,812 A | 12/2000 | Smith et al. |
| 6,719,799 B1 | 4/2004 | Kropf |
| (Continued) | | |

FOREIGN PATENT DOCUMENTS

| JP | 3179628 U | 11/2012 |
| WO | 2006106419 A2 | 10/2006 |

OTHER PUBLICATIONS

Non-Final Office Action issued in connection with U.S. Appl. No. 17/451,499, filed Feb. 9, 2024, 7 pages.
(Continued)

*Primary Examiner* — Dinah Baria
(74) *Attorney, Agent, or Firm* — Duane Morris LLP

(57) ABSTRACT

A patient specific shoulder guide is provided that includes a hub and a plurality of peripheral members. Each of the peripheral members has a peripheral member height dimension between the patient specific contact surface and a side of the peripheral member opposite the patient specific contact surface. At least one of the peripheral members is a low profile peripheral member in which the peripheral height dimension is less than the peripheral height dimension of at least one other of the peripheral members or is less than the hub height.

8 Claims, 33 Drawing Sheets

Related U.S. Application Data continuation-in-part of application No. PCT/US2019/046039, filed on Aug. 9, 2019.

(60) Provisional application No. 62/717,404, filed on Aug. 10, 2018.

(51) Int. Cl.
*A61F 2/40* (2006.01)
*A61F 2/30* (2006.01)

(52) U.S. Cl.
CPC . *A61F 2002/302* (2013.01); *A61F 2002/4085* (2013.01); *A61F 2002/4677* (2013.01)

(56) References Cited

U.S. PATENT DOCUMENTS

| | | | |
|---|---|---|---|
| 7,678,150 | B2 | 3/2010 | Tornier et al. |
| 8,608,749 | B2 | 12/2013 | Meridew et al. |
| 8,663,333 | B2 | 3/2014 | Metcalfe et al. |
| 9,326,862 | B2 | 5/2016 | Smith et al. |
| 9,498,344 | B2 | 11/2016 | Hodorek et al. |
| 9,615,840 | B2 | 4/2017 | Iannotti et al. |
| 10,010,431 | B2 | 7/2018 | Eraly et al. |
| 10,433,969 | B2 | 10/2019 | Humphrey |
| 10,537,390 | B2 | 1/2020 | Varadarajan et al. |
| 10,548,737 | B2 | 2/2020 | Hodorek et al. |
| 11,364,127 | B2 | 6/2022 | Deransart et al. |
| 2003/0028253 | A1 | 2/2003 | Stone et al. |
| 2003/0074080 | A1 | 4/2003 | Murray |
| 2004/0199258 | A1 | 10/2004 | Macara |
| 2006/0161167 | A1 | 7/2006 | Myers et al. |
| 2007/0173945 | A1 | 7/2007 | Wiley et al. |
| 2007/0198094 | A1 | 8/2007 | Berelsman et al. |
| 2009/0099662 | A1 | 4/2009 | Splieth et al. |
| 2010/0082035 | A1 | 4/2010 | Keefer |
| 2010/0114326 | A1 | 5/2010 | Winslow et al. |
| 2011/0118846 | A1 | 5/2011 | Katrana et al. |
| 2012/0010711 | A1 | 1/2012 | Antonyshyn et al. |
| 2012/0253467 | A1 | 10/2012 | Frankle |
| 2012/0289965 | A1 | 11/2012 | Gelaude et al. |
| 2012/0290272 | A1 | 11/2012 | Bryan |
| 2012/0296339 | A1 | 11/2012 | Iannotti et al. |
| 2013/0204375 | A1 | 8/2013 | Winslow et al. |
| 2013/0325134 | A1 | 12/2013 | Viscardi et al. |
| 2014/0074246 | A1 | 3/2014 | Huebner et al. |
| 2014/0142578 | A1 | 5/2014 | Hananouchi |
| 2014/0159282 | A1 | 6/2014 | Smith et al. |
| 2014/0236304 | A1 | 8/2014 | Hodorek et al. |
| 2014/0257304 | A1 | 9/2014 | Eash |
| 2015/0190151 | A1 | 7/2015 | Budhabbatti et al. |
| 2015/0250601 | A1 | 9/2015 | Humphrey |
| 2015/0265411 | A1 | 9/2015 | Deransart et al. |
| 2016/0030196 | A1 | 2/2016 | Eraly |
| 2016/0136904 | A1 | 5/2016 | Murai et al. |
| 2016/0192951 | A1 | 7/2016 | Gelaude et al. |
| 2016/0242933 | A1 | 8/2016 | Deransart et al. |
| 2016/0256222 | A1 | 9/2016 | Walch |
| 2017/0007330 | A1 | 1/2017 | Britton et al. |
| 2017/0027702 | A1 | 2/2017 | Goldstein et al. |
| 2017/0056187 | A1 | 3/2017 | Humphrey et al. |
| 2017/0071748 | A1 | 3/2017 | Humphrey |
| 2017/0150978 | A1 | 6/2017 | Iannotti et al. |
| 2017/0340449 | A1 | 11/2017 | Deransart et al. |
| 2018/0036019 | A1 | 2/2018 | Iannotti |
| 2019/0175354 | A1 | 6/2019 | Knox et al. |
| 2020/0289276 | A1 | 9/2020 | Lefebvre et al. |
| 2021/0228277 | A1 | 7/2021 | Chaoui et al. |
| 2021/0228371 | A1 | 7/2021 | Deransart et al. |
| 2021/0228372 | A1 | 7/2021 | Knox et al. |
| 2022/0031475 | A1 | 2/2022 | Deransart et al. |
| 2022/0287850 | A1 | 9/2022 | Daudet |
| 2022/0330957 | A1 | 10/2022 | Neichel et al. |
| 2022/0354658 | A1 | 11/2022 | Knox et al. |

OTHER PUBLICATIONS

Extended European Search Report issued in connection with European Patent Application No. 24162840.3, Jun. 21, 2024, 11 pages.
Non-Final Office Action issued in connection with U.S. Appl. No. 16/910,663, Dec. 15, 2022, 9 pages.
Communication Pursuant to Article 94(3) issued in connection with European Patent Application No. 19759204.1, May 9, 2023, 6 pages.
First Office Action issued in corresponding Japanese Patent Application No. 2021-506973, Jun. 5, 2023, 5 pages.
Non-Final Office Action issued in connection with U.S. Appl. No. 17/643,436, filed May 22, 2024, 13 pages.
Notice of Allowance issued in connection with U.S. Appl. No. 16/648,128, Feb. 16, 2024, 9 pages.
Communication Pursuant to Article 94(3) issued in connection with European Patent Application No. 18746503.4, Oct. 17, 2023, 5 pages.
Non-Final Office Action issued in connection with U.S. Appl. No. 17/359,745, Nov. 26, 2023, 7 pages.
Final Office Action issued in connection with U.S. Appl. No. 16/910,663, Nov. 16, 2023, 9 pages.
Non-Final Office Action issued in connection with U.S. Appl. No. 17/650,722, Nov. 15, 2023, 10 pages.
Notice of Allowance issued in connection with U.S. Appl. No. 17/645,607, Dec. 20, 2023, 11 pages.

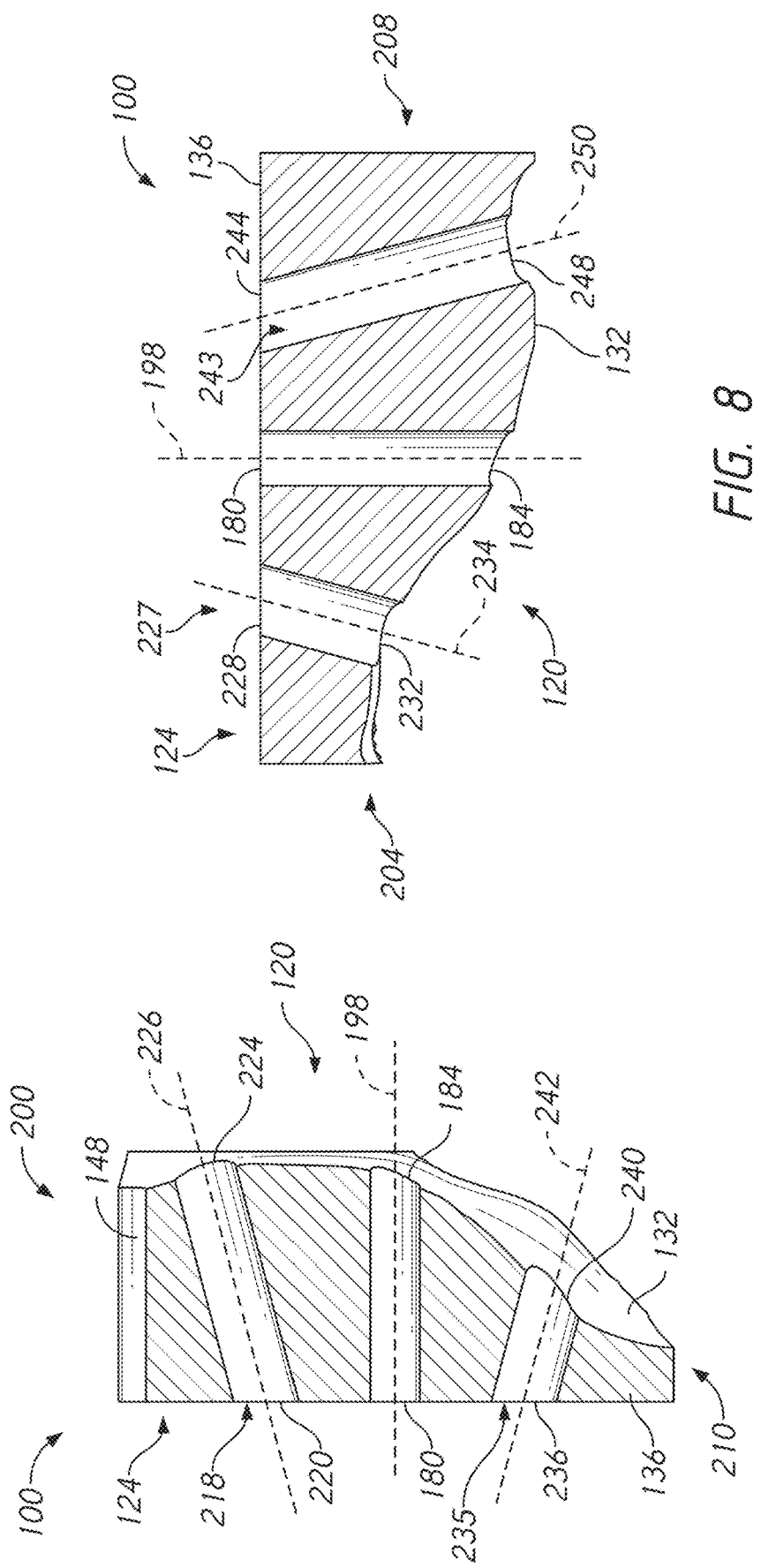

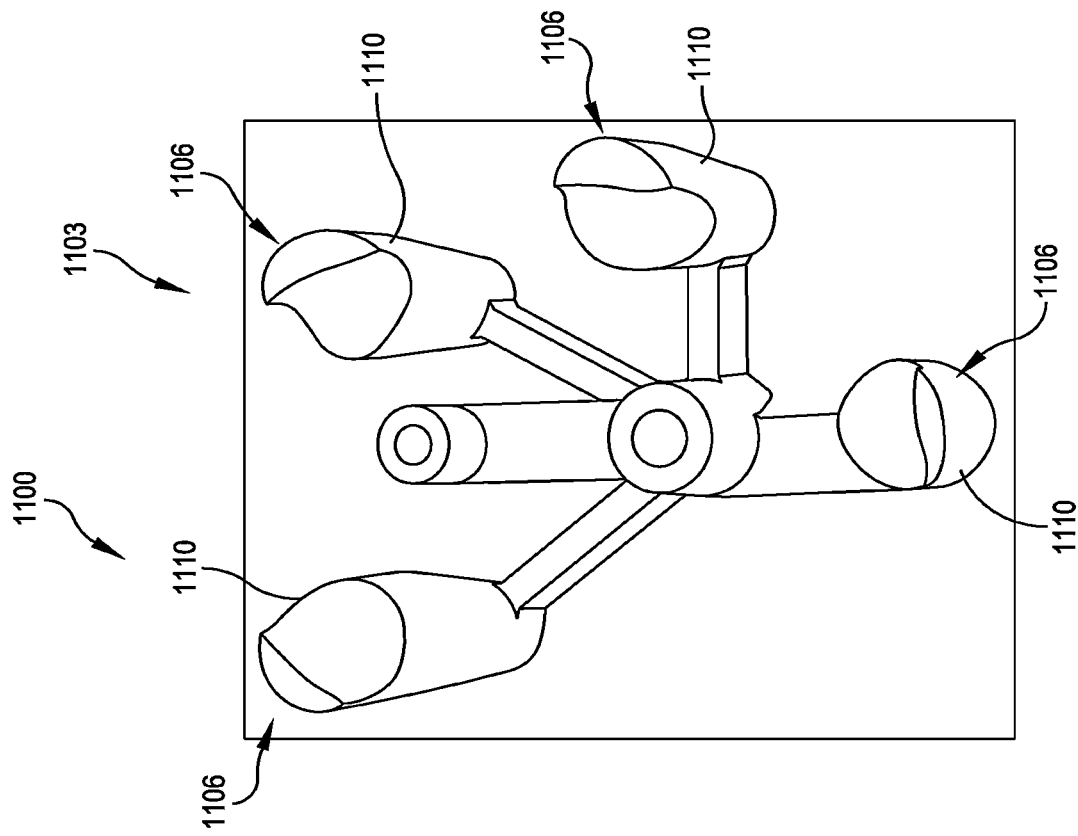
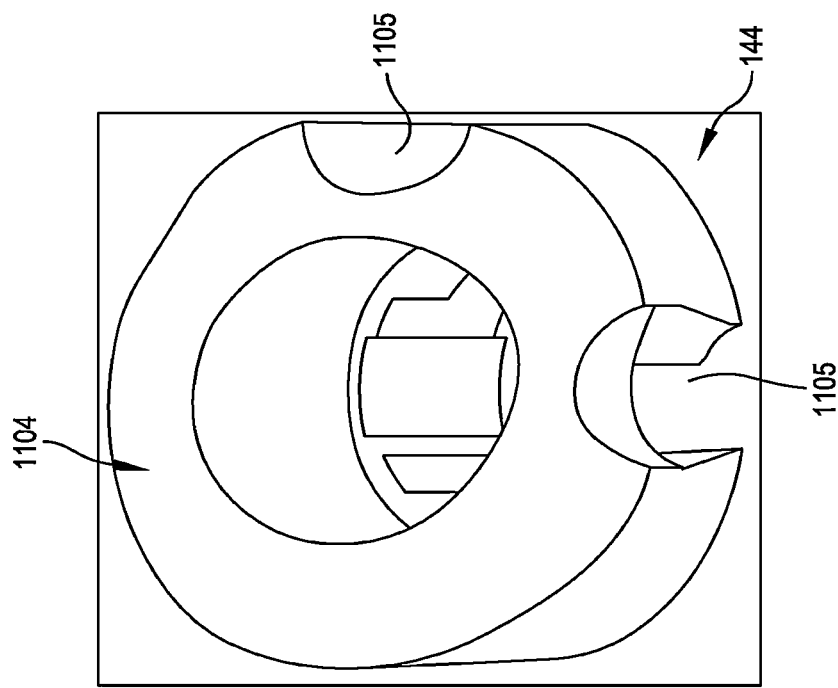
FIG. 41A

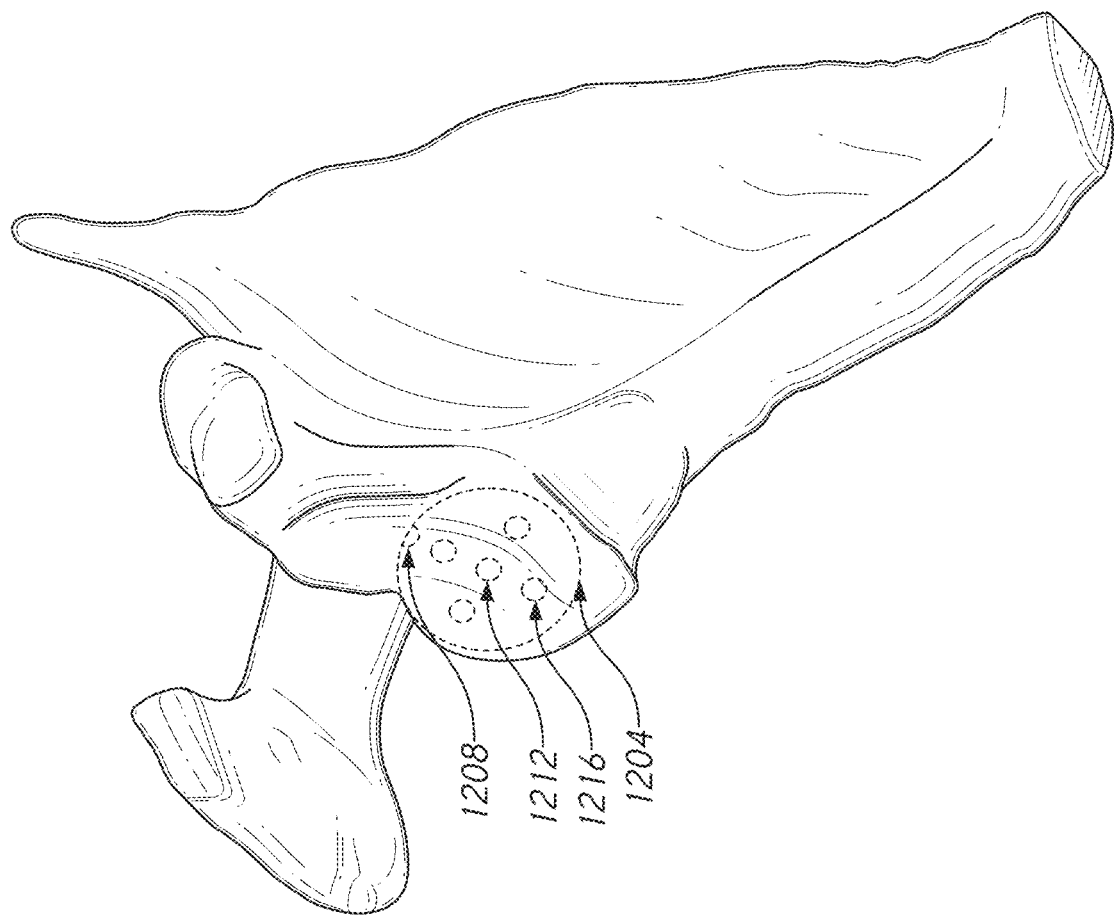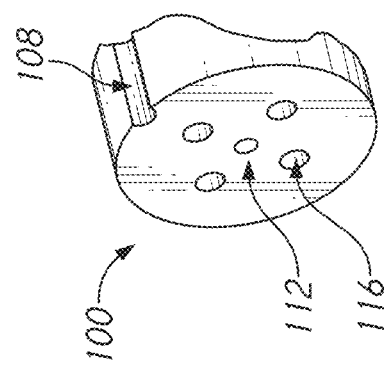
FIG. 42A

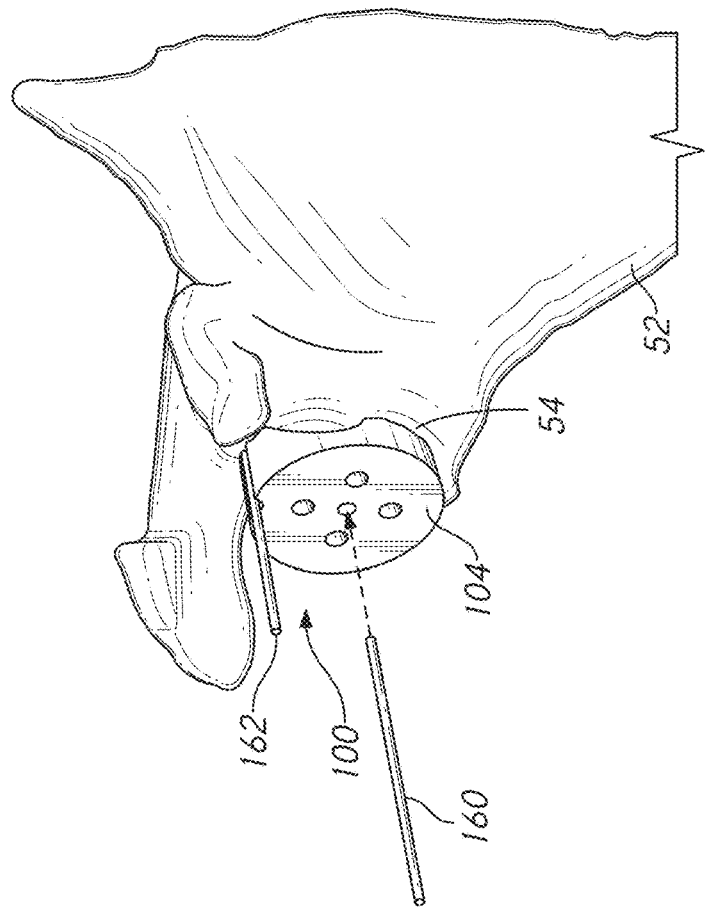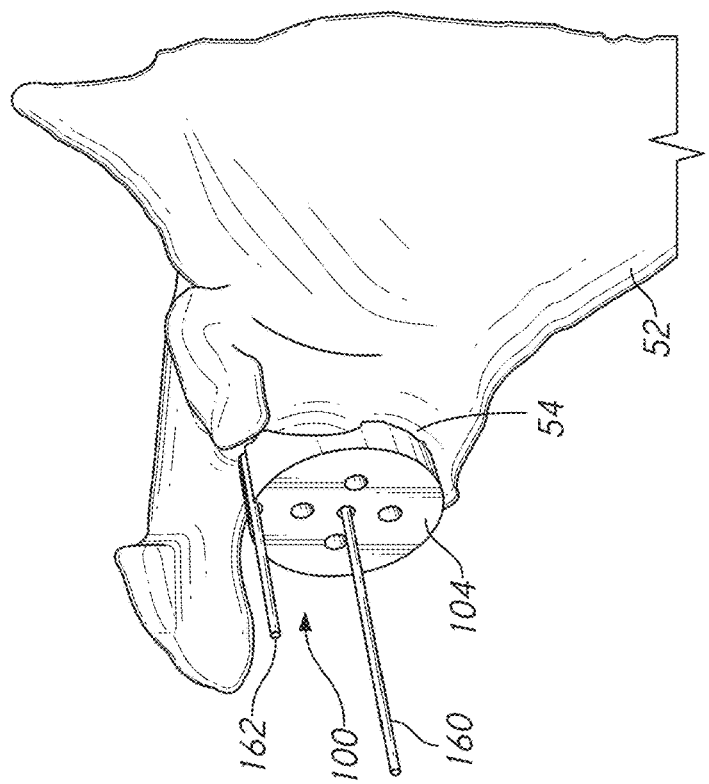
FIG. 42D
FIG. 42E

GUIDES AND INSTRUMENTS FOR IMPROVING ACCURACY OF GLENOID IMPLANT PLACEMENT

CROSS-REFERENCE TO RELATED APPLICATIONS

This application is a continuation of U.S. patent application Ser. No. 17/248,788, filed on Feb. 8, 2021, which is a continuation-in-part of PCT International Application No. PCT/US2019/046039, filed on Aug. 9, 2019, which claims benefit of U.S. Provisional Application No. 62/717,404, filed on Aug. 10, 2018, the contents of which are incorporated herein by reference in their entirety.

BACKGROUND

Field

The present disclosure relates to patient specific shoulder apparatuses and methods.

Description of the Related Art

Shoulder arthroplasty is an important medical technology innovation. The procedure can involve replacing or repairing the articular surface of one or both of the humerus and the glenoid to restore shoulder joint function, to eliminate shoulder joint pain, and to improve quality of life for patients with debilitating shoulder joint pain.

Various tools are used to assist a surgeon to prepare the bones of the shoulder joint during shoulder arthroplasty procedures. These tools can include guide wires, guide pins, and cutting blocks that can guide reamers and bone saws to remove part of the bone(s) to mate with standard bone interfaces. In some cases, several guides are required to produce a good surgical result for the patient.

Patient specific technology also has begun to be applied to joint arthroplasty. Such technology can involve obtaining imaging of the joint. From that imaging, tools can be made that are tailored to the specific patient. While this can be an advance, patient specific tools may not reduce the number of tools or the complexity of the procedure.

SUMMARY

There is a need for improved surgical tools that can improve placement of articular implants of the glenoid. There is a need for improved surgical guides that can aid in orienting glenoid articular implants. There is a need for improved surgical guides that can aid in forming channels for screws and other anchors for glenoid articular implants. There is a need for surgical guides that have improved stability and for guides that can be placed on the glenoid without obstructing, interacting with and potentially being disrupted by or disrupting the position or operation of tissue retractors and other surgical tools. There is a need for patient specific surgical guides that can provide any or all of these and other improved characteristics. There is a need for combining multiple guide functions into a single guide to improve fit to the patient but also to reduce the complexity of the tools related to shoulder arthroplasty.

In one embodiment, a patient-specific glenoid guide is provided. The glenoid guide has a body, a locating feature, a K-wire guide channel, and a plurality of peripheral channels. The body has a lateral surface and a medial surface. The medial surface has a patient matched portion. The patient matched portion is configured as a negative surface of a glenoid portion of a scapula of a specific patient. The locating feature is disposed on or through the body. The locating feature is configured to reference a guide pin to locate the body relative to a glenoid. The K-wire guide channel extends through the body from a K-wire entrance disposed on the lateral surface to a K-wire exit disposed in the patient matched portion of the medial surface. The peripheral channels extend through the body from a drill entrance disposed on the lateral surface to a drill exit disposed in the patient matched portion of the medial surface. The peripheral channels can be used to prepare bone for anchors, which can be screws, pegs or other implant connectors.

In another embodiment a patient specific anchor trajectory guide is provided. The anchor trajectory guide includes a body, a locating feature and a plurality of peripheral screw apertures. The body has a lateral surface and a medial surface. The medial surface has a patient matched portion that is configured as a negative surface of an articular portion of a glenoid. The locating feature is disposed on or through the body. The locating feature is configured to reference a guide pin to locate the body relative to a glenoid. The peripheral screw apertures extend through the body from an entrance disposed on the lateral surface to an exit disposed in the patient matched portion of the medial surface. The peripheral screw apertures are located and oriented to provide good purchase in scapular bone around the glenoid for a specific patient.

In another embodiment a method is provided. The method can be employed to prepare a glenoid for an implant. In the method a glenoid of a patient is exposed. A body of a glenoid guide is advanced toward the glenoid until a first side of the guide is in contact with an articular surface of the glenoid. A patient matched surface on the first side of the guide is placed in contact with a portion of the articular surface of the glenoid to which the patient matched surface has been configured as a negative. The method can involve rotationally and/or translationally aligning the guide with the glenoid. A drill is advanced along a planned trajectory defined by a bone preparation channel defined through the body of the glenoid guide. The planned trajectory extends along an axis centered on a drill entrance and on a drill exit disposed on the patient matched surface. The drill entrance can be disposed on the second side of the body. A screw channel is formed in a scapula along the axis. An implant component is secured to the scapula by advancing a screw through the implant and into the screw channel.

In another embodiment a patient-specific glenoid guide is provided that includes a body, a guide channel, and a plurality of peripheral screw channels. The body has a lateral surface and a medial surface. The medial surface has a patient matched portion. The patient matched portion is configured as a negative surface of a glenoid portion of a scapula of a specific patient. The guide channel can be a K-wire guide channel. The K-wire guide channel extends through the body from a K-wire entrance disposed on the lateral surface to a K-wire exit disposed in the patient matched portion of the medial surface. The peripheral screw channels extend through the body from a drill entrance disposed on the lateral surface to a drill exit disposed in the patient matched portion of the medial surface.

In some embodiments, a patient-specific glenoid guide is provided that includes a body, a plurality of peripheral members, and a channel. The body has a lateral surface and a medial surface. The medial surface of the body has a patient matched portion configured as a negative surface of a glenoid portion of a scapula of a specific patient. The plurality of peripheral members extends radially outward from an outer periphery of the body. Each of the plurality of peripheral members has a contact member. In some implementations, the contact member has a patient-specific portion and a non-contoured portion. The channel extends through the body from a channel entrance disposed on the lateral surface to a channel exit disposed on the medial surface. The channel may be configured to directly or indirectly receive a guide pin or a drill. In some embodiments, a patient-specific glenoid guide is provided that includes a body, a locating feature, and a channel. The body has a lateral surface and a medial surface. The medial surface of the body has a patient matched portion configured as a negative surface of a glenoid portion of a scapula of a specific patient. The locating feature is disposed on or through the body configured to reference a guide pin to locate the body relative to a glenoid. The locating feature may extend radially outward from the body. In some implementations, the locating feature includes an enclosed channel. The channel extends through the body from an entrance disposed on the lateral surface to an exit disposed on the medial surface.

In some embodiments, a method is provided. The method may include exposing a glenoid of a patient and removing soft tissue from a surface of the glenoid. A body of any of the above-described glenoid guides may be advanced toward the glenoid. When positioned, a contact member of each of the plurality of peripheral members contacts a rim of the glenoid. For example, the contact member may be patient-matched to conform to the rim. A drill may be advanced along a planned trajectory defined by an axis of a bone preparation channel defined through the body of the glenoid guide. An anchor channel may be formed in a scapula along the axis. An implant component may be secured to the scapula by advancing the implant or a bone screw into the anchor channel.

In a further embodiment, a patient-specific glenoid guide is provided that includes a body having a lateral surface and a medial surface. The medial surface has a patient matched portion being configured as a negative surface of a glenoid portion of a scapula of a specific patient. The glenoid guide has a channel extending through the body. The channel extends through the body from a channel entrance disposed on the lateral surface to a channel exit disposed on the medial surface. A single open space is provided radially between the channel and an inner periphery of the body. The single open space can extend from one side of a spoke to an opposite side of the spoke. The spoke can be a single spoke in some embodiments. The single open space can extend more than 120 degrees between circumferential ends of the open space.

The glenoid guide having a single open space can also have a plurality of peripheral members. The peripheral members can extend radially outward from an outer periphery of the body. The peripheral members have contact members.

Any feature, structure, or step disclosed herein can be replaced with or combined with any other feature, structure, or step disclosed herein, or omitted. Further, for purposes of summarizing the disclosure, certain aspects, advantages, and features of the inventions have been described herein. It is to be understood that not necessarily any or all such advantages are achieved in accordance with any particular embodiment of the inventions disclosed herein. No aspects of this disclosure are essential or indispensable.

BRIEF DESCRIPTION OF THE DRAWINGS

These and other features, aspects and advantages are described below with reference to the drawings, which are intended for illustrative purposes and should in no way be interpreted as limiting the scope of the embodiments. Furthermore, various features of different disclosed embodiments can be combined to form additional embodiments, which are part of this disclosure. In the drawings, like reference characters denote corresponding features consistently throughout similar embodiments. The following is a brief description of each of the drawings.

FIG. 7 is a cross-sectional view of the guide of FIG. 3 taken at section plane 7-7 shown in FIG. 5;

FIG. 8 is a cross-sectional view of the guide of FIG. 3 taken at section plane 8-8 shown in FIG. 5;

FIG. 41A-41B illustrate a modular embodiment of a patient specific glenoid guide; and FIGS. 42A-42G illustrate methods of preparing a glenoid using patient specific glenoid guides.

DETAILED DESCRIPTION OF THE PREFERRED EMBODIMENT

This application is directed to shoulder joint arthroplasty apparatuses and methods, which in some cases are patient specific. Section I discusses shoulder anatomy and a glenoid implant anchoring assembly. Section II discusses a variety of patient matched glenoid guide components that streamline and enhanced the accuracy of glenoid implantation preparation procedures. Section III discusses methods of using patient matched glenoid guide components.

I. Shoulder Anatomy and Glenoid Implant Assemblies

Figure 1:
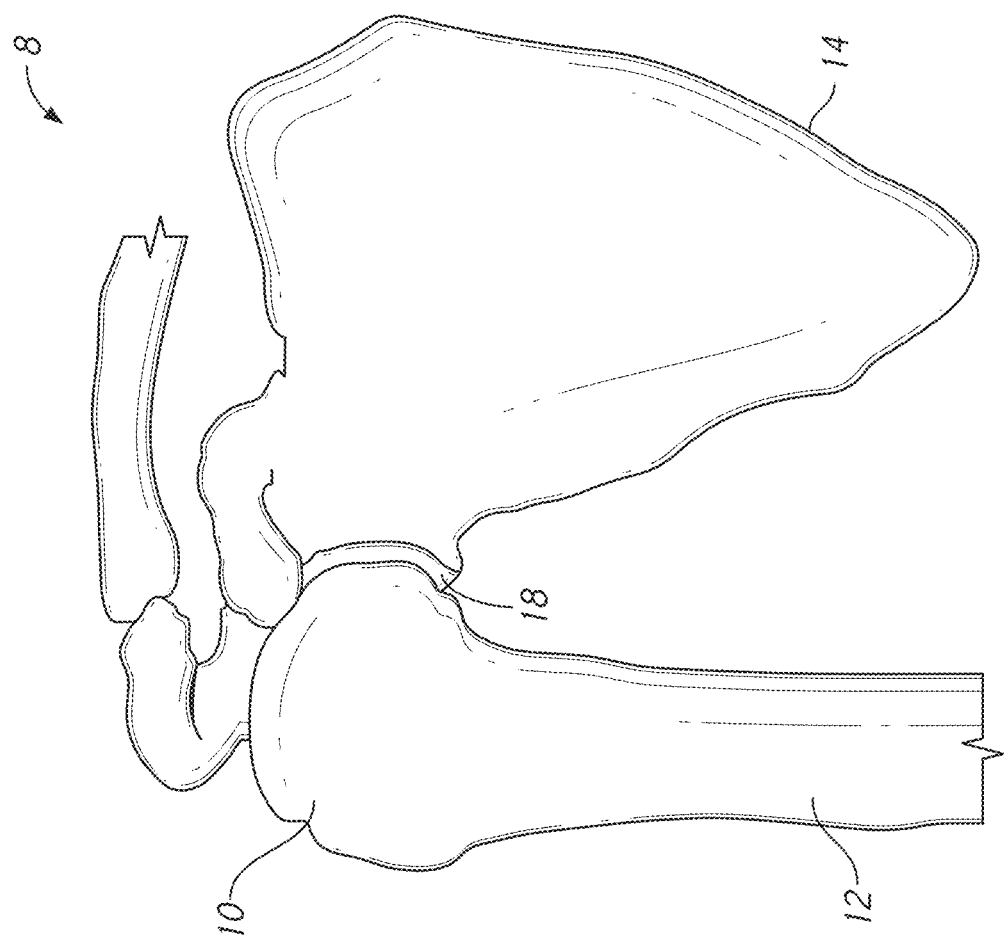
FIG. 1 shows a glenohumeral shoulder joint.

FIG. 1 illustrates skeletal components of a glenohumeral joint 8. In shoulder arthroplasty surgery the joint 8 is accessed via an incision formed in the tissue over the joint 8. A head 10 of the humerus 12 can be separated from the scapula 14 to provide access to the glenoid 18. An articular implant can repair or replace the articular surface of the glenoid 18. The articular surfaces of the humerus 12 and the glenoid 18 can be reversed in some cases, providing a concave articular member on the humerus 12 and a convex articular member, called a glenosphere, on the glenoid 18. In some cases the glenoid surface is worn away and, therefore, is enhanced to make up for this wear.

Whether the wear is significant or not, the glenoid 18 is prepared to mate with a glenoid implant. Better outcomes result from the glenoid implant being oriented properly on the glenoid. Such preparation can include reaming the glenoid 18, followed by attachment of the articular implant to the reamed surface. The preparation and reaming of the glenoid and the placement of the implant can be accomplished by a series of guiding instrument that can be generic or patient specific.

Figure 2:
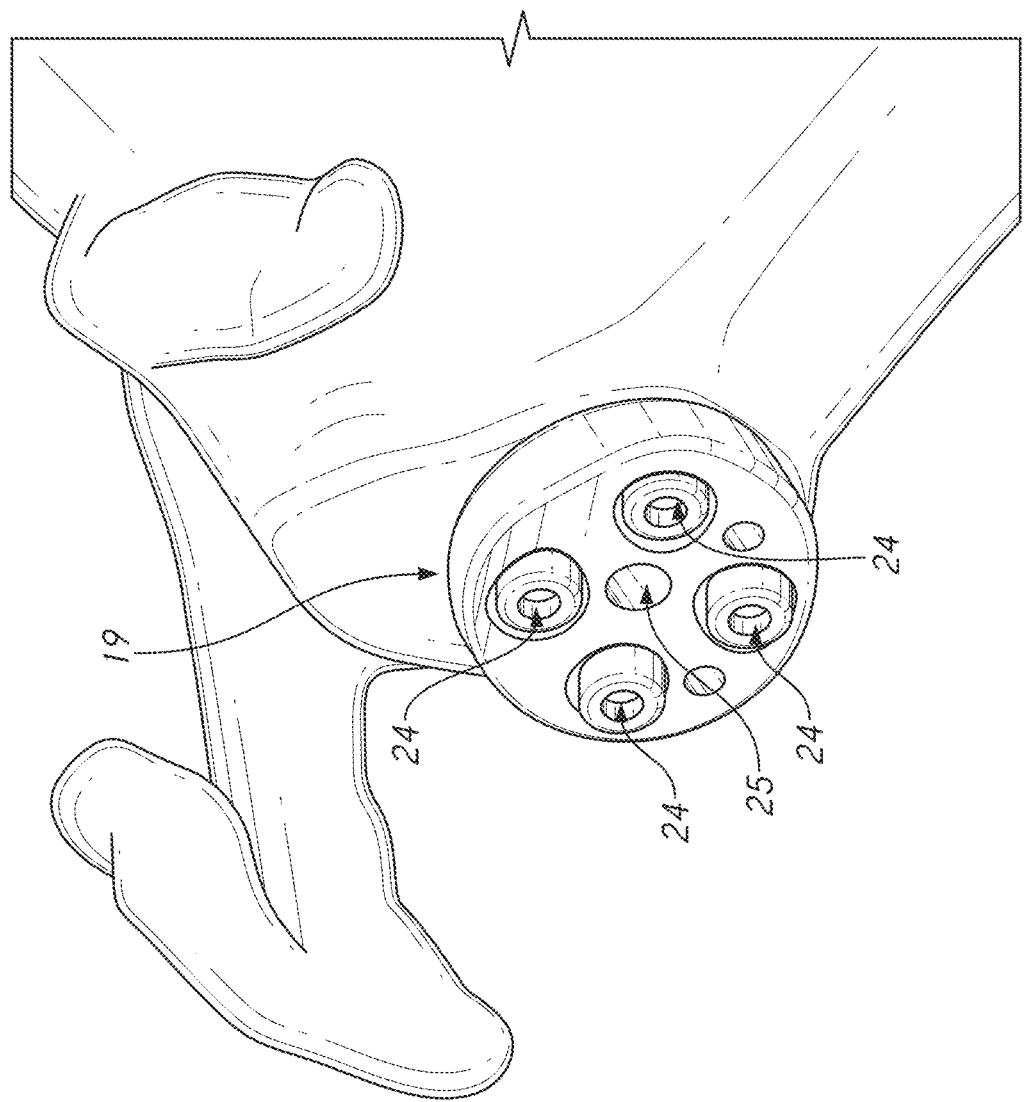
FIG. 2 shows an embodiment of a reverse shoulder glenoid assembly.
Figure 4:
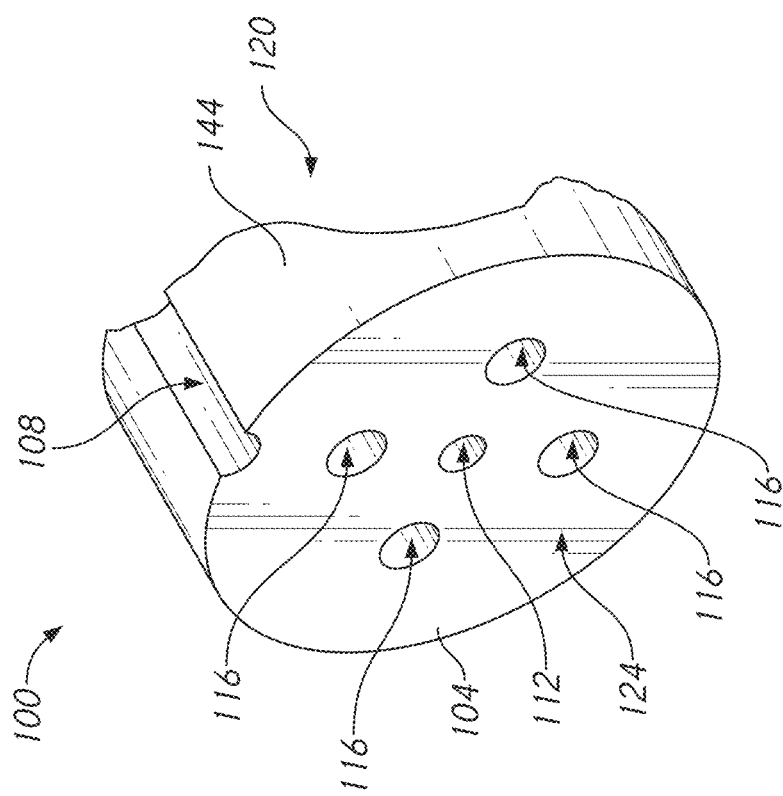
FIG. 4 is a perspective view of the glenoid guide shown in FIG. 3 separate from the scapula.
Figure 3:
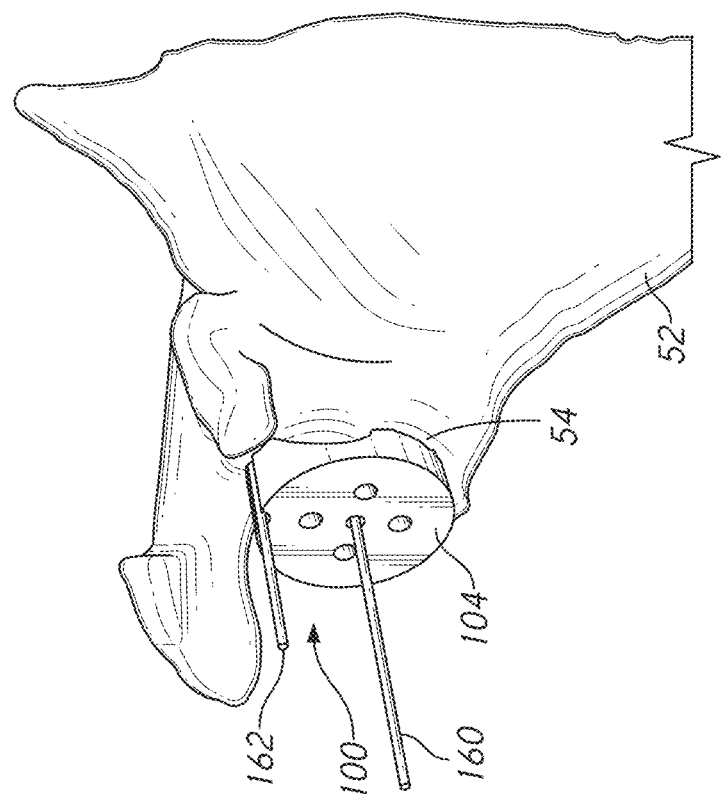
FIG. 3 is a perspective view of a patient specific glenoid guide adapted to provide affirmative rotational position control, the guide applied to the glenoid of the patient.

FIG. 2 illustrates a reverse shoulder glenoid assembly 19. The glenoid assembly 19 includes a baseplate 20 that can be secured to the glenoid by one or more of a central anchor and one or a plurality of peripheral anchors 24. In the case of reverse shoulder arthroplasty the baseplate 20 can be secured to a glenosphere, as described above. The glenosphere can be couple to a concave humeral component anchored to the humerus of the shoulder joint to provide joint motion.

II. Patient Matched Multi-Function Glenoid Guides

FIGS. 3-41B illustrate a variety of glenoid guides that provide multiple functions in connection with a patient matched or patient specific glenoid preparation procedure.

A. Patient Matched Glenoid Guides with Glenoid Scale Guide Body

FIGS. 3-12 illustrate a first embodiment of a patient-specific glenoid guide 100 that includes a locating feature configured to rotationally align the guide 100. The guide 100 is configured to provide multiple functions as discussed further below. The functions can include one or more of locating the patient-specific glenoid guide 100 rotationally at a locating feature 108, guiding a central guide pin 160 such as a K-wire into the glenoid 54 through a K-wire guide channel 112, and guiding the preparation of anchor channels in the scapula 52 through peripheral channels 116. As a result, the guide 100 can combine the function of multiple guides into one guide reducing the number of surgical instruments to be prepared, improving the performance of the guides and in some cases providing both of these advantages.

Figure 5:
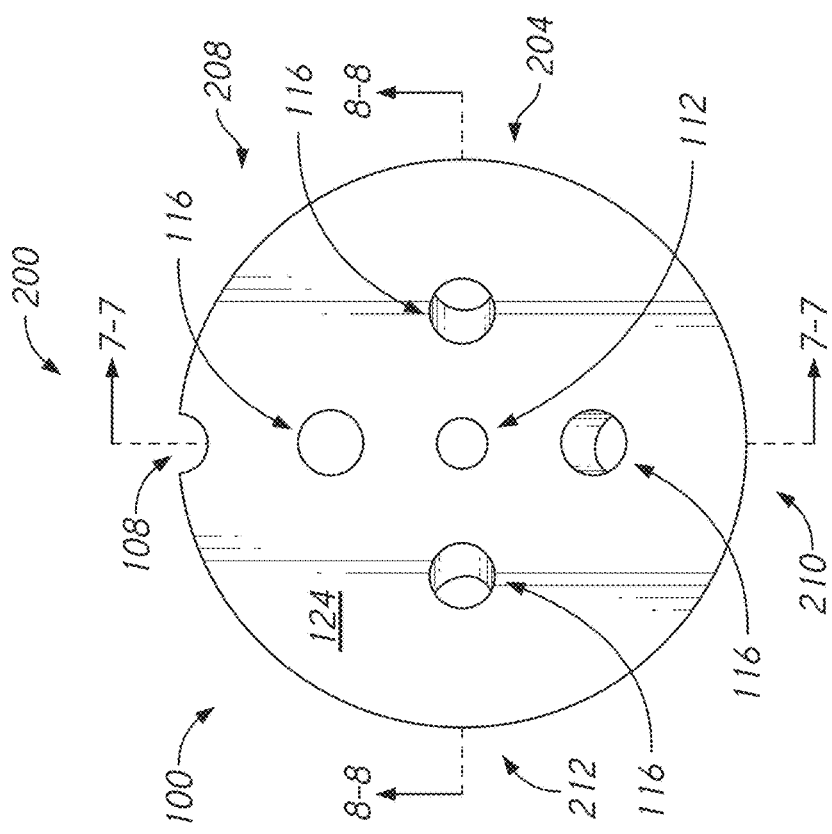
FIG. 5 is a lateral side view of the glenoid guide shown in FIG. 3.
Figure 10:
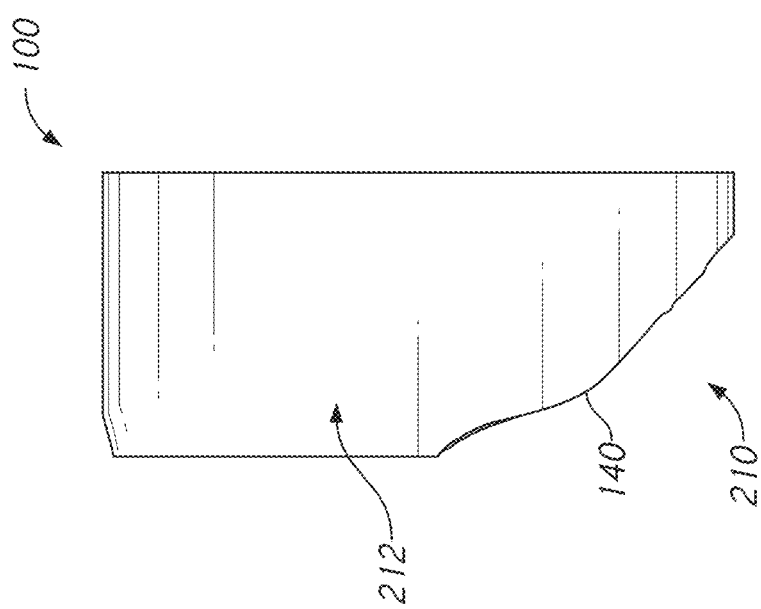
FIG. 10 is a side view of a posterior portion of the guide of FIG. 3.
Figure 9:
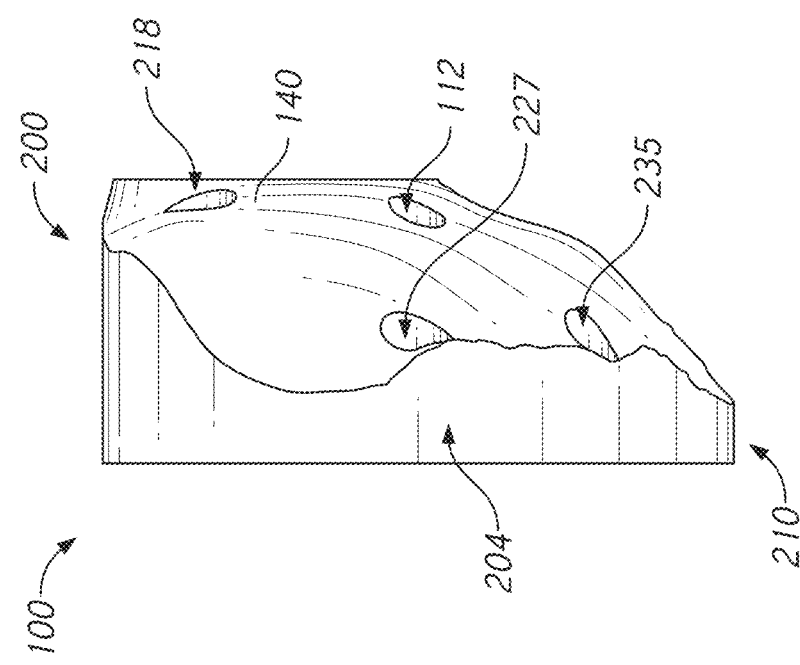
FIG. 9 is a side view of an anterior portion of the guide of FIG. 3.
Figure 12:
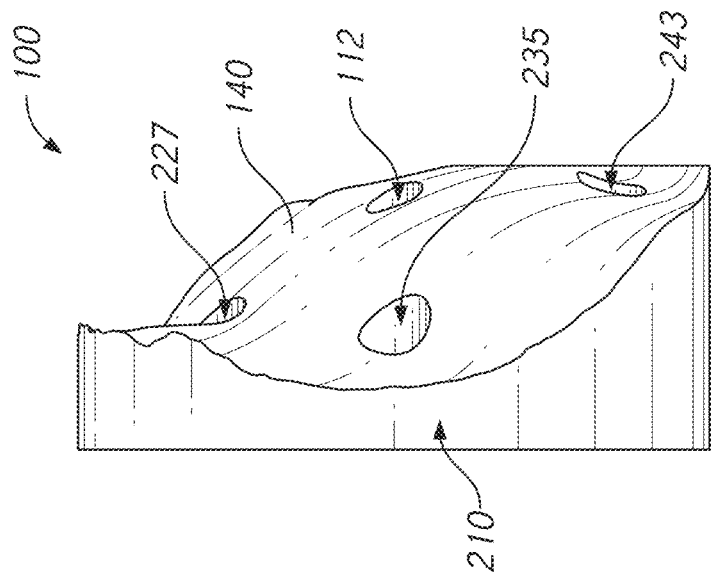
FIG. 12 is a bottom side view of the guide of FIG. 3.
Figure 11:
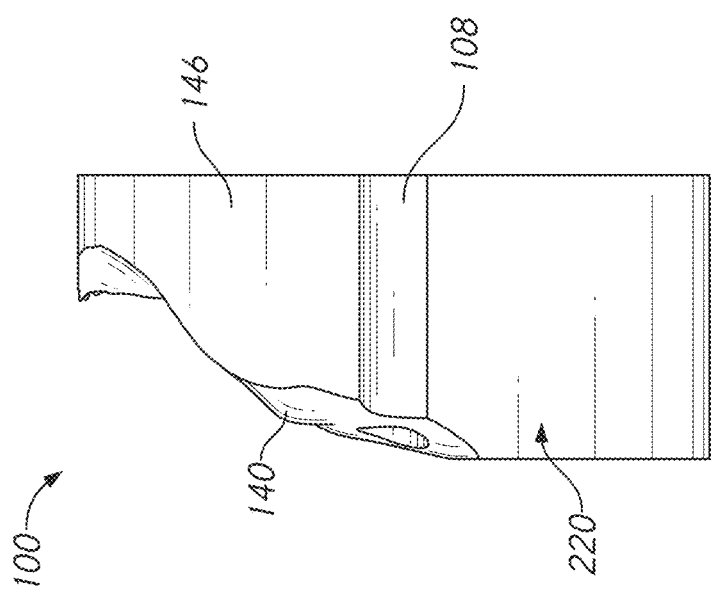
FIG. 11 is a top side view of the guide of FIG. 3.
Figure 13:
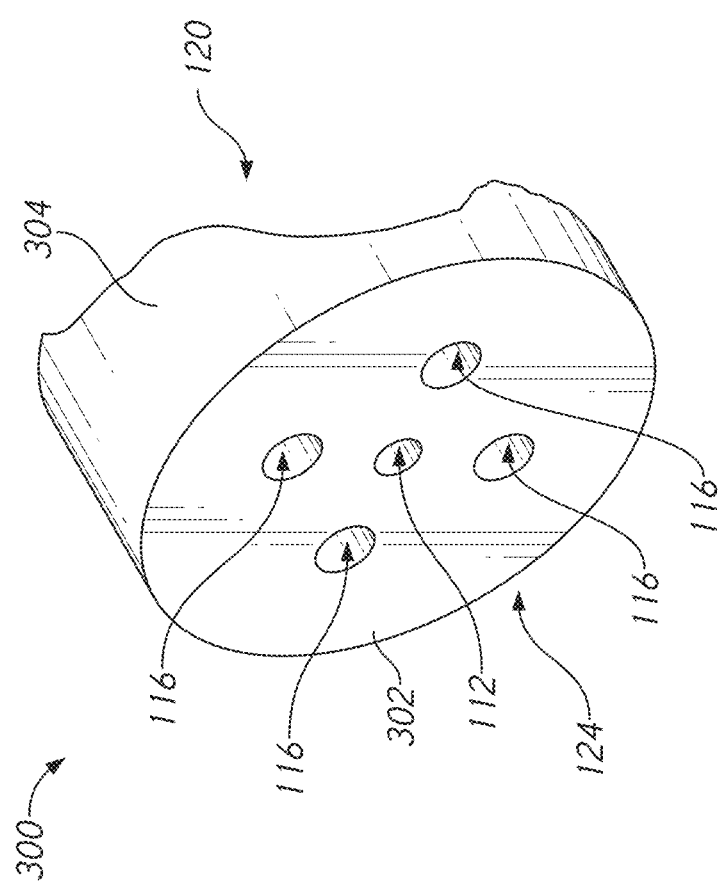
FIG. 13 is a perspective view of another embodiment of a patient specific glenoid guide.

The patient-specific glenoid guide 100 has a body 104 that in the illustrated embodiment is generally disc-shaped. The body 104 has a periphery 144 that is convex in overall form as viewed from a lateral side, as shown in FIG. 5. The body 104 is generally matched to the size of the glenoid 54 of the scapula 52. As a result the body 104 is sized to fit through the incision made to expose the shoulder and in particular the glenoid 54. The body 104 can be sized smaller than the glenoid 54 and can have more complex peripheral shapes to expose portions of the glenoid 54 as discussed further below. The body 104 has a first side 120 and a second side 124 separated from the first side 120 by the periphery 144. The first side 120 is sometimes referred to herein as a medial side because when the body 104 is placed against the glenoid 54 the first side 120 is closest to the medial plane of the patient. The second side 124 is sometimes referred to as a lateral side because when the body 104 is placed against the glenoid 54 the second side 124 is lateral of the glenoid 54 and is lateral of the first side 120.

As will be discussed below, a locating feature 108 is provided at or in the periphery 144 of the body 104 to aid the surgeon in positioning the body 104 when the patient-specific glenoid guide 100 has been inserted through the incision to the glenoid 54. The locating feature 108 can extend between the first side 120 and the second side 124, e.g., from an end at the first side 120 to an end at the second side 124.

The K-wire guide channel 112 channel can be formed generally in the center or central region of the body 104 and can extend between the first side 120 and the second side 124, e.g., from the second side 124 to the first side 120. The K-wire guide channel 112 can extend at any angle relative to the second side 124 of the body 104. The K-wire guide channel 112 can be perpendicular to the second side 124. The K-wire guide channel 112 can receive a K-wire or other central guide pin 160 at an entrance formed on the second side 124 of the body 104. The central guide pin 160 can be further advanced through an exit of the K-wire guide channel 112 into the glenoid 54. The central guide pin 160 can be further advanced to a sufficient depth to allow subsequent procedures to be performed thereover, as discussed further below.

The peripheral channels 116 are disposed about the body 104. The peripheral channels 116 can be disposed between the K-wire guide channel 112 and the periphery 144 of the body 104. In one embodiment, the peripheral channels 116 can include four channels that have entrances on the second side 124. The entrances of the peripheral channels 116 can be disposed in a generally cross-shaped pattern, with hole entrances located on each of two perpendicular planes. The planes intersecting the hole entrances can extend vertically (relative to the orientation of the glenoid in the upright patient, or as shown as section plane 7-7 in FIG. 5) and horizontally (relative to the orientation of the glenoid in the upright patient, or as shown as section plane 8-8 in FIG. 5) and can extend perpendicular to the second side 124 of the body 104. The peripheral channels 116 can be used to form peripheral screw channels in the glenoid 54 using a channel forming instrument, such as a drill, as discussed further below. The peripheral channels 116 are sometimes referred to herein as bone preparation channels.

The peripheral channels 116 preferably are patient matched in at least one aspect. In this context, the peripheral channels 116 can be patient matched in that they are oriented through the body 104 with reference to the scapula 52 to provide a good result in anchor placement. With reference to FIG. 2, the peripheral anchors 24 secure the baseplate 20 to the glenoid 54. The glenoid 54 is a thin almost plate like bone structure. As a result, the orientation of the peripheral anchor 24 if not carefully controlled can cause the ends thereof away from the baseplate 20 to penetrate the wall of the scapula 52 to engaged soft tissue adjacent to the scapula or to not reach cortical bone where the anchor can more securely engage the bone.

Figure 6:
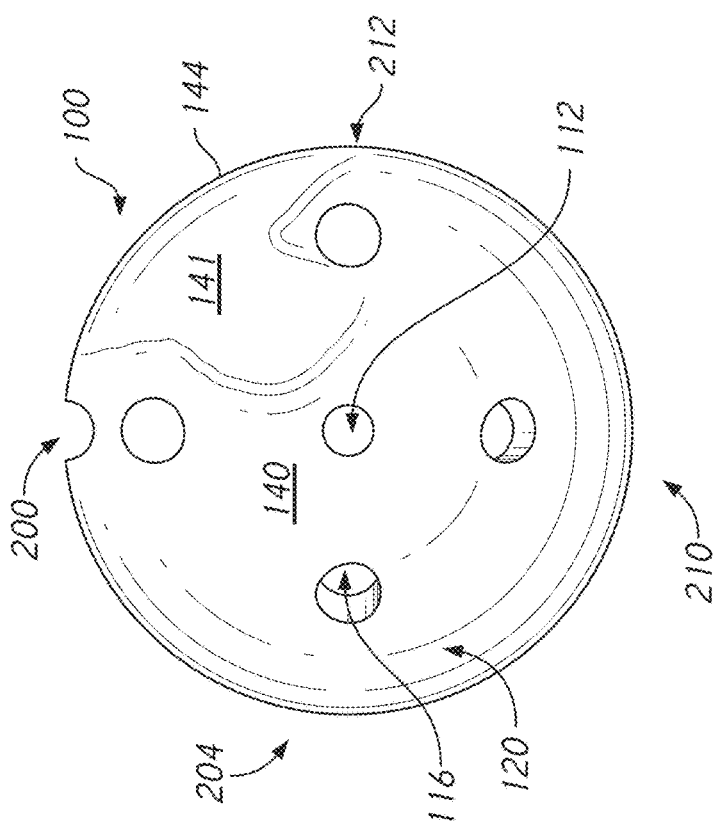
FIG. 6 is a medial side view of the glenoid guide shown in FIG. 3.

FIGS. 5-6 show additional details of the patient-specific glenoid guide 100. The locating feature 108 can be seen to be located at a superior portion 200 of the body 104. The locating feature 108 can be seen in this embodiment to have an open channel 148 configuration. The locating feature 108 can be a concave channel. The locating feature 108 can be semi-circular in one embodiment, e.g., being bounded by an arc subtending 180 degrees. The locating feature 108 can extend from first end at the first side 120 (see FIG. 6) to a second end at the second side 124 (see FIG. 5). Being open, the locating feature 108 can receive a periphery pin 162 (shown in FIG. 3) in more than one direction. For example, the periphery pin 162 can initially enter the locating feature 108 from the second end at the second side 124 and slide laterally to medially along the locating feature 108 of glenoid guide 100 the glenoid 54. The pin 162 also could be advanced through an incision and shifted toward the glenoid guide 100 after both the guide and the pin are advanced to the glenoid 54. The locating feature 108 also can be used to make a bovie mark on the surface of the scapula 52, e.g., in a superior region of the glenoid 54 to facilitate further surgical steps following use of the guide 100. The pin 162 or the bovie mark can thereafter be used to orient an implant, such as a reverse should implant as discussed below in connection with FIGS. 42A-42G.

FIG. 5 shows that the periphery 144 is continuously convex from one side of the locating feature 108 (to the right of the section plane in FIG. 5) to an opposite side of the locating feature 108 (to the left of the section plane in FIG. 5). The continuously convex shape can be a circular shape in one embodiment, or can be oval with a long axis between the superior portion 200 and an inferior portion 210 and a short axis between an anterior portion 204 and a posterior portion 212 of the body 104. FIG. 5 shows that some of the peripheral channels 116 can be aligned with each other. For example, two of the peripheral channels 116 can be disposed on the section plane 7-7 and two of the peripheral channels 116 can be disposed on the section plane 8-8 as discussed above. In one embodiment, each of the peripheral channels 116 is disposed at non-perpendicular orientations relative to the second side 124. The peripheral channels 116 in the superior portion 200 and in the posterior portion 212 are angled to an extent that the portions thereof on the first side 120 of the body 104 are not visible from the second side 124. The peripheral channels 116 in the anterior portion 204 and in the inferior portion 210 are angled to a lesser extent such that the portions thereof on the first side 120 of the body 104 are partially visible from the second side 124. The orientations of the peripheral channels 116 are discussed in greater detail below.

FIG. 6 shows the first side 120 of the body 104 in more detail. The first side 120 includes the patient matched portion 140. The first side 120 also has a non-contoured portion 141 disposed between the patient matched portion 140 and the periphery 144. The non-contoured portion 141 can correspond to the most worn portion of the glenoid 54. The non-contoured portion 141 can correspond to a portion of the glenoid 54 that is not suitable for a patient matched connection to the patient-specific glenoid guide 100. A boundary between the patient matched portion 140 and the non-contoured portion 141 can facilitate at least initial rotational positioning or securement in some embodiments. Also, in some cases, the glenoid guide 100 can be formed as part of a surgical plan in which the glenoid is to be reamed. For example if an osteophyte can be removed by reaming around the area of the osteophyte. The step of reaming can leave the glenoid mostly intact while creating one or more flat or planar zones on the glenoid 54. The non-contoured portion 141 can mate with the flat or planar zone(s) of the glenoid 54. The K-wire guide channel 112 can be disposed perpendicular to the second side 124 and can emerge on the first side 120 in a central region or even in the center of the first side 120. One or more of the K-wire guide channel 112 and the peripheral channels 116 can be disposed in the patient matched portion 140 of the first side 120. In some variations, one or more of the K-wire guide channel 112 and the peripheral channels 116 can be disposed in the non-contoured portion 141. In some variations, one or more of the K-wire guide channel 112 and the peripheral channels 116 can be disposed at the boundary between the patient matched portion 140 and the non-contoured portion 141.

FIGS. 7 and 8 show further details of one embodiment of the patient-specific glenoid guide 100 in the K-wire guide channel 112 and of the peripheral channels 116. The peripheral channels 116 can include a first channel 218 in a superior portion 200 of the guide, a second channel 227 in an anterior portion 204, a third channel 235 in an inferior portion 210, and a fourth channel 243 disposed in a posterior portion 208 of the body 104. The K-wire guide channel 112 extends from a drill entrance 180 and to drill exit 184 for preparing a path for a K-wire. The K-wire guide channel 112 extends along an axis 198. The axis 198 centered on the drill entrance 180, the drill exit 184 and the channel therebetween. The axis 198 can be disposed at any suitable angle, but generally is disposed perpendicular to the second side 124.

In one embodiment the peripheral channels 116 are oriented non-perpendicular to the second side 124. In other embodiments at least one of the peripheral channels 116 are perpendicular to the second side 124. Any of the peripheral channels 116 can be disposed at other angles than illustrated in view of the patient-specific glenoid guide 100 being patient matched. The angles of the peripheral channels 116 can be selected for patient needs, to provide enhanced bone securement and locating in the scapula 52. FIG. 7 shows that a first channel 218 among the peripheral channels 116 can be provided in a superior portion 200 of the patient-specific glenoid guide 100. The first channel 218 can extend from a first channel entrance 220 to a first channel exit 224 through the body 104. The first channel 218 can extend along a first channel axis 226 disposed through the first channel 218. The first channel axis 226 can be disposed at any angle, but as shown is oriented away from the axis 198. In some embodiments, the first channel axis 226 is oriented such that an anchor recess formed through the body 104 has a medial end in the scapula 52 that is farther away from a channel formed along the axis 198 than is an entrance at the glenoid 54 of the recess so formed in the glenoid 54. This arrangement results in at least the anchor disposed along the recess formed along the first channel axis 226 being splayed out or diverging from a perpendicular axis, such as the axis 198 or a similar axis.

The third channel 235 can be disposed in the same plane as or in a single plane with the first channel 218. The third channel 235 can include a third channel entrance 236 and a third channel exit 240. The third channel 235 can extend along a third channel axis 242 disposed between the third channel entrance 236 and the third channel exit 240. The third channel axis 242 can be centered on one or both of the third channel entrance 236 and the third channel exit 240. The third channel axis 242 can be centered in the channel between the third channel entrance 236 and the third channel exit 240. The third channel 235 can be arranged such that the third channel axis 242 is oriented away from the axis 198 on the first side 120 of the body 104. The orientation of the third channel axis 242 and the first channel axis 226 provides that anchors disposed in recesses formed along these axes will be diverging from each other or splayed in the scapula 52. Such anchors will be disposed in a common vertical plane.

The second channel 227 and the fourth channel 243 of the body 104 can be in a common plane, e.g., an anterior-posterior plane as illustrated in FIG. 5. The second channel 227 can include a second channel entrance 228 and a second channel exit 232. The channel between the second channel entrance 228 and the second channel exit 232 can extend along and be centered on a second channel axis 234. The fourth channel 243 be disposed between a fourth channel entrance 244 and a fourth channel exit 248 and can be centered on a fourth channel axis 250 that extends through the fourth channel entrance 244 and the fourth channel exit 248. The second channel axis 234 and the fourth channel axis 250 can be angled away from the axis 198 on the first side 120 of the body 104. The second channel axis 234 and the fourth channel axis 250 can be angled away from each other on the first side 120 of the body 104. The orientation of the second channel 227 and the fourth channel 243 provides that anchors advanced along channels formed along the second channel axis 234 and the fourth channel axis 250 are diverging in a medial direction into the bone. Such anchors may be in a splayed configuration as indicated by the axes 198, 226, 234, 242, 250 in FIGS. 7-8 depending on the particular patient's anatomy.

The orientation of the second channel 227 and the fourth channel 243 provides that distal or free ends of anchors will be directed toward the anterior and posterior walls of the scapula 52. The surgical planning can provide that such distal ends will not penetrate the wall of the scapula 52. The planning can be carried out such that the distal ends are at or in the cortical bone layer.

FIGS. 9-12 illustrate a thickness of the guide 100. The thickness of the guide can be configured to locate a lateral plane that matches a pre-arthritic state of the glenoid. For example the body 104 can be configured such that the second side 124 of the body 104 is located at the pre-operatively determined pre-arthritic lateral position when the first side 120 is in contact with the glenoid 54. The contour on the first side 120 that is seen from the views in FIG. 9-12 can be that which will fill the gap between the second side 124 and the surface of the glenoid 54 with little or no reaming or other change in the arthritic state. The sides with more of the patient matched portion 140 visible will have less thickness from the first side 120 to the second side 124 because the bone is less worn from the pre-arthritic state than in portions where the patient matched portion 140 is less visible or not seen. In another aspect, the position of the second side 124 is less of interest than is the orientation of the axis 198. The patient-specific glenoid guide 100 provides correction of the anteversion/retroversion and superior/inferior inclination of the glenoid from the arthritic state. The correction may bring the glenoid 54 back to a pre-arthritic state or may provide other correction to improve the kinematics of the shoulder joint. In the illustrated embodiment, the patient-specific glenoid guide 100 is configured to position the axis 198 by making the body 104 thicker posteriorly and superiorly. This causes the axis 198 to be rotated anteriorly and inferiorly relative to the eroded or arthritic face of the glenoid.

Use of the patient-specific glenoid guide 100 is discussed in greater detail below in Section III.

FIG. 13-17 illustrate additional embodiments of patient-specific glenoid guides that can generally cover the surface of glenoid 54 or at least cover the portion of the glenoid to which a reverse shoulder baseplate or other glenoid implant is to be positioned.

The patient-specific glenoid guide 300 is similar to the patient-specific glenoid guide 100 except as described differently below. The patient-specific glenoid guide 300 includes in one embodiment a periphery 304 that is continuously convex. In that respect the periphery 304 can be round, oval or other shape but is free from any protrusion, concavities or any peripheral guide structures or members. The patient-specific glenoid guide 300 has multiple functions. For example, the first side 120 is patient matched as discussed above. So the first side 120 is able to locate the patient-specific glenoid guide 300 on the glenoid 54 in a repeatable, predictable, and pre-operatively planned manner. The body 302 has sufficient thickness between the first side 120 and the second side 124 that a surgeon can directly grasp the periphery 304 to manipulate and position patient-specific glenoid guide 300. The patient-specific glenoid guide 300 also has the K-wire guide channel 112 and the peripheral channels 116, which can have any of the configurations described above in connection with the patient-specific glenoid guide 100. Accordingly, the use of the patient-specific glenoid guide 300 with guide pins and tools for preparing the glenoid 54 is similar to that of the patient-specific glenoid guide 100. However, the patient-specific glenoid guide 300 can be deployed without a reference for the rotational alignment of the baseplate 20. The patient-specific glenoid guide 300 may be advantageous where the shape of the first side 120 and a corresponding side of the baseplate 20 are highly rotationally specific such that the surgeon can easily find the correct rotational position by feel.

FIG. 14-17 show a patient-specific glenoid guide 400 that is similar to the guides 100, 300 except as described differently below.

The patient-specific glenoid guide 400 include a guide channel 412 formed in a body 402 thereof that is adapted to receive a pin guide 416. The pin guide 416 can be a non-patient specific guide for advancing the central guide pin 160 into the glenoid 54. The pin guide 416 can include a docking feature 420, such as a tapered distal portion or distal surface. A lumen 424 can extend through the pin guide 416 from a first end adjacent to the docking feature 420 to a second end opposite the first end. The lumen 424 can be sized to slideably receive the central guide pin 160.

Figure 17:
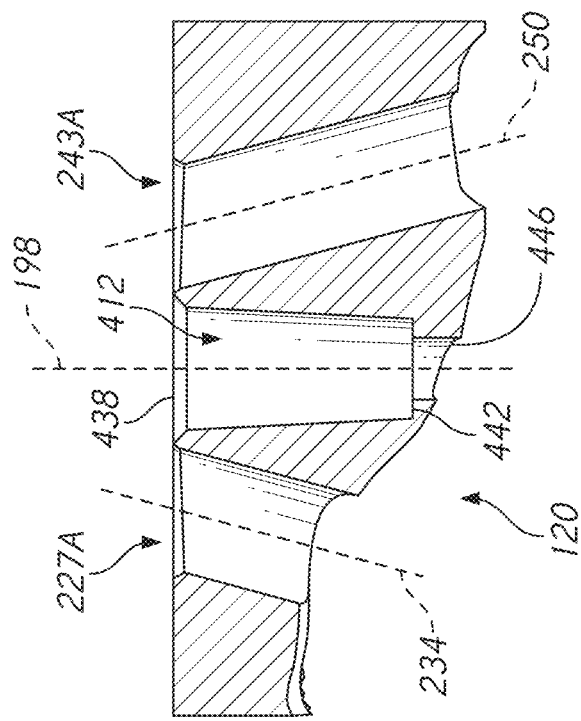
Figure 16:
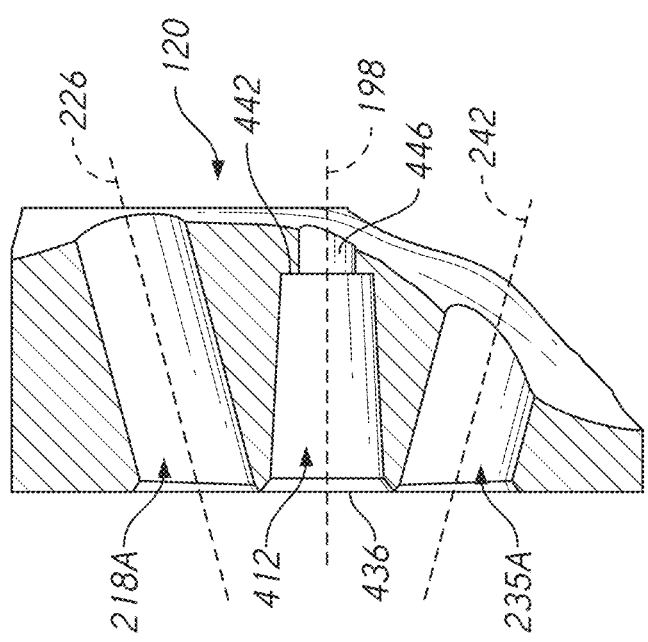

FIGS. 16 and 17 show the guide channel 412 in greater detail in one embodiment. The pin guide 416 includes a guide entrance 438 and a guide seat 442. The guide entrance 438 is configured to slideably receive the docking feature 420 of the pin guide 416. The channel between the guide entrance 438 and the guide seat 442 can be tapered such that a mating of the docking feature 420 and the channel in the guide channel 412 can result in a temporary connection, such as an interference fit. The guide channel 412 also includes a wire exit 446 that allows the central guide pin 160 or a K-wire or similar slender guide member to be advanced through the body 402 and through the glenoid 54 into the scapula 52. In one method, the central guide pin 160 is placed through the pin guide 416. The pin guide 416 can be removed leaving the central guide pin 160 in place. Removing the pin guide 416 provides more clearance for drilling the peripheral channels in the scapula 52 while the central guide pin 160 provides stability for the patient-specific glenoid guide 400 such that the peripheral channels can be quickly and accurately formed.

FIGS. 16 and 17 show that the exits of at least one of and in some cases all of a first channel 218A, a second channel 227A, a third channel 235A, and a fourth channel 243A can be disposed in a patient matched portion of the first side 120. The channels 218A, 227A, 235A, and 243A can be configured to receive a drill guide, which can be a tubular body similar to the pin guide 416. The channels 218A, 227A, 235A, and 243A can be configured for this by having a larger size and/or by being tapered to enable the tubular body to mate at a tapered docking feature or to couple with the tubular body in some other manner. The wire exit 446 of the guide channel 412 also can be disposed in a patient matched portion of the first side 120. The patient matched surface can be mated to the glenoid 54 without reaming or machining the glenoid 54 preserving the bone stock. Thus the patient-specific glenoid guide 400 provides multiple functions all with the first side 120 in contact with the glenoid 54. The patient-specific glenoid guide 400 is advantageous in extending the guide channel 412 with the pin guide 416. The pin guide 416 can act as a handle to hold the patient-specific glenoid guide 400 in place by virtue of one or a plurality of zones of ridges on an outside surface thereof while at the same time allowing the surgeon to insert the central guide pin 160 or other guide member into the opening to the lumen 424 from outside of the area of the incision and retracted tissues there-around. This can help provide a less invasive procedure, e.g., requiring less retraction of tissue.

The method of use of the patient-specific glenoid guide 400 is explained in more detail below in Section III.

B. Patient Matched Glenoid Guides with Enhanced Glenoid Visibility

FIGS. 18-21 illustrate guides that are similar to the patient-specific glenoid guide 100 but that provide enhanced visibility to the surface of the glenoid 54. Enhanced visibility of the surface of the glenoid 54 can enable the surgeon to confirm positioning of the guides or provide the surgeon with other visual cues relating to how well the guide is seated against the surface of the glenoid that enable the surgery to progress smoothly.

Figure 19:
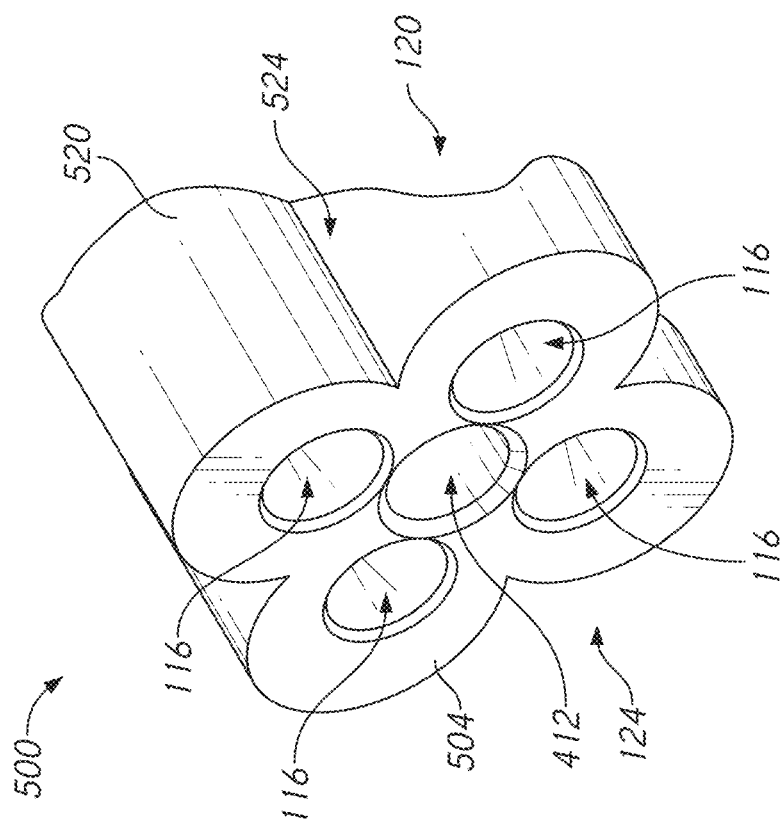
FIGS. 18-21 illustrate another embodiment of a patient specific glenoid guide.
Figure 18:
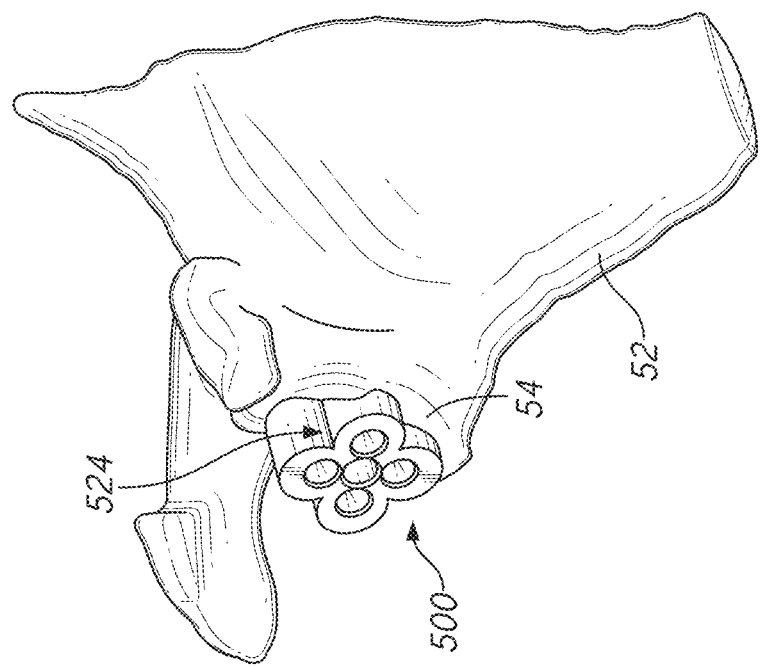
Figure 20:
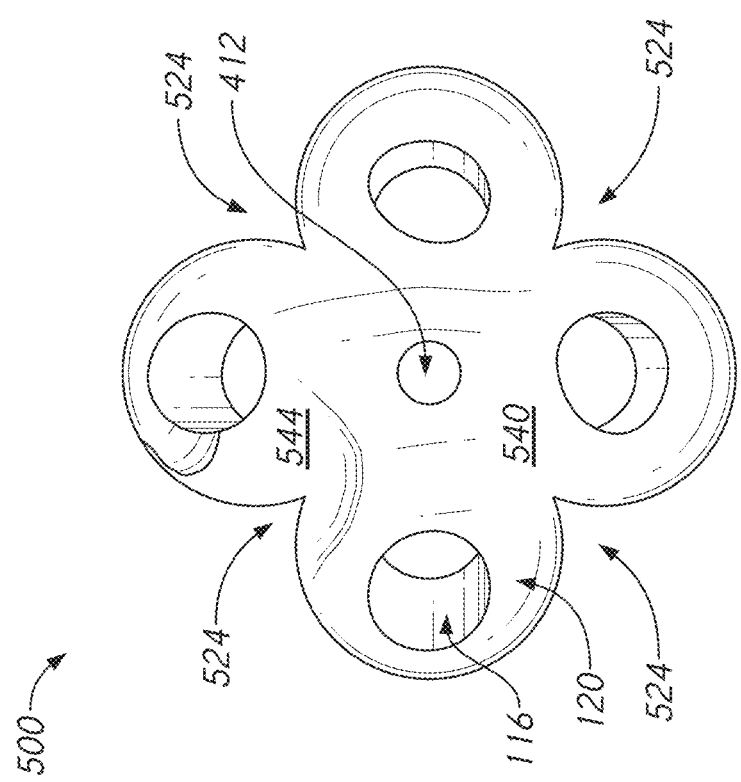
Figure 23:
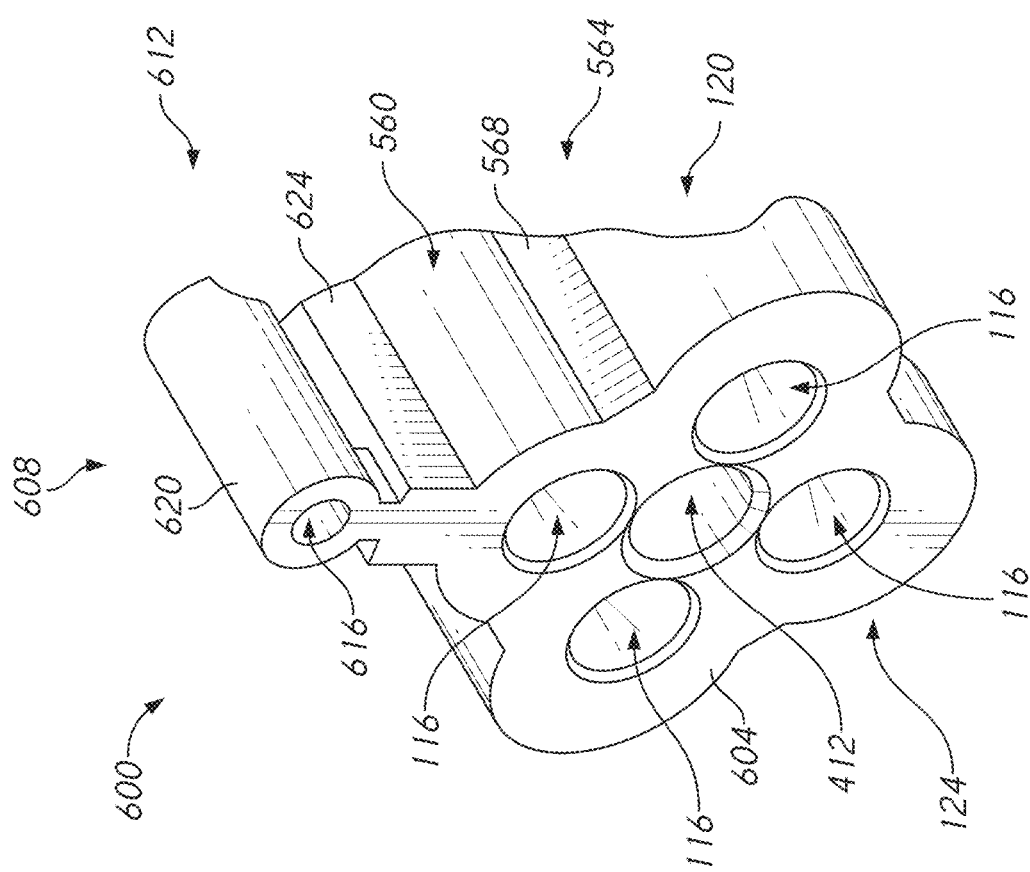
FIGS. 22-27 illustrate another embodiment of a patient specific glenoid guide.

FIG. 18 shows the scapula 52 with a patient-specific glenoid guide 500 configured for enhanced visibility placed thereon. The patient-specific glenoid guide 500 includes a concavity 524 that reduces the profile of a periphery 520 of the guide locally to expose the glenoid 54 within the concavity 524. The patient-specific glenoid guide 500 can include more than one concavity 524, e.g., can include four concavities spaced about the periphery 520. The concavities can be spaced about 90 degrees apart from each other, but could be unevenly spaced in some cases. FIG. 19 shows that the patient-specific glenoid guide 500 includes a body 504 that in one embodiment is clover leaf shaped, enhancing access and/or visibility to four areas of the glenoid 54 around the periphery 520 of the patient-specific glenoid guide 500. The patient-specific glenoid guide 500 can include the K-wire guide channel 112 and the peripheral channels 116, one or more or all of which can have exits on a patient matched surface on the first side 120 of the body 504. FIG. 20 shows the first side 120 in more detail, where the K-wire guide channel 112 and three of four peripheral channels 116 of the patient-specific glenoid guide 500 are completely surrounded by a patient matched portion 140 of the patient-specific glenoid guide 500. One of the peripheral channels 116 is partly bounded by a patient matched portion 540 and partly bounded by a non-contoured portion 544.

Figure 21:
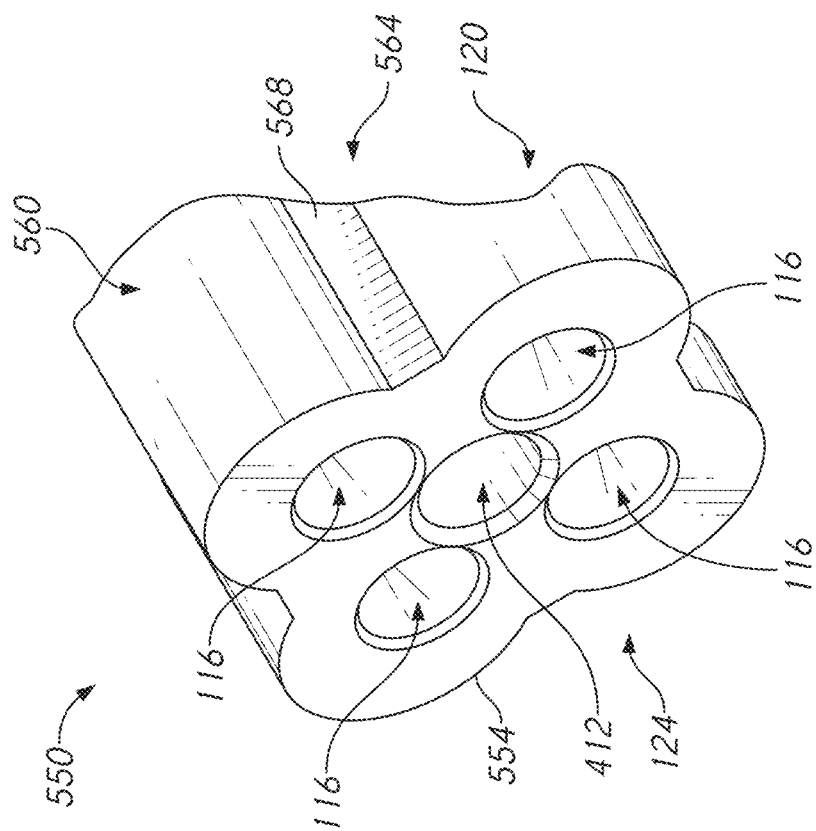

FIG. 21 shows another embodiment of a patient-specific glenoid guide 550 similar to the patient-specific glenoid guide 500. The patient-specific glenoid guide 550 can have any or all of the features of the patient-specific glenoid guide 500. In addition, the patient-specific glenoid guide 550 has a body 554 that includes a periphery 560 that is configured for enhanced visibility and enhanced handling. The periphery 560 includes a concavity 564 that provides enhanced visibility as discussed above in connection with the concavity 524. The concavity 564 also includes a flat surface 568 that extends between the first side 120 and the second side 124. The flat surface 568 provide enough clearance to allow the fingers of the surgeon to grasp the patient-specific glenoid guide 550 between the four outer lobes of the periphery 560 forming the clover leaf shape of the body 554. Accordingly the patient-specific glenoid guide 550 has enhanced configuration for gripping by the surgeon.

The guides 500, 550 reflect a recognition that sufficient guide stability can be achieved by lesser contact area between the first side 120 of the body 504 and the body 554 and the surface of the glenoid 54. For example, the contact area of the first side 120 of the patient-specific glenoid guide 100 can be reduced by up to 10% by the presence of the concavity 524 or the concavity 564 without reducing the accuracy of placement of the patient-specific glenoid guide 500, patient-specific glenoid guide 550 compared to the patient-specific glenoid guide 100. The contact area of the first side 120 of the patient-specific glenoid guide 100 can be reduced by between 10% and baseplate 20% by the presence of the concavity 524 or the concavity 564 without reducing the accuracy of placement of the patient-specific glenoid guide 500, patient-specific glenoid guide 550 compared to the patient-specific glenoid guide 100. The contact area of the first side 120 of the patient-specific glenoid guide 100 can be reduced by between 20% and baseplate 30% by the presence of the concavity 524 or the concavity 564 without reducing the accuracy of placement of the patient-specific glenoid guide 500, patient-specific glenoid guide 550 compared to the patient-specific glenoid guide 100. Greater reduction in contact area can be provided while still maintaining the various hole exits in the patient matched portion 540 to provide a multifunctional guide of the type disclosed herein.

Methods of use of the patient-specific glenoid guides 500, 540 are explained in more detail below in Section III.

C. Patient Matched Glenoid Guides with Enclosed Rotational Location Features

FIGS. 23-27 show a patient-specific glenoid guide 600 that is similar to the patient-specific glenoid guide 550 except as described differently below. The glenoid guide 600 is configured to enable the glenoid 54 to be more visible, e.g. having one or more concavity 564 as discussed above. The patient-specific glenoid guide 600 also can have one or a plurality of flat surfaces 568

The patient-specific glenoid guide 600 has a body 604 that can be cloverleaf shaped as discussed above. The patient-specific glenoid guide 600 also can have a locating feature 608 coupled with a periphery 560 of the body 604. The locating feature 608 can be located at any portion of the periphery 560. In the illustrated embodiment the locating feature 608 can be located at a superior portion 200 of the body 604. In other embodiments, the locating feature 608 is disposed at the anterior portion, the inferior portion, or the posterior portion. In other embodiments, the locating feature 608 is disposed between the superior and anterior portions of the body 604.

In one embodiment, the locating feature 608 includes a peripheral member 612 that extends from the periphery 560. In one version, the peripheral member 612 includes a patient matched contact member 620 that can have a portion disposed on the first side 120 of the body 604. The peripheral member 612 can include an elongated member 624 that has a first end coupled with the periphery 560 and a second end coupled with the patient matched contact member 620. The patient matched contact member 620 can include an enclosed channel 616 disposed between the channel entrance 628 on the first side 120 and the channel exit 632 on the second side 124. The enclosed channel 616 can be sized to allow a periphery pin 162 to pass through to provide a reference position for the baseplate 20 or another glenoid implant.

Figure 26:
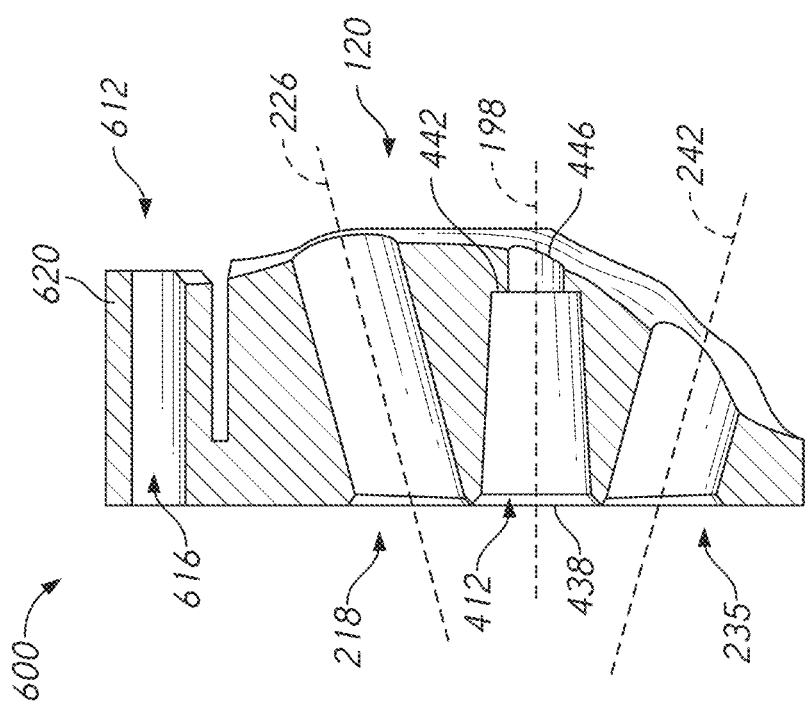

FIG. 26 shows that the patient matched contact member 620 can be coupled to the body 604 at or adjacent to the second side 124 and can have a cantilevered construction, extending to a free end at or adjacent to the first side 120. This reduces the material needed to form the locating feature 608. The elongated member 624 preferably has a rectangular configuration in cross-section with a longer dimension in the direction between the first side 120 and the second side 124 than in the direction transverse to that direction. This configuration can help to maintain the rigidity of the patient-specific glenoid guide 600 when a torque is applied about a superior-inferior axis. This rigidity supports the function of the patient-specific glenoid guide 600 to control the rotation of the body 604 relative to the glenoid 54.

The enclosed channel 616 advantageously allows the patient-specific glenoid guide 600 to accurately place the periphery pin 162 therethrough. The periphery pin 162 can be advanced from outside the incision to a second (or lateral) side of the enclosed channel 616, through the channel, and out of a first (or medial) side and into the glenoid 54 or the scapula 52 adjacent to the glenoid. The enclosed nature of the enclosed channel 616 may more tightly control the specific position of the periphery pin 162 than would be the case with an open channel.

Figure 29:
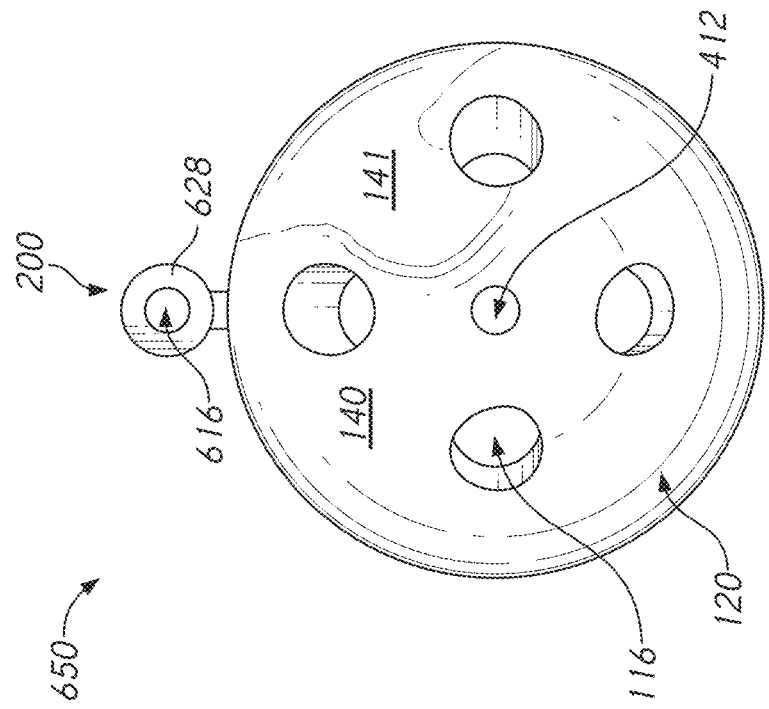
FIGS. 28-29 illustrate another embodiment of a patient specific glenoid guide.
Figure 28:
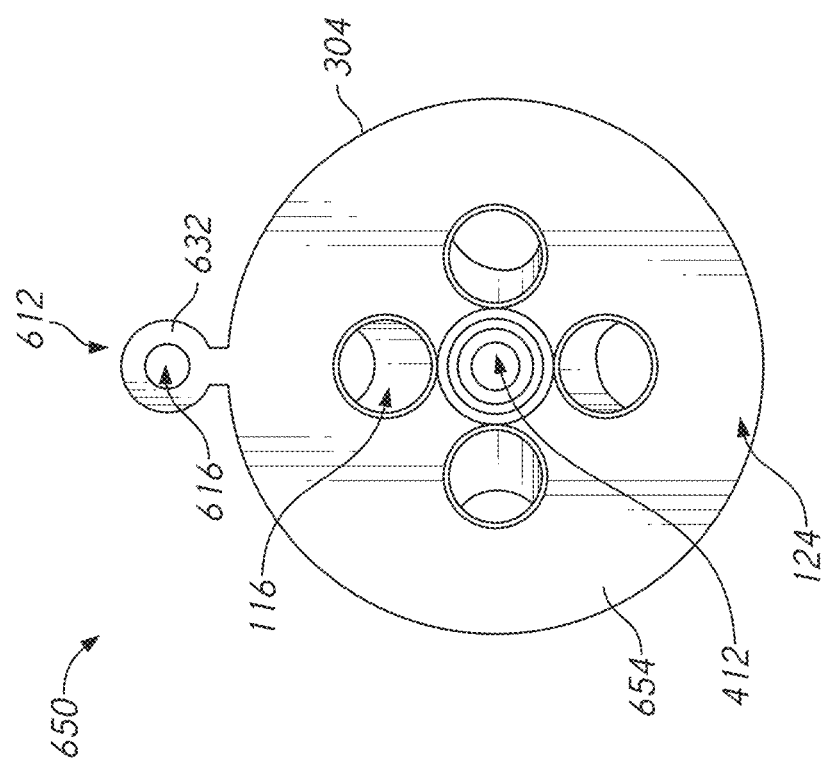
Figure 31:
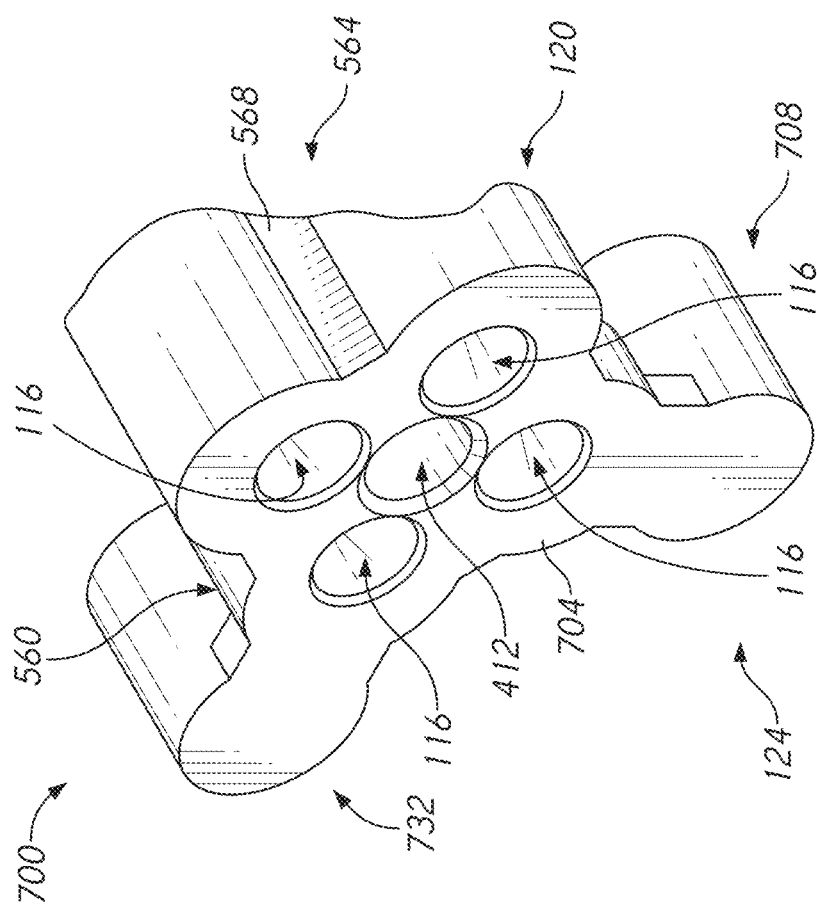
FIGS. 30-35 illustrate another embodiment of a patient specific glenoid guide.
Figure 30:
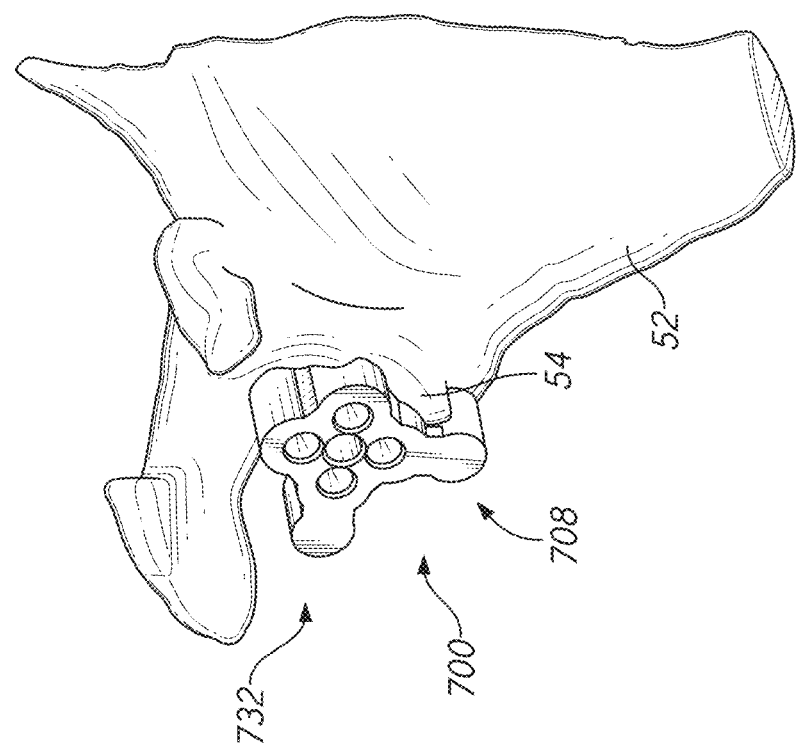
Figure 33:
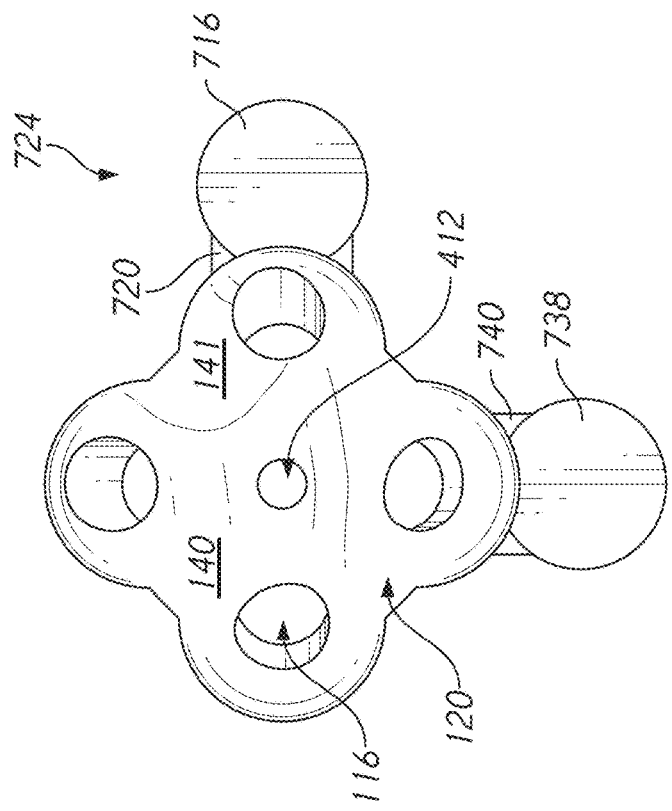
Figure 32:
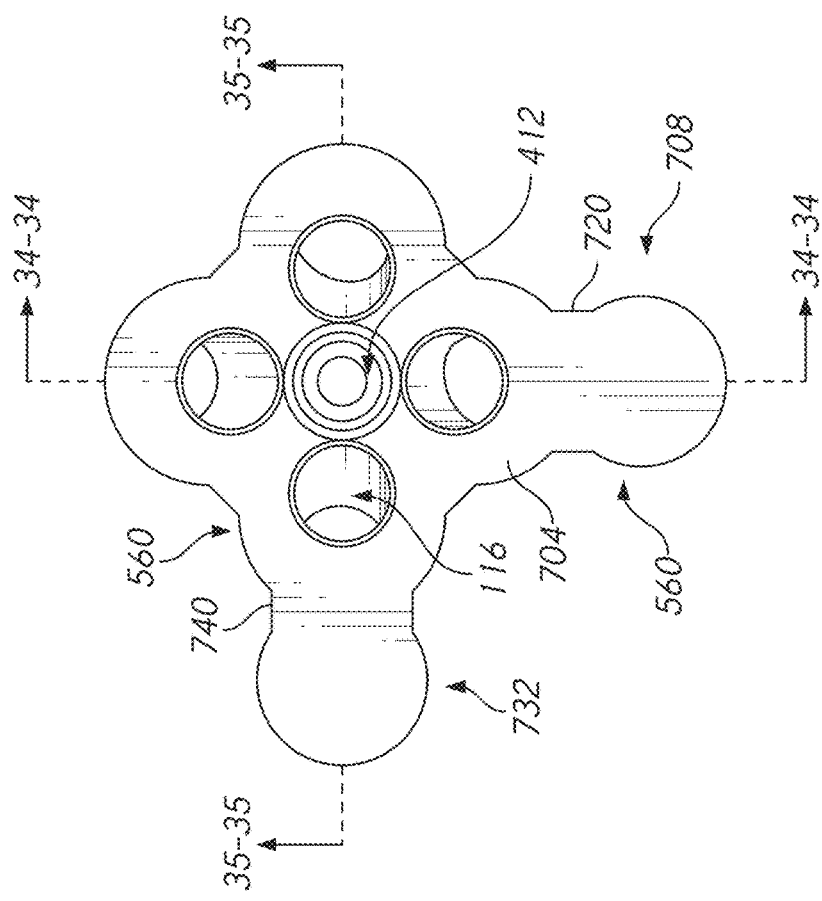
Figure 35:
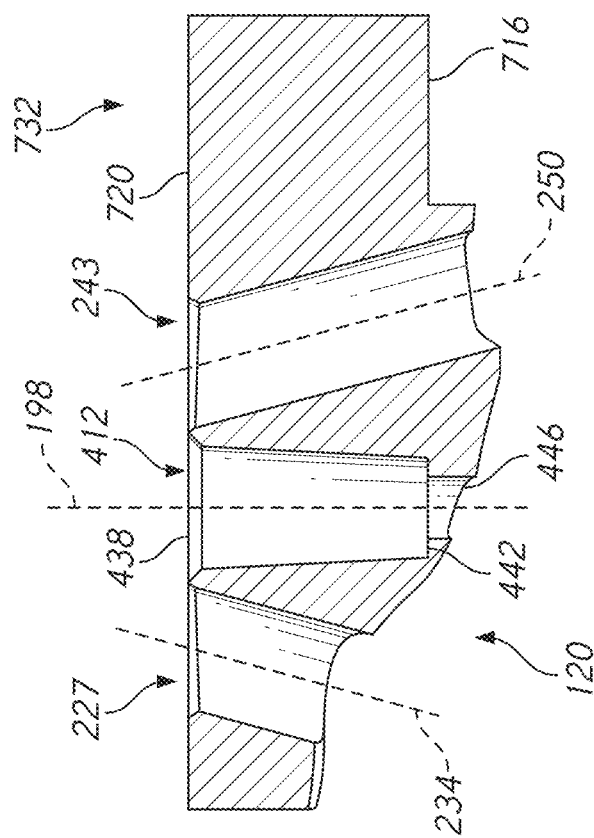
Figure 34:
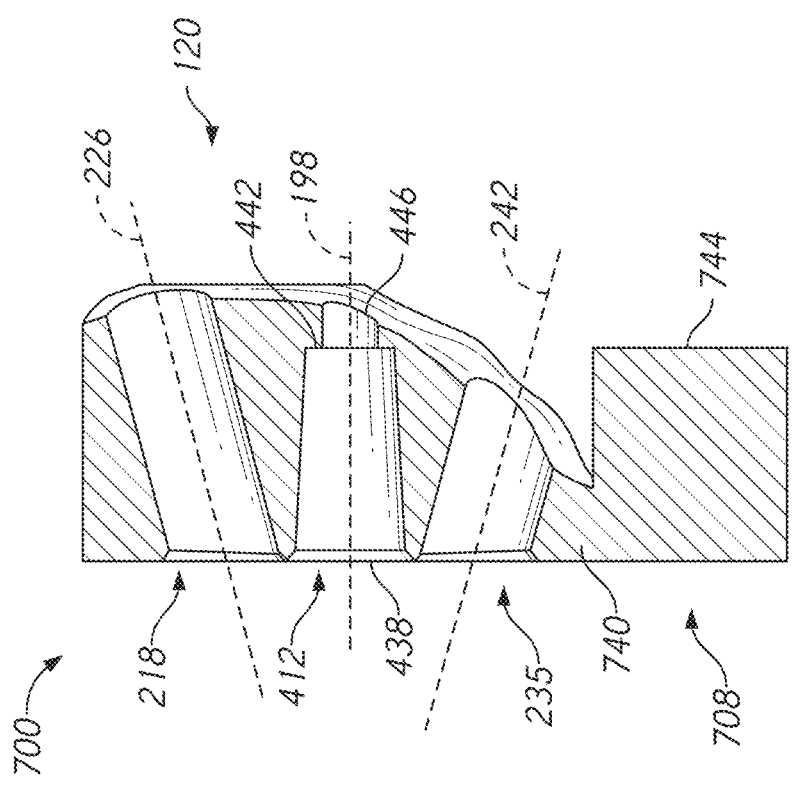

FIGS. 28 and 29 show a patient-specific glenoid guide 650 that is similar to the patient-specific glenoid guide 300 in some respects and to the patient-specific glenoid guide 600 in other respects. The description of these other embodiments is considered to supplement the description of the patient-specific glenoid guide 650. The patient-specific glenoid guide 650 comprises a body 654 that is configured to generally cover the glenoid 54 or a portion thereof that is to receive a glenoid implant. The body 654 can be continuously convex about at least a portion of the periphery 304 thereof. The body 654 can be round or can have an oblong form, such as being oval. A peripheral member 612 can be coupled with a portion of the periphery 304, e.g., to a superior portion. The body 604 can be symmetrical other than the presence of the peripheral member 612. The patient-specific glenoid guide 650 provides the advantage of easily being loaded upon the periphery pin 162 (or similar structure) by virtue of the enclosed channel 616 formed through the peripheral member 612. This loading can be outside of an incision providing access to the patient, which can facilitate a small incision. The configuration of the periphery 304 provide protection to the glenoid 54 by covering most or all of the portion of the glenoid 54 to be engaged to an implant.

Methods of use of the patient-specific glenoid guides 600, 650 are explained in more detail below in Section III.

D. Patient Matched Glenoid Guides with Peripheral Extensions for Enhanced Stability FIGS. 31-41B illustrate embodiments of glenoid guides that have outriggers or other projections that extend from portions configured to overlay the glenoid 54 to locations at the periphery of or outside of the glenoid 54.

Figure 22:
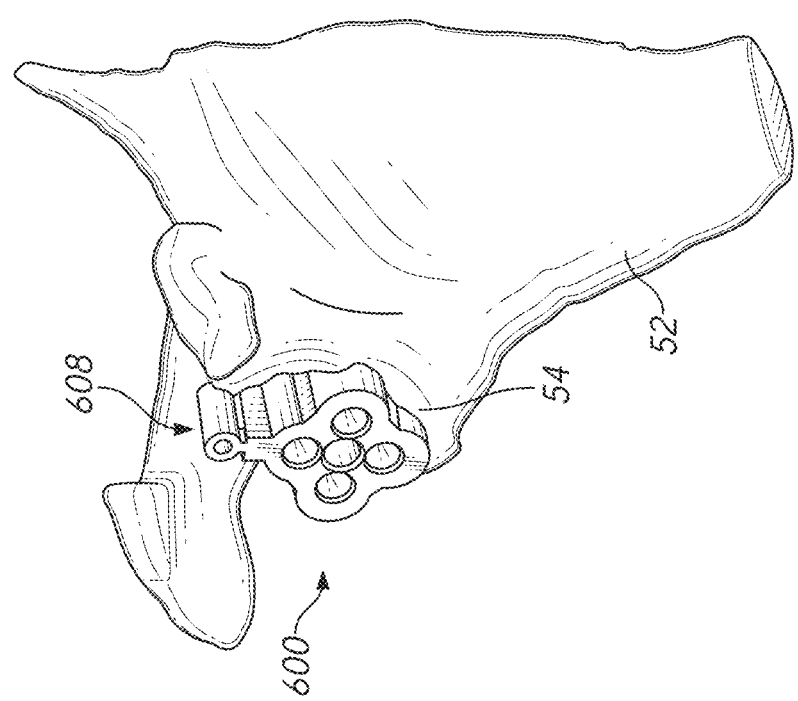
Figure 25:
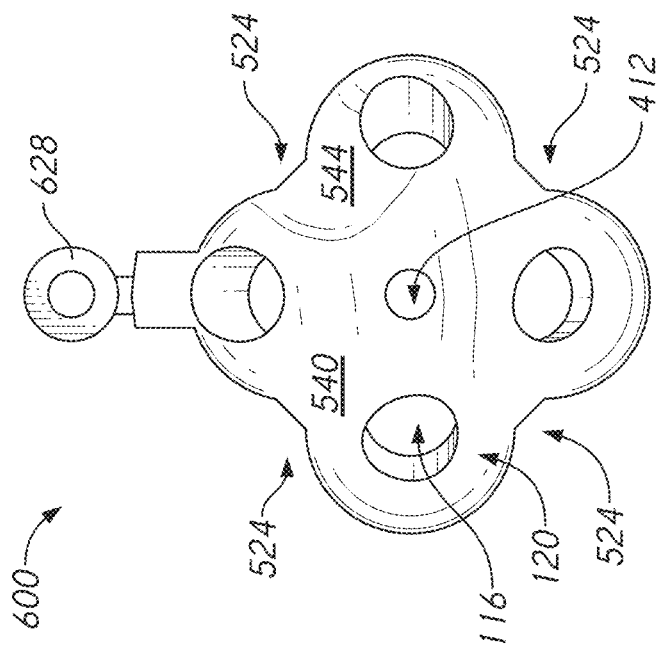
Figure 24:
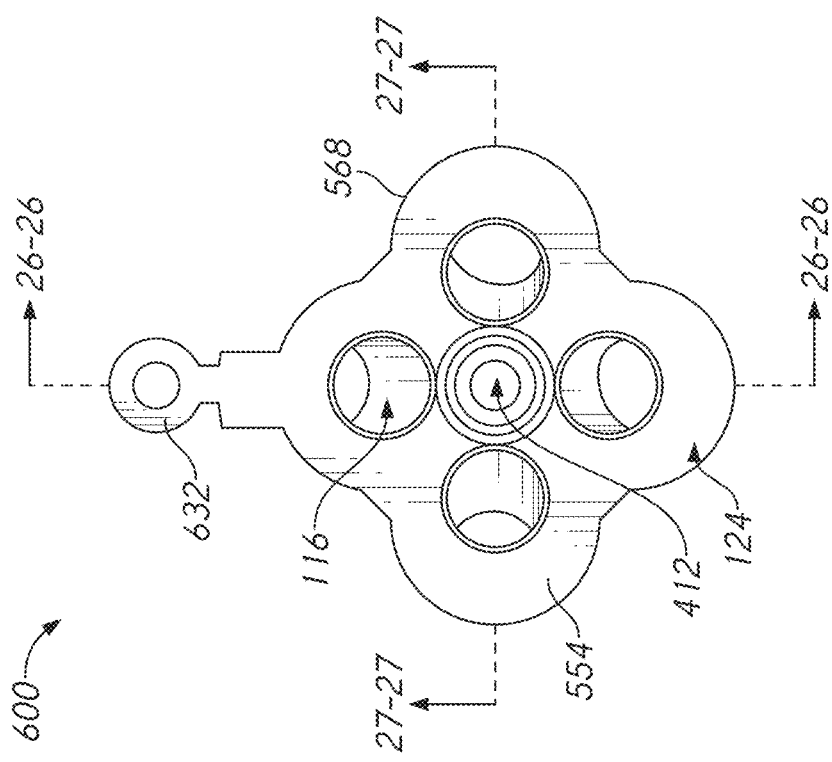
Figure 27:
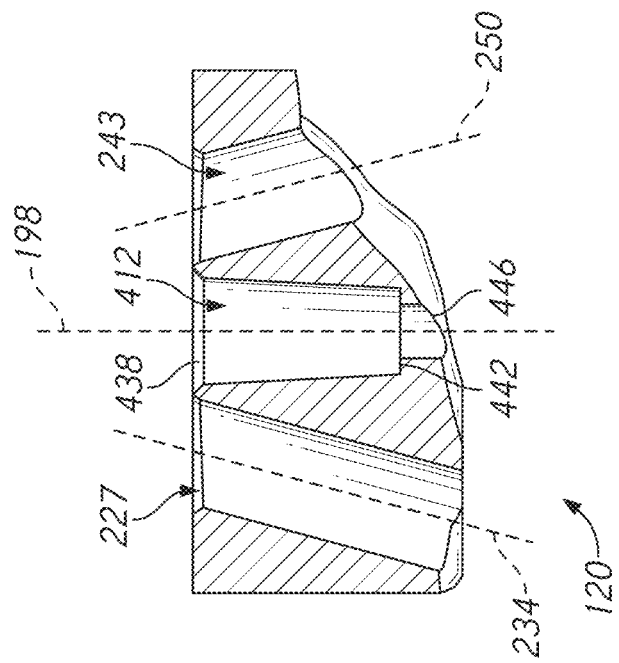

FIG. 31-35 show a patient-specific glenoid guide 700 that is similar in some ways to the patient-specific glenoid guide 550 of FIG. 21 and to the patient-specific glenoid guide 600 of FIG. 22, which description is considered to supplement the description of the patient-specific glenoid guide 700. The patient-specific glenoid guide 700 has a plurality of locating peripheral members that extend away from a body 704 thereof. The peripheral members can include a peripheral member 708 and a peripheral member 732. The peripheral member 708 can be a first peripheral member and the peripheral member 732 can be a second peripheral member. The peripheral member 732 can be offset from the peripheral member 708 by 90 degrees. In some embodiments, the peripheral member 708 and the peripheral member 732 are offset by other amounts, e.g., between 10 and 80 degrees, between baseplate 20 and 70 degrees, between 30 and 50 degrees, or about 45 degrees. There can be more than two peripheral members, e.g., three or four or more than four such members.

The peripheral member 708 can include a patient matched portion, such as a surface 716 configured as a negative of a surface of the scapula. The surface 716 configured can be as a negative of a surface of the scapula disposed away from an articular surface of the glenoid. The surface 716 can be formed as part of a contact member 724. The contact member 724 can be configured with an elongate member 720 having a first end coupled with a periphery of the glenoid guide 700 and a second end coupled with the patient matched contact member. The patient matched contact member can be cylindrical portion coupled with the second end of the elongate member 720 and extending toward the first side 120 to a medial position for contacting the glenoid 54.

The peripheral member 732 can a have a configuration similar to the peripheral member 708. The peripheral member 732 can have an elongate member 740 coupled at a first end to the periphery 560 of the body 704 and a second end coupled with a contact member 744. The contact member 744 can have a surface 716 that is patient matched to the bone adjacent to our outside of the periphery of the glenoid 54.

The peripheral member 708 can be configured to mate with a portion of the scapula 52 inferior to the glenoid 54. The peripheral member 732 can be configured to mate with a portion of the scapula 52 posterior to the glenoid 54. Other combinations of anatomy for mating the peripheral member 708 and the peripheral member 732 can be provided, e.g., any pair of surfaces of the scapula 52 offset by 90 degrees in the illustrated embodiment or by other offsets ad discussed above.

Figure 36:
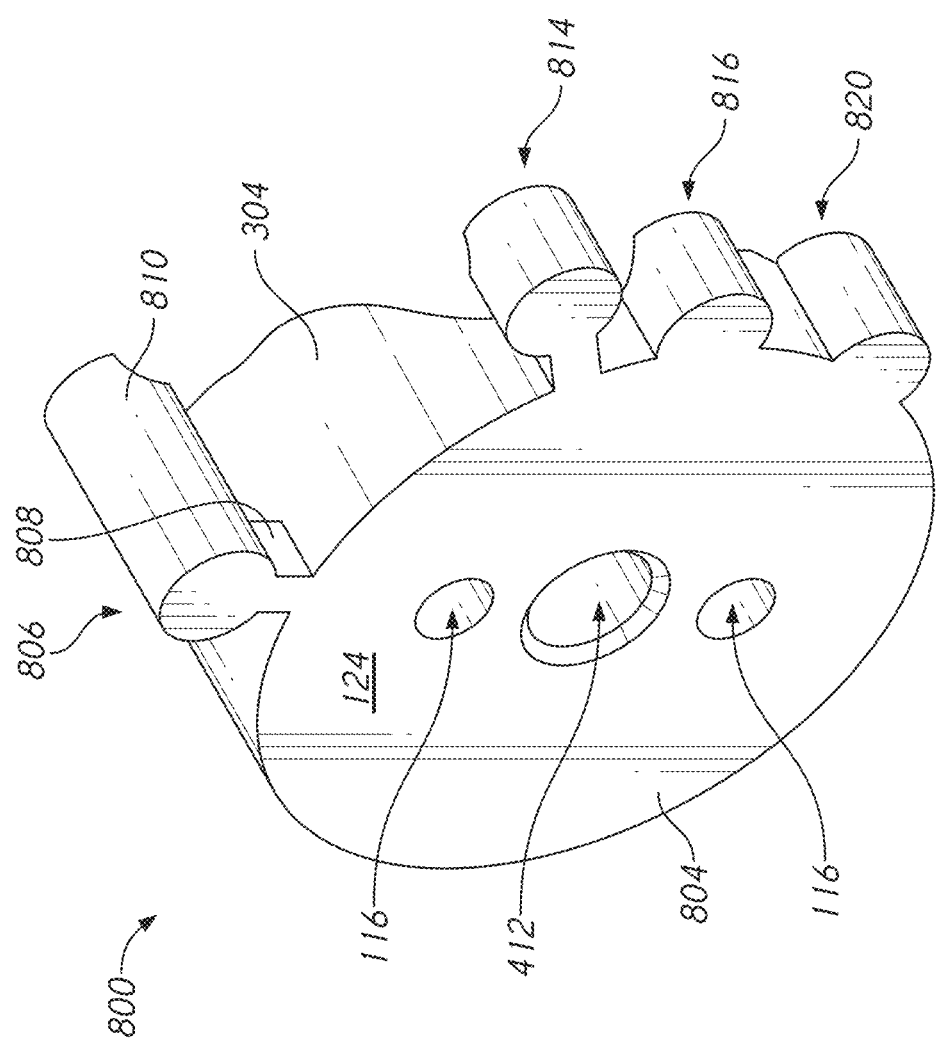
FIGS. 36-38 illustrate another embodiment of a patient specific glenoid guide.
Figure 38:
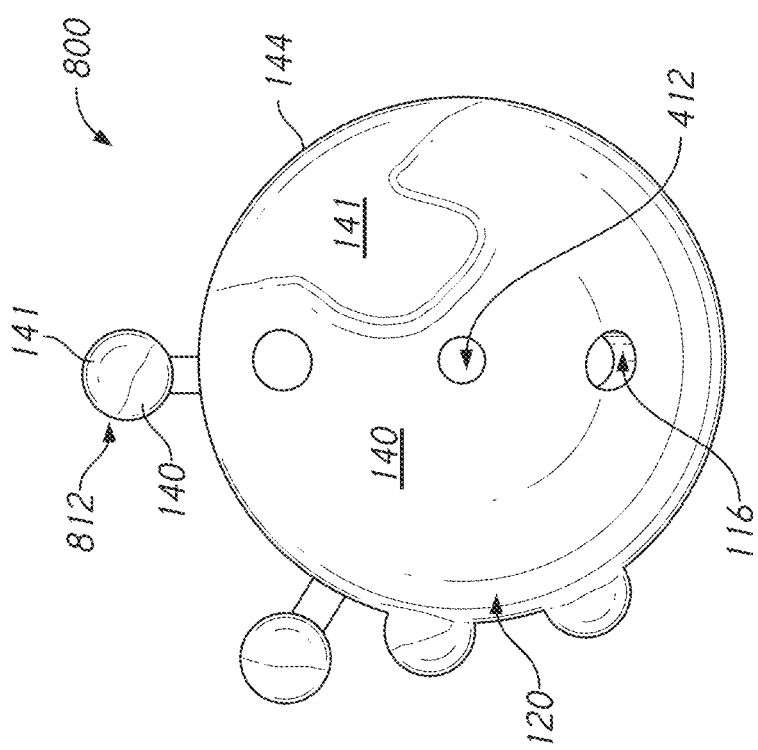
Figure 37:
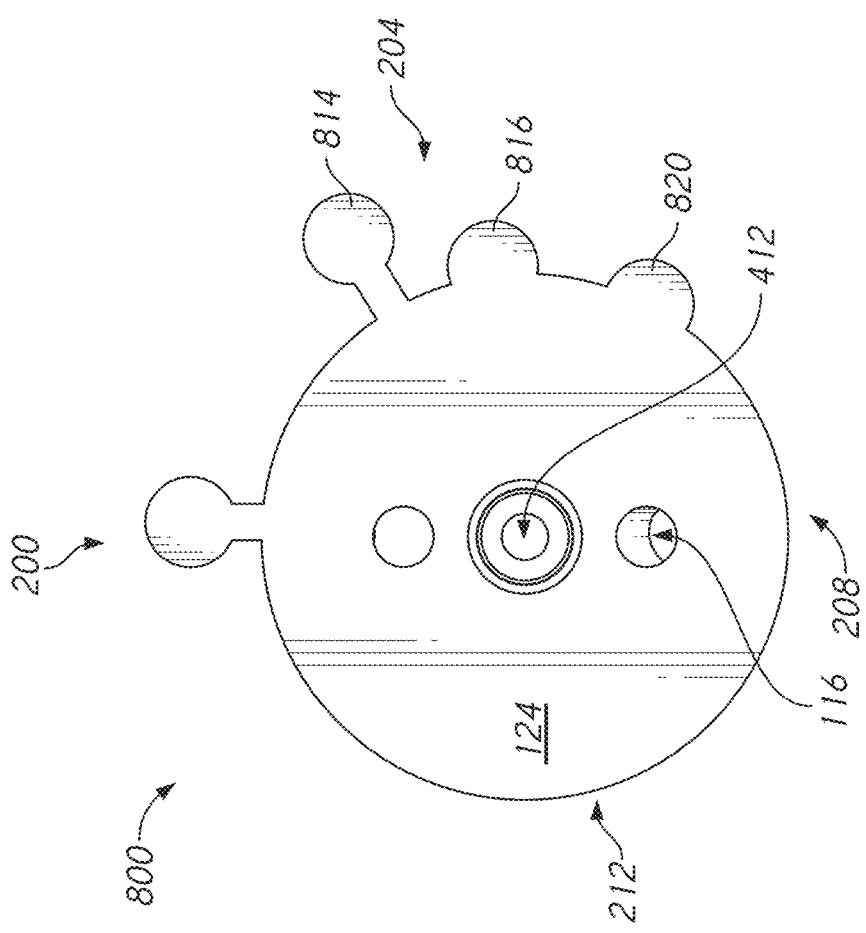

FIGS. 36-38 illustrate a patient-specific glenoid guide 800 that is similar to the patient-specific glenoid guide 100, the patient-specific glenoid guide 300, and the patient-specific glenoid guide 650. The description of these guides can supplement the description of the patient-specific glenoid guide 800 to provide a variety of further variations and descriptions.

The patient-specific glenoid guide 800 includes a body 804 and a plurality of peripheral members. A first peripheral member 806 is provided in a superior position of the body 804. The first peripheral member 806 can be configured to mate with bone in a region of the scapula 52 that is superior in the glenoid region thereof or that is at the rim of or superior to the glenoid 54. The first peripheral member 806 can include an elongate member 808 and a transverse portion 810. The transverse portion 810 extends transverse to the elongate member 808. The transverse portion 810 includes a contact portion that can be patient matched. The body 804 has on a first side 120 thereof a patient matched portion 140 and a non-contoured portion 141 in one embodiment. The transverse portion 810 also can have a patient matched portion 140 and a non-contoured portion 141 on a first side thereof, as shown in FIG. 38. The transverse portion 810 of the first peripheral member 806 can be spaced apart from the periphery 144 of the body 804 by the elongate member 808.

The patient-specific glenoid guide 800 can include a second peripheral member 814 that is spaced apart from the first peripheral member 806. The second peripheral member 814 can include a structure similar to that of the first peripheral member 806. The spacing between the first peripheral member 806 and the second peripheral member 814 can be selected by the surgeon based on an analysis of the bone of the patient in and around or outside of the glenoid 54. The spacing can cause the second peripheral member 814 to be located in an anterior portion of the guide as shown but can also cause the second peripheral member 814 to be in a posterior region thereof.

The patient-specific glenoid guide 800 can also include one or more peripheral members comprising bone contact member that extend directly from the periphery 144 of the body 804. The patient-specific glenoid guide 800 can include a third peripheral member 816 and a fourth peripheral member 820. The third peripheral member 816 and the fourth peripheral member 820 can each comprise a convex projection disposed on the periphery 144 of the patient-specific glenoid guide 800. The third peripheral member 816 and the fourth peripheral member 820 can each comprise semi-circular peripheries. The semicircular periphery of the third peripheral member 816 can start and end at the periphery 144. The semicircular periphery of the fourth peripheral member 820 can start and end at the periphery 144. The presence of absence of the elongate member 808 can be determined by how close the periphery 144 is to the edge of or the rim of the glenoid 54. The elongate member 808 can be added to span a gap between the periphery 144 and a location of the rim of the glenoid 54 for example. If the periphery 144 is configured to nearly overlay or cover the rim of the glenoid 54 or other feature of the scapula 52 then the elongate member 808 may be omitted.

In the illustrated embodiment all of the peripheral members are between a superior location and an inferior location on an anterior side of the body 804. In other embodiments, one or more of the peripheral members of the body 804 are on a posterior side of the glenoid guide 800.

FIGS. 39A-39F and 40A-40B illustrate patient-specific glenoid guides 900, 1000 that are similar to and may include any of the features of the above-described glenoid guides. The description of the above-described guides can supplement the description of the patient-specific glenoid guides 900, 900A, 1000 to provide a variety of further variations and descriptions. The glenoid guides 900, 900A, 1000 provides a single guide for guide pin placement, rotational alignment and proper seating of the baseplate 20, and visualization of at least a portion of the footprint of the baseplate 20. Providing these features in the glenoid guides 900, 900A, 1000 allows a clinician to evaluate any corrections that may be needed, for example to the version, inclination, or medialization. The use of a single guide to perform these functions eliminates the need for additional guides and instrumentation, which streamlines the surgical technique and reduces total surgical cost.

Figure 39B:
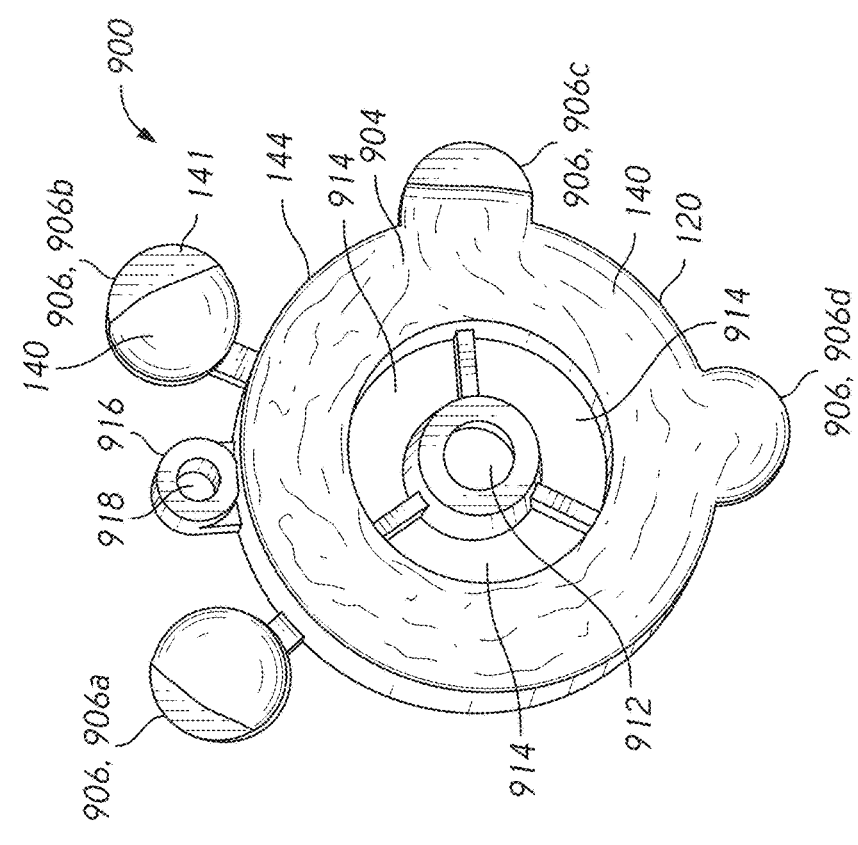
FIGS. 39A-39B illustrate another embodiment of a patient specific glenoid guide.
Figure 39A:
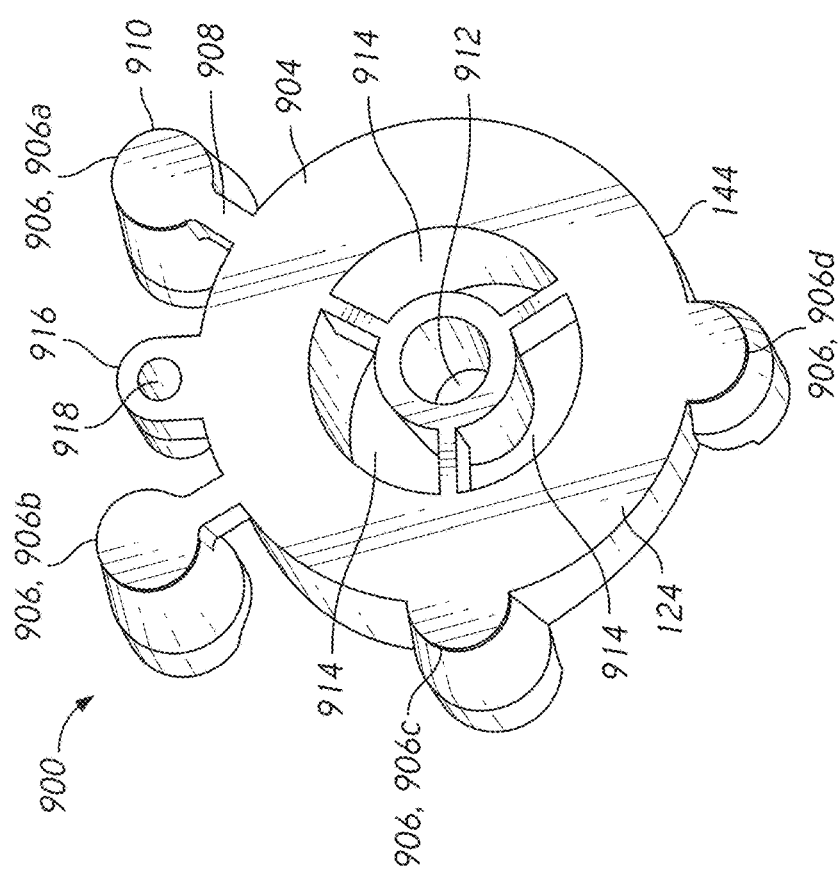
Figure 39D:
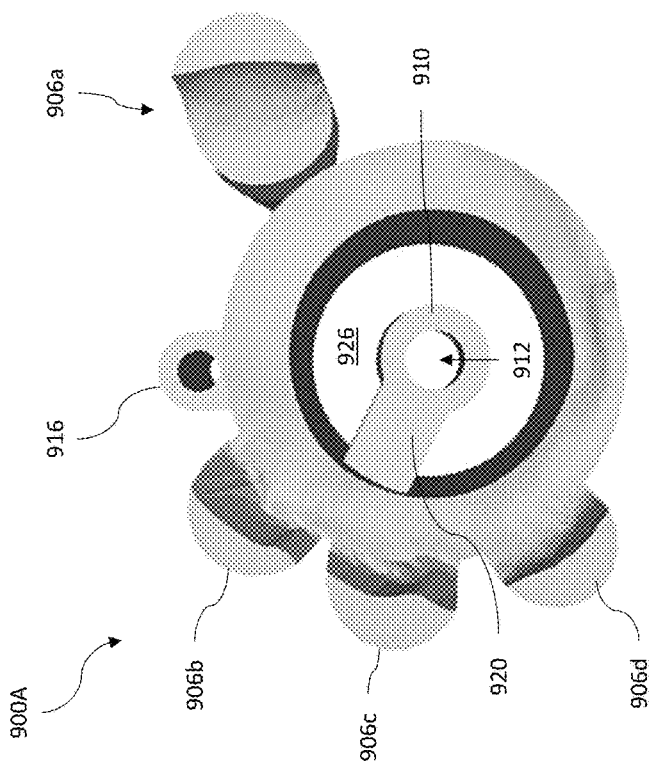
FIGS. 39C-39F illustrate another embodiment of a patient specific glenoid guide.
Figure 39C:
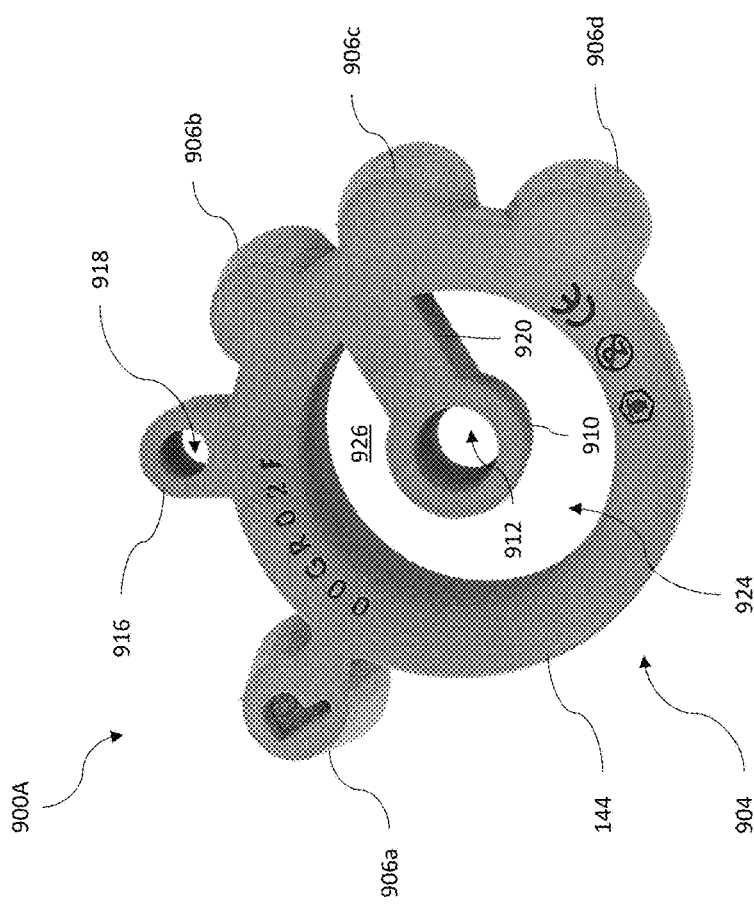

As shown in FIGS. 39A-39B, the patient-specific glenoid guide 900 includes a body 904 and a plurality of peripheral members 906. The body 904 has on a first side 120 thereof a patient matched portion 140 and/or a non-contoured portion 141 to provide an augmented body 904. The outer periphery 144 of the body 904 may correspond to the periphery size and shape of the baseplate 20 or another glenoid implant. For some patients, the body 904 may be augmented such that a first portion of the body 904 has a greater thickness than a second portion of the body 904. The body 904 allows the clinician to visualize the amount of correction to be applied to the glenoid by the glenoid implant. Since the first side 120 includes the patient matched portion 140, the clinician can properly locate the position and orientation of the glenoid guide 900 on the glenoid in a repeatable, predictable, and pre-operatively planned manner, as detailed below in Section III, and assess the seating of the baseplate 20 or other glenoid implant to be implanted prior to preparing the bone for fixation. After the glenoid guide 900 is properly seated, the guide pin may be placed as described below. In a modified embodiment, a portion of the first side 120 may include a non-patient matched portion when the body 904 exceeds the periphery size or shape of the baseplate 20 or another glenoid implant. For example, the non-patient matched portion may overhang the bone. In another embodiment at least a portion of the body 904 including the first side 120 may be separately attached to the plurality of peripheral members 906 or the remainder of the glenoid guide 900 to form a modular guide. In some implementations, the body 904 may be separately attached to the peripheral members 906, for example with a mechanical connection such as a friction fit, snap fit, threaded connection, or otherwise.

The body 904 includes a channel 912 formed in the body 902 that is adapted to receive a guide pin and/or a pin guide. The guide pin provides for cannulated drilling of an anchor hole. The channel 912 extends from a channel entrance disposed on a lateral or second side 124 of the glenoid guide 900 to a channel exit disposed on a medial or first side 120 of the glenoid guide 900. The channel 912 may be centrally positioned within the body 904. The channel 912 controls a position and axis of the guide pin and may be patient-matched. For example, the orientation of the channel 912 can be provided according to a surgical plan to be in a pre-selected orientation when the patient matched portion 140 is properly seated in, on or around the glenoid.

The body 904 may also include one or more open spaces 914 extending from the first side 120 to the second side 124 of the body 904 to provide visualization of the underlying bone. Reducing the amount of material in the body 904 may also reduce manufacturing costs. The open spaces 914 may include peripheral channels 116 for preparation of anchor channels as described above and/or the open spaces 914 may be distinct from, e.g., much larger than, the peripheral channels 116 to provide visualization by the unaided eye of a surgeon. The open spaces 914 are positioned radially between the channel 912 and an outer periphery 144 of the body 904. In the illustrated embodiment a plurality of open spaces 914 are provided between spokes extending between the ring member defining the guide channel 912 and the remainder of the body. The open spaces 914 can be located closer an inner periphery disposed about the channel 912 than to the outer periphery 144. While a plurality of, e.g., three, open spaces can be provided, more or less open spaces can be provided in other embodiments. In the illustrated embodiment three symmetrically positioned spaces 914 are provided. Three asymmetrically positioned spaces could be provided. Four, five, or six symmetrically or asymmetrically positioned spaces could be provided. In other embodiments a single space 914 can be provided where such space provides sufficient visibility to the glenoid surface in the use of the glenoid guide 900 as so configured. One such example is a glenoid guide 900A shown in FIGS. 39C-39F and discussed further below.

The patient-specific glenoid guide 900 can have a locating feature 916 at or extending from a periphery 144 of the body 904. The locating feature 916 can be located at any portion of the periphery 144. In the illustrated embodiment, the locating feature 916 can be located at between the posterior portion and the superior portion of, e.g., at a generally superior portion of, the glenoid guide 900. In other embodiments, the locating feature 916 is disposed at an anterior portion, an inferior portion, a posterior portion, or at any location between these portions of the glenoid guide 900.

The locating feature 916 can include a peripheral member 906 that extends from the periphery 144. The locating feature 916 can include a channel 918, such as an enclosed channel, sized to create a locator such as an implant rotational alignment mark or a peripheral pin. The locating feature 916 can allow a pin to pass through the locating feature 916 at a peripheral position of the guide 900 to provide a reference position for the proper rotational position of the baseplate 20 or another glenoid implant. Also, in some embodiments a pin disposed through the locating feature can enable the guide 900 to be held in position on the glenoid rotationally during use of the guide.

As discussed above, the patient-specific guide includes a plurality of peripheral members 906. One or more of the peripheral members 906 may include a patient matched portion 140 configured to conform to the rim or a portion of the glenoid. The plurality of peripheral members 906 may have different shapes and/or extend at different lengths from the body 904. This can enable the different peripheral members 906 to rest on the rim of the glenoid while positioning the channel 912 at any position of the glenoid surface, e.g., more inferiorly as appropriate for a specific patient.

At least a first peripheral member 906a is provided in a position of the body 904 that is aligned with a posterior portion of the glenoid when the guide is placed against the scapula. The first peripheral member 906a can be configured to conform to the rim of or a portion of the posterior side of the glenoid. The first peripheral member 906a can include an elongate member 908 and a transverse portion 910 (also referred to herein as a patient matched contact member) extending transverse or perpendicular to the elongate member 908. The transverse portion 910 may have a cylindrical configuration or portion. A first side of the transverse portion 910 may have a patient matched portion 140 and a non-contoured portion 141 on a first side thereof, as shown in FIG. 39B. The patient matched portion 140 of the transverse portion 910 facilitates proper rotational position of the glenoid guide 900, and thus the baseplate 20. The transverse portion 910 of the first peripheral member 906a can be spaced apart from the periphery 144 of the body 904 by the elongate member 908. The spacing allows the clinician to visualize the portion of the glenoid that will underlay the ultimate footprint of the baseplate 20 when the baseplate is implanted.

The patient-specific glenoid guide 900 can include at least a second peripheral member 906b that is spaced apart from the first peripheral member 906a. The second peripheral member 906b can include a structure similar to that of the first peripheral member 906a. The spacing between the first peripheral member 906a and the second peripheral member 906b can be selected by the surgeon based on an analysis of the bone of the patient in and around or outside of the glenoid. This analysis can be performed pre-operatively by viewing a CT-scan, MRI or other output of an imaging device. The spacing can cause the second peripheral member 906b to be located in an anterior portion, in a superior portion or between the superior portion and an anterior portion of the guide 900.

The patient-specific glenoid guide 900 can also include at least one peripheral member 906 disposed on the periphery 144 of the body 904. For example, the patient-specific glenoid guide 900 can include a third peripheral member 906c and a fourth peripheral member 906d. The third peripheral member 906c and the fourth peripheral member 906d can each comprise a convex projection disposed on the periphery 144 of the patient-specific glenoid guide 900. The third peripheral member 906c and the fourth peripheral member 906d can each comprise circular or semi-circular peripheries. The semi-circular periphery of the third peripheral member 906c and the fourth peripheral member 906d can start and end at the periphery 144. The third peripheral member 906c and/or the fourth peripheral member 906d may be located in the anterior portion, between the superior portion and the inferior portion of the patient-specific glenoid guide 900. Circular or semi-circular peripheral members can be located at any of the positions illustrated in FIGS. 39A-39B, e.g., including the posterior location of the peripheral member 906a. The presence or absence of the elongate member 908 can be determined by how close the periphery 144 is to the edge of or the rim of the glenoid. The elongate member 908 can be added to span a gap between the periphery 144 and a location of the rim of the glenoid for example. If the periphery 144 is configured to nearly overlay or cover the rim of the glenoid or other feature of the scapula, then the elongate member 908 may be omitted. In some cases the periphery 144 is configured to nearly overlay or cover the rim of the glenoid and the elongate member 908 is provided such that the contact between the guide 900 and the scapula may be spaced outward of the glenoid rim.

When the peripheral members 906 are properly seated at the rim or other portion of the glenoid or scapula, the first side 120 of the body 904 may be spaced apart, for example uniformly spaced apart, from the glenoid surface, for example by less than or equal to about 1.0 mm. In this configuration, the patient matched portion 140 of the first side 120 may not be needed to provide alignment of the guide. In some implementations, the glenoid is not reamed before using the guide 900, but as explained in more detail below in Section III, cartilage or labrum may be removed from the surface of the glenoid prior to advancing the implant. Excess soft tissue may prevent the glenoid implant from seating correctly. The patient matched portion 140 of the body 904 may be used to assess whether additional soft tissue may need to be removed. For example, if the patient matched portion 140 of the body 904 contacts the glenoid surface when the peripheral members 906 are properly seated at the rim or other portion of the glenoid, then additional soft tissue may need to be removed. If the patient matched portion 140 of the body 904 is spaced apart, for example uniformly spaced apart, from the glenoid surface when the peripheral members 906 are properly seated at the rim or other portion of the glenoid, then sufficient soft tissue may have been removed. After the patient-specific guide 900 is properly positioned, the guide 900 may be used to place a guide pin through the channel 912 and/or create an implant rotational alignment mark or place a periphery pin through the locating feature 916.

FIGS. 39C-39F show a patient-specific glenoid guide 900A that is similar to the guide 900 discussed above. The description of the guide 900 set forth above and elsewhere herein applies to the glenoid guide 900A except as described differently below. The glenoid guide 900A includes a body 904 having an outer periphery 144. The body 904 can be formed as an annulus extending from the outer periphery 144 to an inner periphery of the body 904. The glenoid guide 900A is provided with at least one, e.g., a plurality of peripheral contact features. The glenoid guide 900A can include at least one contact feature disposed on a posterior side of the glenoid guide 900A and at least one contact feature disposed on an anterior side of the glenoid guide 900A. In the illustrated embodiment, the glenoid guide 900A includes a first peripheral member 906a disposed on a posterior side of the glenoid guide 900A. The glenoid guide 900A includes a second peripheral member 906b, a third peripheral member 906c, and a fourth peripheral member 906d disposed on an anterior side of the first peripheral member 906a. In variations, one or more of the peripheral members 906a, 906b, 906c can be disposed on the posterior side of the glenoid guide 900A.

Figure 39F:
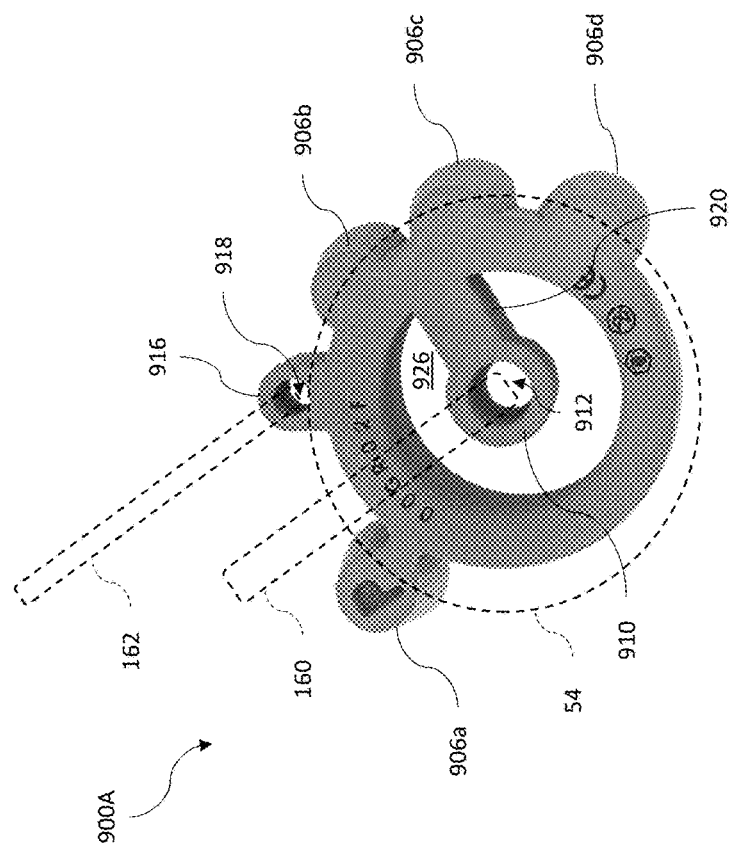
Figure 39E:
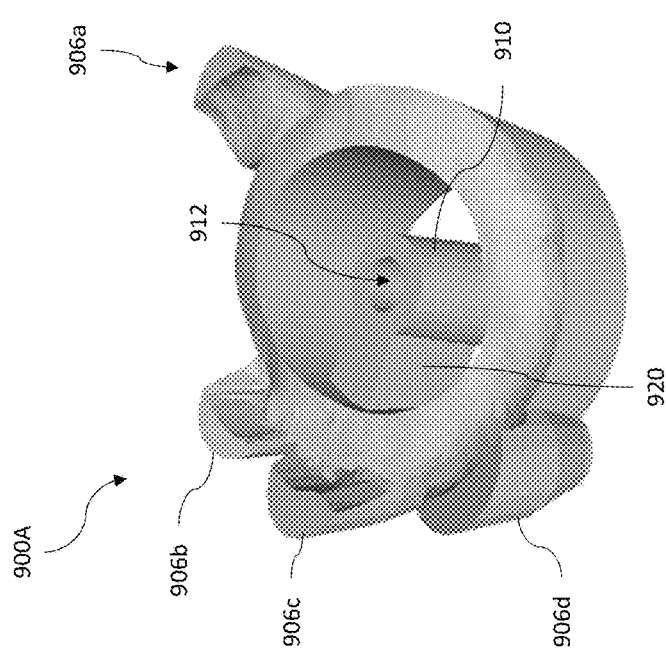

FIG. 39E shows that the peripheral members of the glenoid guide 900A can have a segment that is formed in a patient matched manner to engage specific segments of the glenoid of a particular patient. The first peripheral member 906a is shown in FIG. 39E as having a slope including a more vertical portion that is configured to rest on an outer surface of the glenoid rim to a more horizontal portion configured to rest on a top portion of the glenoid rim. The peripheral members 906b, 906c, 906d can be configured with a similar slope including vertical and horizontal portions. As such, one or more or all of the peripheral members 906a, 906b, 906c, 906d is or are formed to contact an outer side of the glenoid rim but also to rest on top of the glenoid rim.

The glenoid guide 900A can include a locating feature 916 disposed at the periphery thereof. The locating feature 916 can extend from any position of the outer periphery 144. In the illustrated embodiment, the locating feature 916 can be disposed between the first peripheral member 906a and one of the peripheral members on the anterior side of the glenoid guide 900A. For example, the locating feature 916 can be disposed between the first peripheral member 906a and the second peripheral member 906b. The locating feature 916 can be located between the fourth peripheral member 906d and the first peripheral member 906a. The locating feature 916 can be disposed among the peripheral members disposed on the anterior side of the glenoid guide 900A, e.g., between the second peripheral member 906b and the fourth peripheral member 906d. The locating feature 916 is illustrated as being disposed at a superior position of the glenoid guide 900A.

As has been discussed above, one or more of the first peripheral members 906a, 906b, 906c, 906d can be formed as convex projections (as viewed from the lateral side) extending directly from the outer periphery 144, as is the case in the second peripheral members 906b, 906c, 906d of the glenoid guide 900A or as discrete circular or complete convex portions connected to the outer periphery 144 by slender projections, as is seen in connection with the first peripheral member 906a. The extent to which the peripheral members extend directly from the outer periphery 144 or are coupled by a projection depends on the form of a particular patient's glenoid, which is analyzed to form the glenoid guide 900A, as has been discussed above in connection with other guides described herein.

The glenoid guide 900A includes a ring member 910 that is supported by a spoke 920. The spoke 920 extends from an inner surface of the annulus that extends between the outer periphery 144 and an inner periphery of the annulus. The ring member 910 surrounds the channel 912. FIG. 39E shows that the spoke 920 can be spaced away from projections of the medial sides of the peripheral members 906a, 906b, 906c, 906d. Thus, the spoke 920 and the ring member 910 can be spaced away from the glenoid and thereby not prevent the glenoid guide 900A from making the patient specific contact that the pre-operative planning intends to occur.

The glenoid guide 900A further includes a continuous circumferential space 924. This is an example of a glenoid guide with a single space 914, as discussed above. The continuous circumferential space 924 can extend more than 120 degrees between opposing spoke surfaces, e.g., between opposing sides of the spoke 920. The continuous circumferential space 924 that extends more than 120 degrees about the channel 912 could extend between two spokes that are spaced circumferentially apart from each other by that extent. The continuous circumferential space 924 can extend more than 150 degrees between opposing spoke surfaces of the same or different spokes. The continuous circumferential space 924 can extend more than 180 degrees between opposing spoke surfaces. The continuous circumferential space 924 can extend more than 210 degrees between opposing spoke surfaces. The continuous circumferential space 924 can extend more than 240 degrees between opposing spoke surfaces of the same or different spokes. The continuous circumferential space 924 can extend more than 270 degrees between opposing spoke surfaces. The continuous circumferential space 924 can extend more than 330 degrees between opposing spoke surfaces. The continuous circumferential space 924 can extend about 350 degrees from opposing sides of the single spoke 920.

The continuous circumferential space 924 can be configured as a C-shaped opening 926 disposed between the annulus or ring member 910 surrounding the channel 912 and the annulus or ring member of the body 904 disposed between the outer periphery 144 and the inner periphery thereof.

FIG. 39F shows schematically the use of the glenoid guide 900A. The glenoid guide 900A is placed in contact with the glenoid 54. The rim of the glenoid 54 nests into the concave surfaces of the first peripheral member 906a on the posterior side and the concave surfaces of the second peripheral member 906b, the third peripheral member 906c, and the fourth peripheral member 906d. While the peripheral members provide great fit in a pre-operatively defined position, the body 904 disposed inward of the peripheral members provides good confirmation of fit of the glenoid guide 900. The annulus of the body 904 is seen in FIG. 39E to have a patient matched surface that is pre-operatively designed to have a negative surface of the glenoid 54 inward of the rim of the glenoid 54. The glenoid guide 900A provides fit on to the glenoid 54 at the peripheral members. The glenoid guide 900A also provides a confirmation that the glenoid has been properly prepared, e.g., by sufficient removal of the cartilage thereon, by the annulus of the body 904 resting firmly on the portion of the glenoid 54 to which the body 904 was pre-operatively configured to mate. The surgeon will be signaled of incomplete soft tissue (e.g., labrum and cartilage) removal if the body 904 of the glenoid guide 900A does not stably rest on the glenoid 54. Should a surgeon proceed with next steps of the surgery without having removed the soft tissue, the orientation of a guide pin for guiding a reamer or other instrument could result in the implant not being placed according to the preoperative plan. This could result to sub-optimal results and even in some cases a revision surgery. Many patients are elderly and may not be able to undergo revision surgery. So the confirmation provided by the glenoid guide 900A (and the other guides disclosed herein) is extremely advantageous in enhancing the quality of outcomes and also gives the surgeon confidence in proceeding through the procedure. The continuous circumferential space 924 is almost unobstructed by support for the ring member 910. The continuous circumferential space 924 is only limited by the thin circumferential dimension of the spoke 920, enabling nearly 360 degree view of the glenoid between the ring member 910 and the annulus inward of the outer periphery 144 of the body 904.

Figure 14:
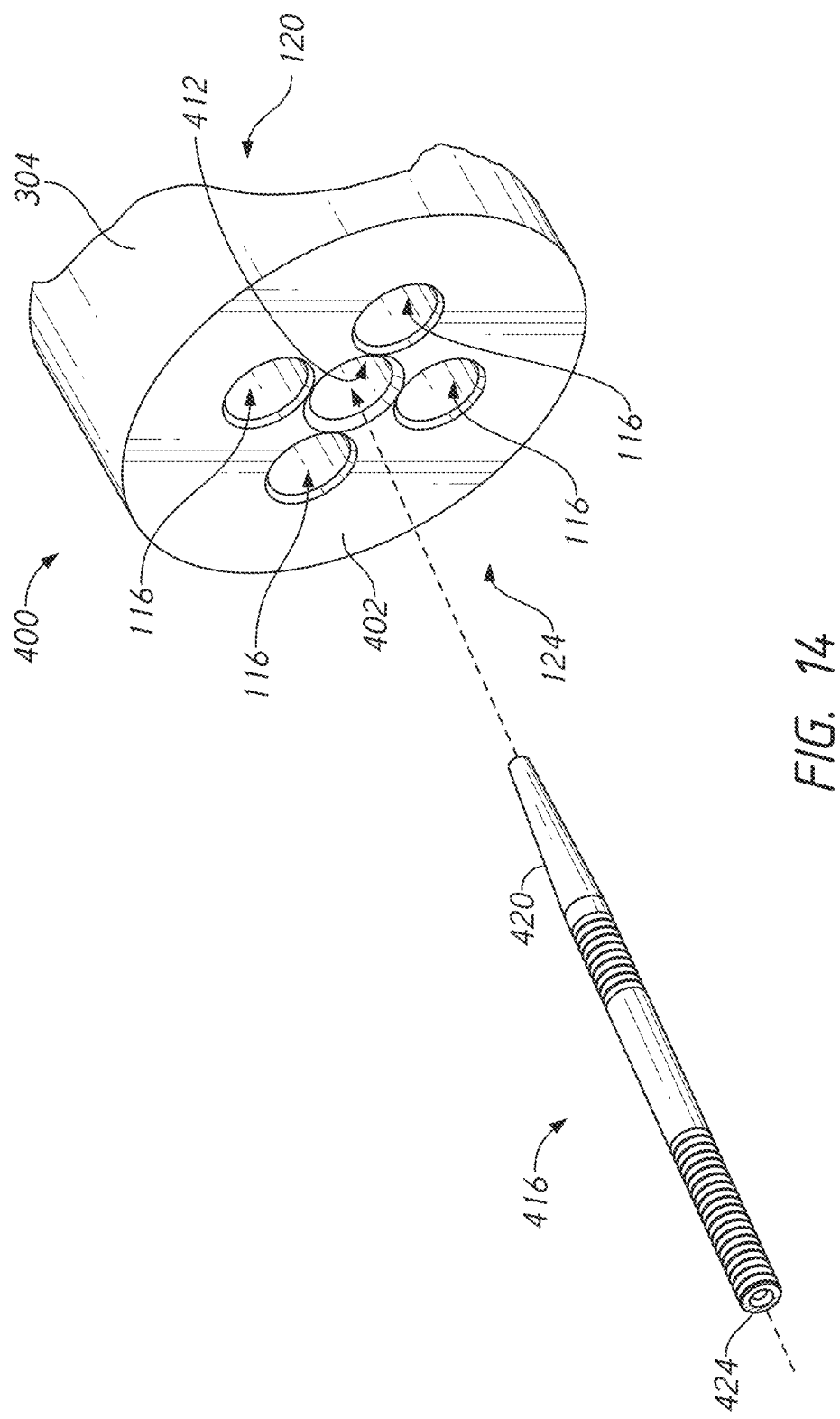
FIGS. 14-17 illustrate another embodiment of a patient specific glenoid guide.
Figure 15:
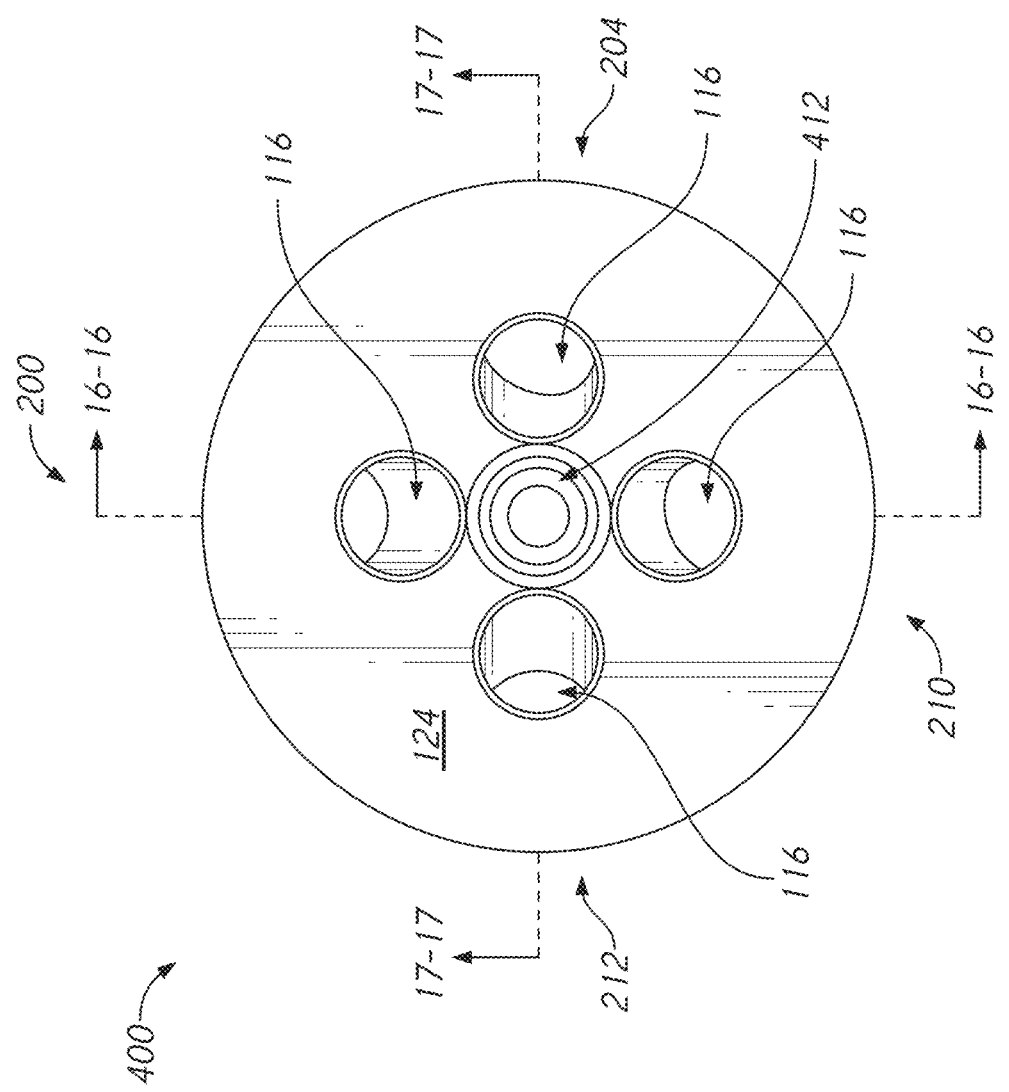

Once the glenoid guide 900A is stable positioned properly using the peripheral members 906a, 906b, 906c, 906d and the body 904, the periphery pin 162 can be placed with reference to the locating feature 916, e.g., through the channel 918 or alternatively in a concave channel in the outer periphery 144. The central guide pin 160 can be placed through the channel 912. The central guide pin 160 can be advanced directly through the ring member 910 or can be passed through a tubular pin guide 416 (as seen in FIG. 14) to be positioned in the ring member 910. The inner periphery of the ring member 910 can be formed as a right cylinder for direct advancement of the central guide pin 160. The inner periphery of the ring member 910 can be formed as a distally tapered surface for nesting the pin guide 416 (see FIG. 14) in the ring member 910. The inner periphery of the ring member 910 can be formed as a distally tapered surface for controlling the advancement of the central guide pin 160 directly through the ring member 910, e.g., the central guide pin 160 can be advanced through the ring member 910 until the outer surface of the central guide pin 160 contacts the narrowest part of the tapered inner surface of the ring member 910. Once the central guide pin 160 is placed, the glenoid guide 900A can be removed and the central guide pin 160 can be used to control placement of other instruments, reaming if performed and augmented baseplate placement if used.

Figures 40A, 40B:
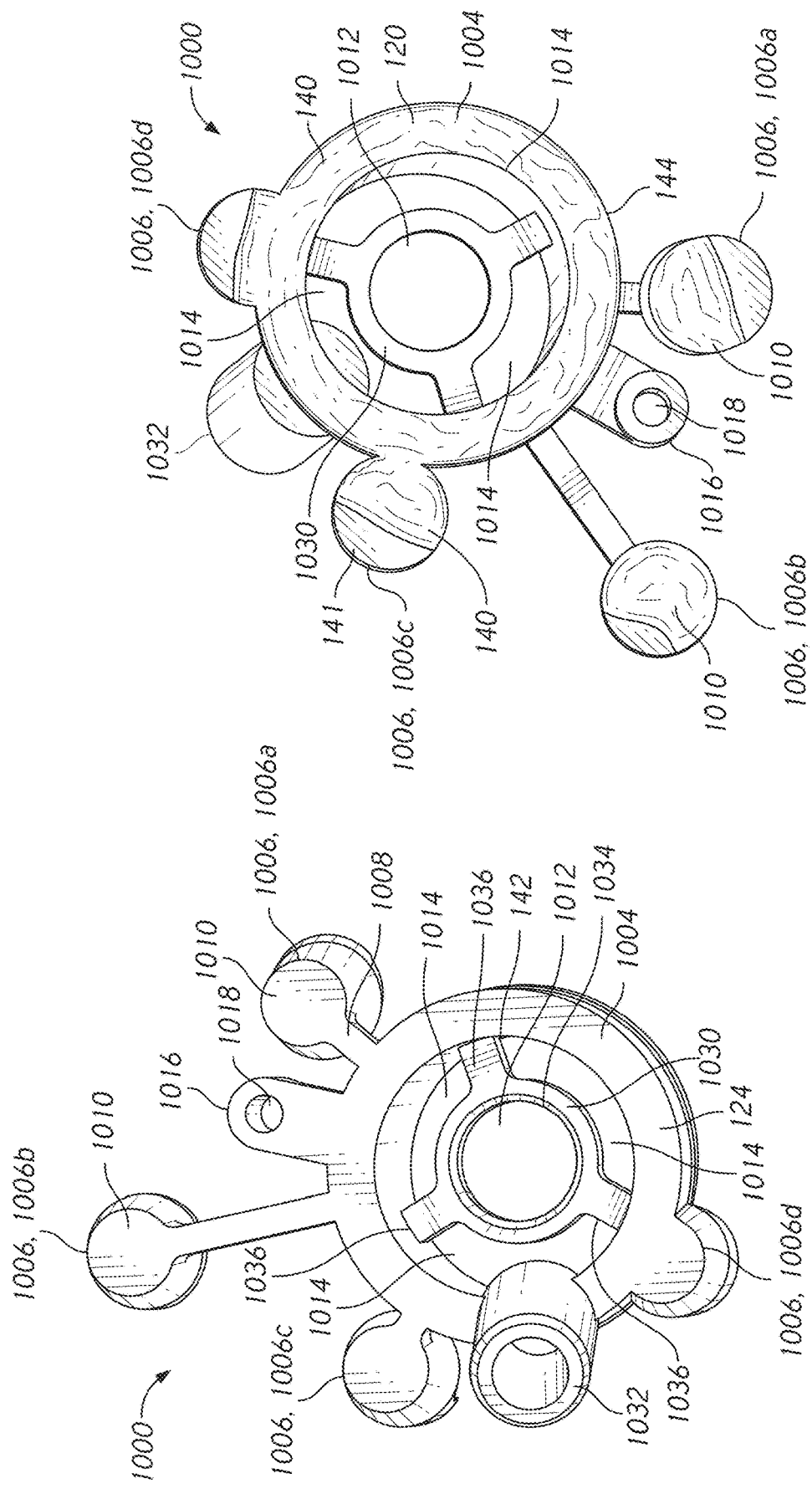
FIGS. 40A-40B illustrate another embodiment of a patient specific glenoid guide.

FIGS. 40A-40B illustrate a patient-specific glenoid guide 1000. The patient-specific glenoid guide 1000 includes a body 1004 and a plurality of peripheral members 1006. The body 1004 has on a first side 120 thereof a patient matched portion 140 and/or a non-contoured portion 141 to provide an augmented body 1004. The outer periphery 144 of the body 1004 may correspond to the periphery size and shape of the baseplate 20 or another glenoid implant. For some patients, the body 1004 may be augmented such that a first portion of the body 1004 has a greater thickness than a second portion of the body 1004. The body 1004 allows the clinician to visualize the amount of correction to be applied to the glenoid by the glenoid implant. Since the first side 120 includes the patient matched portion 140, the clinician can properly locate the position and orientation of the glenoid guide 1000 on the glenoid in a repeatable, predictable, and pre-operatively planned manner, as detailed below in Section III, and assess the seating of the baseplate 20 or other glenoid implant to be implanted prior to preparing the bone for fixation. After the glenoid guide 1000 is properly seated, the anchor hole may be drilled as described below. In a modified embodiment, a portion of the first side 120 may include a non-patient matched portion when the body 1004 exceeds the periphery size or shape of the baseplate 20 or another glenoid implant. For example, the non-patient matched portion may overhang the bone. In another embodiment at least a portion of the body 1004 including the first side 120 may be separately attached to the plurality of peripheral members 1006 or the remainder of the glenoid guide 1000 to form a modular guide. In some implementations, the body 1004 may be separately attached to the peripheral members 1006, for example with a mechanical connection such as a friction fit, snap fit, threaded connection, or otherwise.

The body 1004 includes a channel 1012 formed in the body 1002 that may be adapted to receive instrumentation for preparing the glenoid or a bushing for receiving a guide pin to control a position and axis of a guide pin or guide wire. The channel 1012 extends from a channel entrance disposed on a lateral or second side 124 of the glenoid guide 1000 to a channel exit disposed on a medial or first side 120 of the glenoid guide 1000. The channel 1012 may be centrally positioned within the body 1004.

The channel 1012 may be sized to directly receive a drill, for example without the use of a pin guide, to create an anchor channel for a central fixation element. The channel 1012 may include a central cannula that acts as a drill stop for the drill. In the embodiment depicted in FIGS. 40A and 40B the cannula includes a ring member 1030 that is held within an inner periphery 142 of the body 1004. The ring member 1030 has an inner periphery 1034 that has a diameter that approximately matches the size of an anchor peg of the baseplate 20. Accordingly, the inner periphery 1034 can be just large enough to receive a bit or other hole forming implement to guide the bit or implement into the glenoid when the guide 1000 is properly seated. The location of the ring 1030 within the inner periphery 142 of the body 1004 can be determined on a patient specific basis. For example, the ring member 1030 can be closer to a posterior edge of the periphery 142 of the body 1002 if the position of the peg is to be offset from a centered position. The ring member 1030 can be closer to the anterior of the periphery 142 of the body 1002 in some cases. The ring member 1030 can be closer to a superior aspect of the periphery 142 of the body 1002 in some cases. The ring member 1030 can be closer to an inferior aspect of the periphery 142 of the body 1002 in some cases. The ring member 1030 can be supported in any suitable manner. In the illustrated embodiment a plurality of spokes is provided between the body 1002 and the ring member 1030 to support the ring member. A height of the central cannula 1030 may be patient-matched to control a position of the drill, e.g. a depth to which a bit or other implement can be advanced. For example, the medial lateral location of the spokes 1036 or the ring member 1030 can be set in a patient specific manner to control the depth of the bit or implement forming the hole. The spokes 1036 and/or the ring member 1030 can be recessed a distance from the second side 124 of the body 1004. The drill will thus be able to be advanced only until it contacts the lateral side of the spokes 1036 or of the ring member 1030. Although the spokes 1036 or ring 1030 may be recessed, in some cases, these structures may be extended in a direction opposite to the recessed direction, e.g., may project or extend laterally of the second side 124 to further limit the extent of the depth of any holes formed through the channel 1012 or otherwise through the guide 1000. After the guide 1000 has been properly seated, a central anchor hole and/or an implant rotational alignment mark can be drilled. The drilling depth can be controlled as discussed above in a patient specific manner by the configuration of the guide 1000 (or any of the other guides disclosed herein as modified with a recessed or projection drill stop to provide such control). Although the guide 1000 may directly receive the drill, as explained above, a bushing may be provided to the channel 1012 for a guide pin if cannulated drilling is preferred.

The body 1004 may also include one or more open spaces 1014 extending from the first side 120 to the second side 124 of the body 1004 to provide visualization of the underlying bone. Reducing the amount of material in the body 904 may also reduce manufacturing costs. The open spaces 1014 may include peripheral channels 116 for preparation of anchor channels as described above and/or the open spaces 1014 may be distinct from the peripheral channels 116 and simply provide visualization. The open spaces 1014 are positioned radially between the channel 1012 and the outer periphery 144 of the body 1004.

The patient-specific glenoid guide 1000 also can have a locating feature 1016 at or extending from a periphery 144 of the body 1004. The locating feature 1016 can be located at any portion of the periphery 144. In the illustrated embodiment the locating feature 1016 can be located at the superior portion or between the anterior portion and the superior portion of the body 1004. In other embodiments, the locating feature 1016 is disposed at the posterior portion, the inferior portion, or the anterior portion.

The locating feature 1016 can include a peripheral member 1006 that extends from the periphery 144. The locating feature 1016 can include a channel, such as an enclosed channel 1018, sized to create a locator such as an implant rotational alignment mark or allow a periphery pin to pass through to provide a reference position for the proper rotational position of the baseplate 20 or another glenoid implant.

As discussed above, the patient-specific guide includes a plurality of peripheral members 1006. One or more of the peripheral members 1006 may include a patient matched portion 140 configured to conform to the rim or a portion of the glenoid. The plurality of peripheral members 1006 may have different shapes and/or extend at different lengths from the body 1004.

At least a first peripheral member 1006a is provided in a posterior position of the body 1004 when implanted. The first peripheral member 1006a can be configured to conform to the rim of or a portion of the posterior side of the glenoid. The first peripheral member 1006a can include an elongate member 1008 and a transverse portion 1010 (also referred to herein as a patient matched contact member) extending transverse or perpendicular to the elongate member 1008. The transverse portion 1010 may have a cylindrical portion. The transverse portion 1010 may include a patient matched portion 140 and/or a non-contoured portion 141 on a first side thereof, as shown in FIG. 40B. The patient matched portion 140 of the transverse portion 1010 facilitates proper rotational position of the glenoid guide 1000, and thus the baseplate 20. The transverse portion 1010 of the first peripheral member 1006a can be spaced apart from the periphery 144 of the body 1004 by the elongate member 1008. The spacing allows the clinician to visualize the ultimate footprint of the baseplate 20.

The patient-specific glenoid guide 1000 can include at least a second peripheral member 1006b that is spaced apart from the first peripheral member 1006a. The second peripheral member 1006b can include a structure similar to that of the first peripheral member 1006a. The spacing between the first peripheral member 1006a and the second peripheral member 1006b can be selected by the surgeon based on an analysis of the bone of the patient in and around or outside of the glenoid. The spacing can cause the second peripheral member 1006b to be located in the anterior portion or between the superior portion and the anterior portion of the guide 1000 as shown.

The patient-specific glenoid guide 1000 can also include at least one peripheral member 1006 that is disposed at the periphery 144 of the body 1004. For example, the patient-specific glenoid guide 1000 can include a third peripheral member 1006c and a fourth peripheral member 1006d. The third peripheral member 1006c and the fourth peripheral member 1006d can each comprise a convex projection disposed on the periphery 144 of the patient-specific glenoid guide 1000. The third peripheral member 1006c and the fourth peripheral member 1006d can each comprise semicircular peripheries. The semicircular periphery of the third peripheral member 1006c and the fourth peripheral member 1006d can start and end at the periphery 144. The third peripheral member 1006c and/or the fourth peripheral member 1006d may be located in the anterior portion, between the superior portion and the inferior portion anterior portion of the patient-specific glenoid guide 900. The presence or absence of the elongate member 1008 can be determined by how close the periphery 144 is to the edge of or the rim of the glenoid. The elongate member 1008 can be added to span a gap between the periphery 144 and a location of the rim of the glenoid for example. If the periphery 144 is configured to nearly overlay or cover the rim of the glenoid or other feature of the scapula then the elongate member 1008 may be omitted.

When the peripheral members 1006 are properly seated at the rim or other portion of the glenoid, the first side 120 of the body 1004 may be spaced apart, for example uniformly spaced apart, from the glenoid surface, for example by less than or equal to about 1.0 mm. In this configuration, the patient matched portion 140 of the first side 120 may not be needed to provide alignment of the guide. In some implementations, the glenoid is not reamed before using the guide 1000, but as explained in more detail below in Section III, cartilage or labrum may be removed from the surface of the glenoid prior to advancing the implant. Excess soft tissue may prevent the glenoid implant from seating correctly. The patient matched portion 140 of the body 1004 may be used to assess whether additional soft tissue may need to be removed. For example, if the patient matched portion 140 of the body 1004 contacts the glenoid surface when the peripheral members 1006 are properly seated at the rim or other portion of the glenoid, then additional soft tissue may need to be removed. If the patient matched portion 140 of the body 1004 is spaced apart, for example uniformly spaced apart, from the glenoid surface when the peripheral members 1006 are properly seated at the rim or other portion of the glenoid, then sufficient soft tissue may have been removed. After the patient-specific guide 1000 is properly positioned, the guide 1000 may be used to place a guide pin through the channel 1012 and/or create an implant rotational alignment mark or place a periphery pin through the locating feature 1016.

As shown in FIG. 40A, the glenoid guide 1000 includes a receptacle 1032 extending from the body 1004. The receptacle 1032 may extend from the second side 124 the body 1004 at the outer periphery thereof. The receptacle 1032 is configured to receive a handle that may be used to stabilize the glenoid guide 1000 without the use of the guide pin.

Figure 41B:
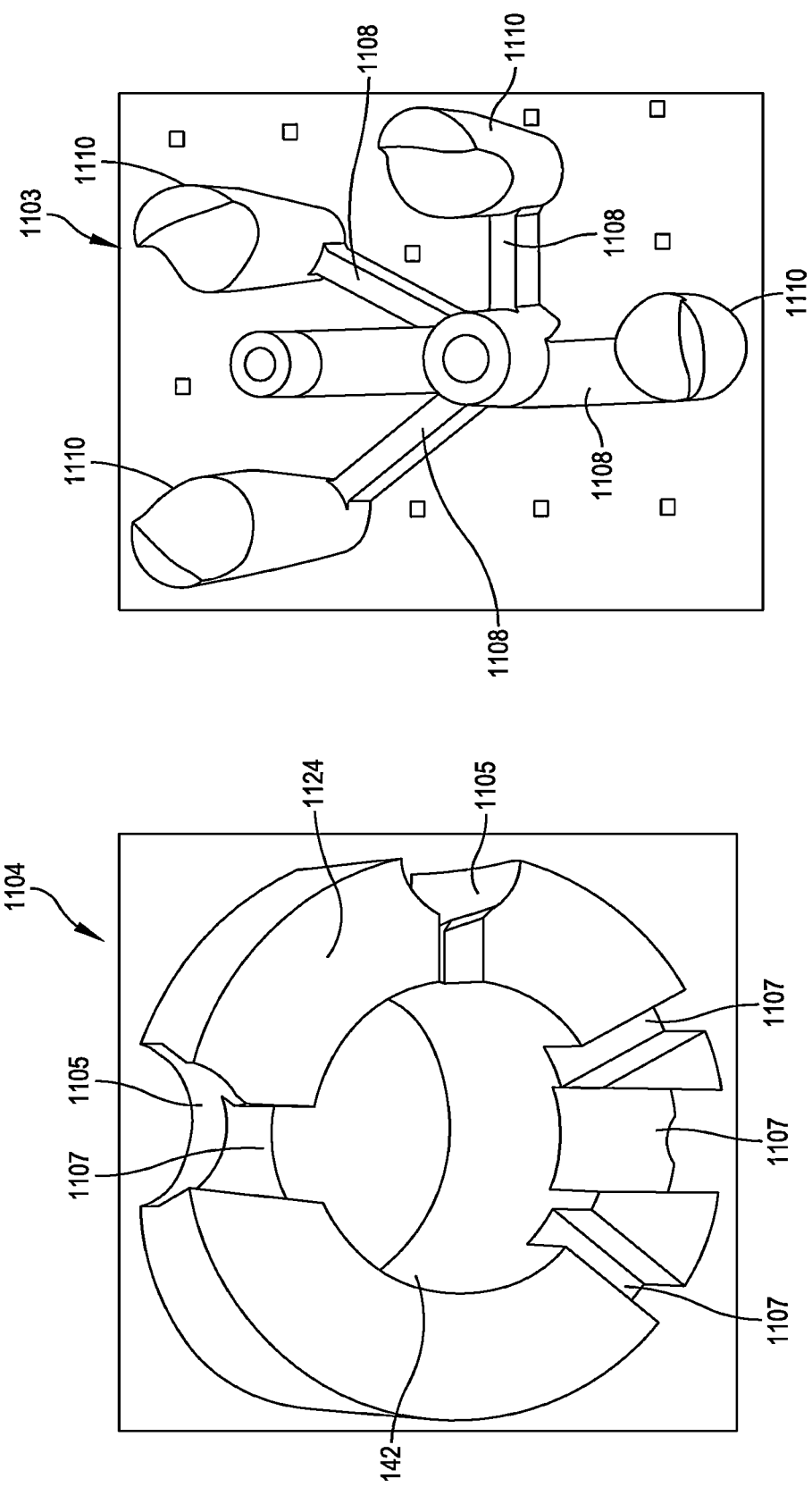

As described above, any of the glenoid guides described herein may be modular. As an illustrative embodiment, FIGS. 41A-41B show a modular guide 1100 including a body 1104 and a separate peripheral portion 1103. The peripheral portion 1103 may include any combination of peripheral members 1106 as is described above in connection with other guides. The body 1104 may be removably attached to the peripheral portion 1103, for example with a mechanical connection such as a friction fit, snap fit, threaded connection, or otherwise. The body 1104 may be designed to avoid obstructing the peripheral members 1106. For example, at least a portion or the entire outer periphery 144 may be disposed radially inward of the transverse portions 1110 of the peripheral members 1106. As shown in FIG. 41A, the body 1104 may include an outer periphery 144 structured to receive one or more of the peripheral members 1106. The body 1104 includes a number of concavities or cut outs 1105 structured to receive a corresponding peripheral member 1106, for example the transverse portion 1110 of the peripheral member 1106. The cut outs 1105 may have a concave shape or any other shape suitable for receiving the transverse portion 1110. As used herein a cut out can be an area where the otherwise continuous periphery 144 is interrupted, e.g., transitions from convex to concave, and does not necessarily connote that the concavity is made by removing a part of the body 1104 after it has been formed. The body 1104 may receive every peripheral member 1106 or only a subset of the peripheral members 1106, for example the body 1104 may only receive the transverse portions 1110 in a posterior or anterior region of the guide 1100. In the illustrated embodiment, the body 1104 receives a peripheral member 1106 at an inferior location (the member at 6 O'clock in FIG. 41B) and a peripheral member 1106 at an anterior location (the member at 3 O'clock in FIG. 41B. In many but not all cases, the body 1104 will be configured to receive peripheral members 1106 that are configured to contact inferior portions of the rim of a glenoid of a particular patient.

As shown in FIG. 41B, the body 1104 may include one or more slots 1107 to receive the elongate members 1108 of a corresponding peripheral member 1106. The one or more slots 1107 may be disposed on the second side 1124 of the body 1104 and extend part way through a thickness of the body 1104. The slots 1107 may extend radially from an outer periphery 144 of the body 1104 to an inner periphery 142 of the body 1104. The body 1104 may receive an elongate member 1108 in one of the slots 1107 without receiving a transverse portion 1110 of the same peripheral member 1106, for example, in a portion of the guide 1100 configured to mate with a superior aspect of the glenoid. The slots 1107 provide rotational alignment of the body 1104 with the peripheral portion 1103.

In use, one or both of the body 1104 and the peripheral portion 1103 may be patient specific. The body 1104 and the peripheral portion 1103 may be assembled together and the assembled guide may be used as described herein.

Methods of use of the patient-specific glenoid guides patient-specific glenoid guides 700, 800, 900, 1000, 1100 are explained in more detail below in Section III.

III. Method of Preparing a Glenoid Using Patient Matched Multi-Functional Glenoid Guides Methods of use of the patient-specific glenoid guide 100 will be discussed with reference to FIGS. 42A-42G. The use of other guides will be generally similar to the use of the patient-specific glenoid guide 100 except as discussed differently herein.

FIG. 42A illustrates the desired or target positions 1204, 1208, 1212, 1216 of the body 104, locating feature 108, K-wire guide channel 112, and/or peripheral channels 116 of the patient-specific glenoid guide 100, respectively. The target location 1204 can include the region of the glenoid that will receive and/or support a patient-specific glenoid guide, such as the patient-specific glenoid guide 100. In one embodiment, the size and shape of the target position 1204 can match the periphery size and shape of the baseplate 20 or another glenoid implant. The target position 1208 can correspond to the target location for a rotation control or locating feature. The target position 1212 can correspond to the position of a central anchor for the baseplate 20 or another glenoid implant. The target positions 1216 can correspond to locations or positions for peripheral anchors for the baseplate 20 or another implant.

The target positions 1204, 1208, 1212, and 1216 can be pre-operatively planned. Software can be used to select the target location 1204 of the body 104 and the position, size, and/or orientation of the channels of the component 100 relative to the glenoid. These predetermined locations, sizes, and/or orientations can be selected and/or modified by the user. The locating feature target position 1208, peripheral target positions 1216, and the central target position 1212 represent the predetermined locations of the glenoid that correspond to the channels and/or features of the patient-specific glenoid guide 100. The locating feature target position 1208 is located, e.g., centered on a location to be intersected by the axis of the locating feature 108 of the guide 100. The peripheral target positions 1216 are located, e.g., are centered on locations to be intersected by axes of the peripheral channels 116 of the guide 100. The central target position 1212 is located, e.g., centered on, a location to be intersected by the axis of the K-wire guide channel 112. The target positions 1204, 1208, 1212, 1216 can be displayed on a user interface of a surgical planning tool that can be superimposed on a rendering of the bone of the patient taken from imaging data, e.g., from a CT scan. The peripheral target positions 1216 identify the locations where recesses can be formed in the glenoid.

As an initial step, the glenoid of a patient is exposed. Cartilage, labrum, and/or osteophytes are optionally removed from the surface and/or rim of the glenoid.

Figures 42B, 42C:
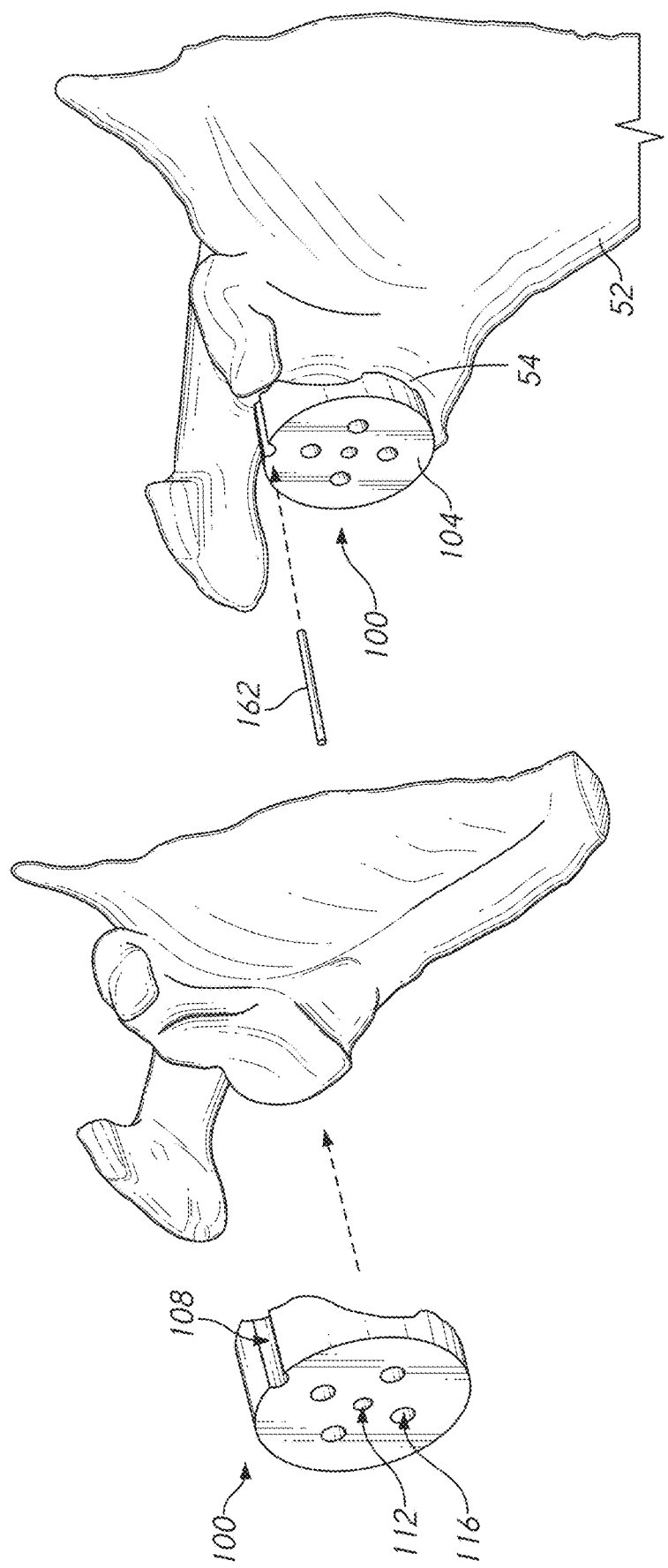
Figure 42F:
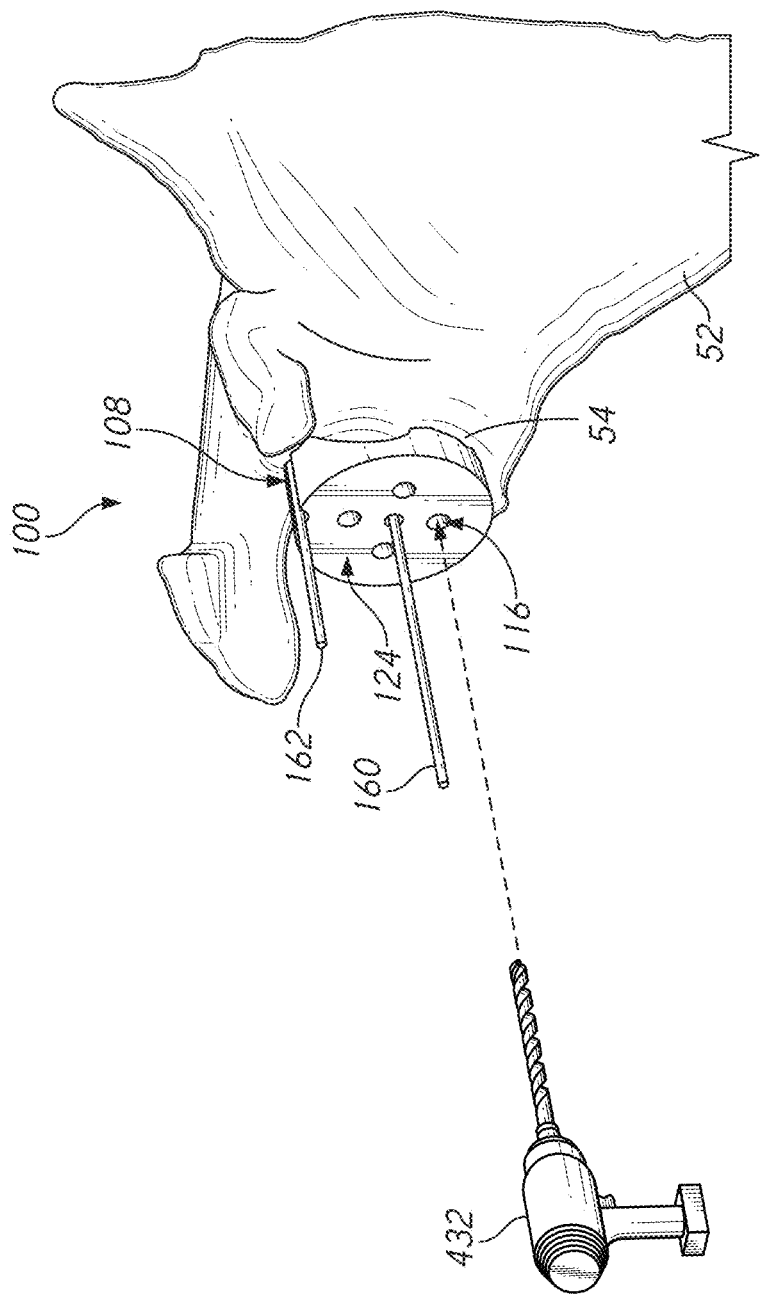

As shown by the dashed arrow in FIG. 42B, the patient-specific glenoid guide 100 is advanced towards the target position 1204 on the glenoid. The guide 100 is advanced until a first side 120 of the guide 100 is in contact with an articular surface of the glenoid. The guide 100 can be oriented in the planned orientation before applying the guide 100 to the glenoid. The guide 100 can also be applied to the glenoid and then re-oriented to obtain the planned orientation. The patient-specific glenoid guide 100 can be rotated as needed until the surgeon can confirm that the patient matched portion 140 is correctly positioned on top of the anatomy to which it is matched. In embodiments with outrigger projections (e.g., the glenoid guides 700, 800) the positioning and re-positioning can include mating the first (medial) side of the outrigger structure to any anatomy to which they are planned to mate. The guide 100 is rotated and/or translated until it aligns with a portion of the articular surface of the glenoid to which the patient matched surface of the first side 120 of the guide 100 has been configured as a negative.

As illustrated by the dashed arrow in FIG. 42C, the periphery pin 162 is optionally advanced towards the target position 1208 on the glenoid. The periphery pin 162 is brought into contact with the glenoid after placing the patient-specific glenoid guide 100 in contact with an articular surface of the glenoid. The periphery pin 162 can slide into engagement with the locating feature 108 of the guide 100.

In a first optional method excluding the periphery pin 162, a surgical pen is used to mark the scapula 52, e.g., a portion of the glenoid 54 or a portion of the scapula adjacent to the glenoid using the locating feature 108. Or, the patient-specific glenoid guide 300 can be used without marking any location. Optionally the patient-specific glenoid guide 300 has a line or other marking indicia on the periphery 304 that the surgeon can reference to mark the bone. Other guides without a channel-type locating features (e.g., the patient-specific glenoid guides 500, 550, 700, 800, 900, 1000) can include markings on their periphery for guiding a surgical pen to mark a portion of the scapula 52 to aid in placement of the baseplate 20.

The use of any of the guides described above that have enhance visibility portions (e.g., the guides 500, 550, 600, 700, 900, 1000) can include visualizing a portion of the glenoid 54 adjacent to a periphery of the guide. A surgical plan can include information about how much of the glenoid 54 should be visible between any portion of the periphery of the guides and a landmark of the scapula 52, e.g., the rim of the glenoid 54. If the guide is centered on the rim of the glenoid 54 an equal amount of the articular surface of the glenoid 54 should be visible (and in one method is viewed) between the anterior-inferior concavity of the guide and an anterior-inferior portion of the rim of the glenoid 54 and the posterior-inferior concavity of the guide and a posterior-inferior portion of the rim of the glenoid.

FIGS. 42D-E illustrate the central guide pin 160 being advanced through the K-wire guide channel 112 of the guide 100 and into contact with the glenoid at the central target position 1212 on the glenoid. As shown by the dashed arrow in FIG. 42D, the central guide pin 160 is inserted through the K-wire guide channel 112 when the guide 100 is held against the glenoid. Some guides provide structures for supporting the guide outside of a central area. For example, the patient-specific glenoid guide 700 has outriggers at the peripheral member 708 and at the peripheral member 732. These members can be placed on planned portions of the scapula 52, e.g., on or traversing the rim of the glenoid 54. The patient matched portion 140 can also be placed on the portion of the glenoid 54 to which it is configured to mate. Similarly one or all of the first peripheral member 806, the second peripheral member 814, the third peripheral member 816, and the fourth peripheral member 820 can be placed on the scapula 52 in pre-planned locations while the patient matched portion 140 of the patient-specific glenoid guide 800 is mated to the articular surface of the glenoid 54. The optional periphery pin 162, when used or present, remains in place for subsequent guiding of the baseplate 20 as discussed below as the central guide pin 160 is advanced through the K-wire guide channel 112. In some variations, the periphery pin 162 is placed later, because the periphery pin 162 may not be needed during the majority of the use of the patient-specific glenoid guide 100. Patient guides 900, 1000 also include a plurality of peripheral members that may be positioned in the manner described above. However, in some variations, when the peripheral members 906, 1006 are properly seated at the rim or other portion of the glenoid or scapula, the first side 120 of the body 904, 1004 may be spaced apart from the glenoid surface, for example by less than or equal to about 1.0 mm. If the patient matched portion 140 of the body 904, 1004 contacts the glenoid surface when the peripheral members 906, 1006 are properly seated at the rim or other portion of the glenoid, then additional soft tissue may need to be removed. If the patient matched portion 140 of the body 904, 1004 is spaced apart from the glenoid surface when the peripheral members 906, 1006 are properly seated at the rim or other portion of the glenoid, then sufficient soft tissue may have been removed.

The patient-specific glenoid guide 400 provides a convenient method for placing the central guide pin 160. In one method, the patient-specific glenoid guide 400 is coupled with the pin guide 416. The patient-specific glenoid guide 400 can first be placed against the glenoid 54 and the pin guide 416 can thereafter be mated to the guide channel 412 of the patient-specific glenoid guide 400. The docking feature 420 can be placed in a tapered portion of the guide channel 412 and can come to rest against the guide seat 442. Thereafter, the central guide pin 160 can be advanced into the open end of the lumen 424.

Instead of placing a central guide pin, the patient-specific glenoid guide may provide a method for drilling a central anchor hole. For example, as described above with respect to FIGS. 40A and 40B, the guide 1000 may include a central cannula that receives the drill for preparation of the central anchor hole.

Recesses can be formed in the glenoid using the patient-specific glenoid guide 100. The central guide pin 160 and the optional periphery pin 162, when present, help stabilize the guide 100 during the formation of recesses. A recess extending into the glenoid from the peripheral target position 1216 on the glenoid can be formed through the guide 100. For example, as illustrated by the dashed arrow in FIG. 42F, a drill 432 can be coupled with an appropriately sized drill bit that can be advanced through the peripheral channel 116 in the guide 100. The surgeon can advance a drill bit coupled with the drill 432 through at least one peripheral channel 116 of the patient-specific glenoid guide 100 and into the glenoid at the corresponding peripheral target location 1216, thereby creating a recess in the glenoid. The depth and orientation of the recess can be selected pre-operatively and controlled by the length of the drill bit coupled with the drill 432. The planned trajectory of the drill bit extends along an axis centered on the peripheral target location 1216 and centered on the third channel axis 242 through the third channel entrance 236 (see FIG. 7) of the body 104 of the guide 100. The recess can be configured to engage an anchor 24, such as a screw.

As discussed above, the third channel 235A of the patient-specific glenoid guide 400 can be mated with a tubular drill guide. The guide can be similar to the pin guide 416 but sized and configured for the third channel 235A. One or more of the first channel 218A, the second channel 227A, the third channel 235A, and the fourth channel 243A can be mated with a drill guide prior to forming the recesses at the target locations 1216.

A surgeon can drill recesses 1220 extending into the glenoid 54 from each of the peripheral target positions 1216 using the patient-specific glenoid guide 100 as a guide. An axis extends through the center of each of the recesses 1220 once the recesses are formed. The axis of each recess 1220 is aligned with the center of the corresponding peripheral channel 116 of the guide 100. Each recess 1220 formed in the glenoid can be similar to or dissimilar from each of the other recesses. One or more of the recesses can extend at a non-perpendicular angle to the second or lateral side 124 of the guide 100. Each recess 1220 can be configured to have different orientations, e.g., be at different non-perpendicular angles to the second side 124 of the guide 100. The recesses 1220 can have axes 1222 that are splayed as shown in FIG. 42G.

Figure 42G:
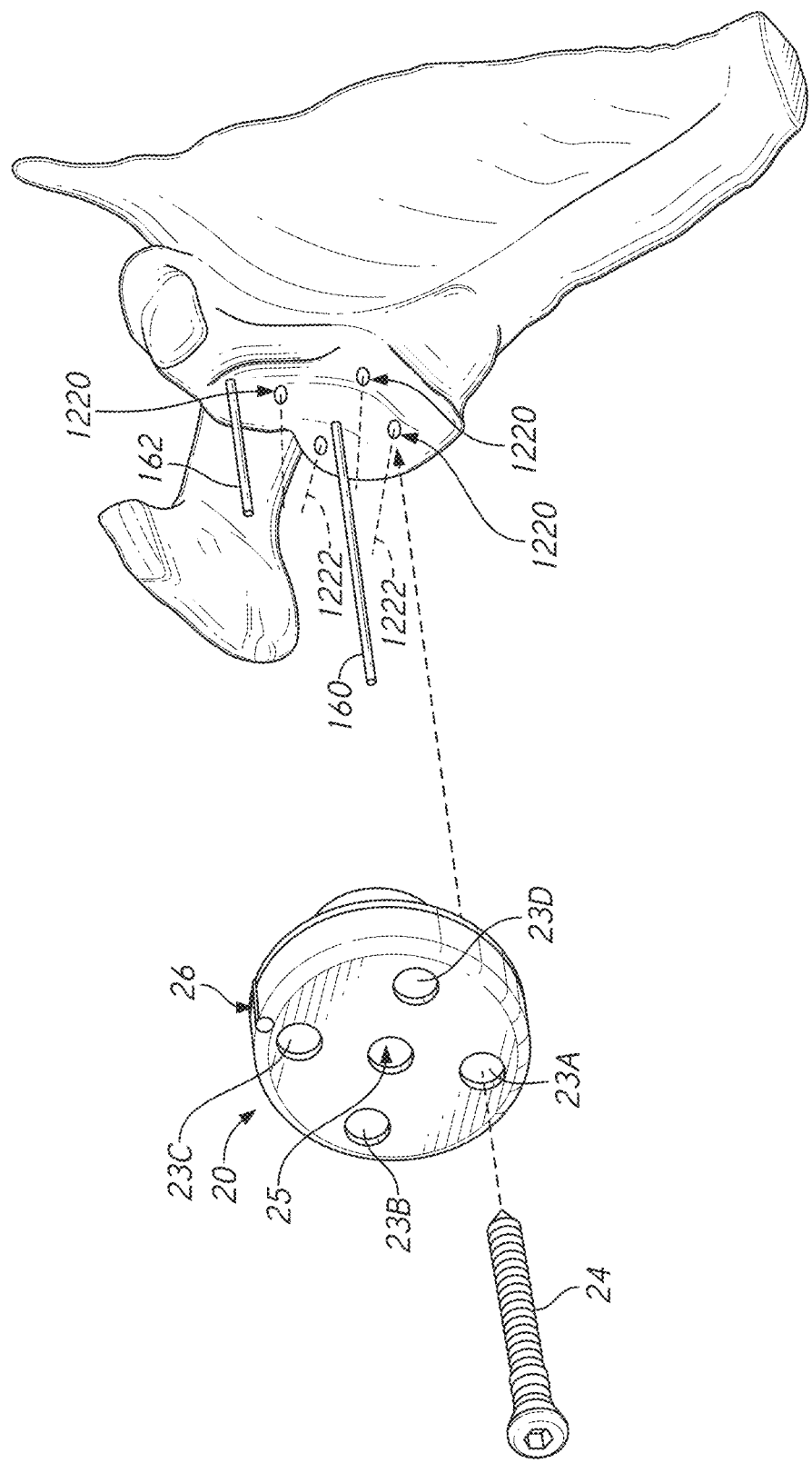

As illustrated in FIG. 42G, the peripheral recesses 1220 have been formed in the glenoid 54 using the guide 100. The guide 100 and the optional periphery pin 162 can be removed from the glenoid. The central guide pin 160 is maintained in contact with the glenoid. The central guide pin 160 guides the baseplate 20 into contact with the glenoid. The baseplate 20 can be oriented using a rotational alignment feature, such as a custom mark on the baseplate 20, or a separate guide. The baseplate 20 can have a mark 26 on the outer periphery thereof that can be rotated into alignment with the periphery pin 162, as shown, or can be oriented toward a bovie mark formed using the locating feature 108. The central channel 25 of the baseplate 20 slides over the central guide pin 160 when the baseplate is advanced towards the glenoid. Although the central channel appears much larger it could be smaller in size to closely match the size of the central guide pin 160 while being slideable thereof. In some cases a separate instrument is mated to the larger channel 25 of the baseplate which instrument can have an inner lumen sized to slide over the central guide pin 160. In some methods, the channel formed by the central guide pin 160 can provide a pilot hole for a central anchor of the glenoid assembly 19. The central anchor can be coupled with the glenoid 54 in a step between that illustrated in FIG. 37F and that illustrated in FIG. 37G. The central anchor can be advanced into the glenoid 54 and the baseplate 20 can be coupled therewith in a subsequent step. The coupling between the central anchor and the baseplate 20 can facilitated rotational orientation of the baseplate 20 to align the mark 26 to a bovie mark or other locating feature on or coupled with the scapula 52. Further details concerning the glenoid assembly 19 are discussed in U.S. Ser. No. 14/794,544, which is hereby incorporated by reference to supplement the discussion of the glenoid assembly 19 and for all other purposes. As shown by the dashed arrow in FIG. 42G, the surgeon can secure the baseplate 20 to the glenoid using anchors 24, such as screws, in a pre-operatively planned manner. The depth of the peripheral recess 1220 can be confirmed using a tool such as a depth gauge. The anchor 24 can be advanced through the peripheral channel 23 of the baseplate 20 and into the peripheral recess 1220 in the glenoid. An anchor 24 can be advanced through each of the peripheral recesses 1220 in the glenoid 54.

Terminology

Although certain embodiments have been described herein, the implants and methods described herein can interchangeably use any articular component, as the context may dictate.

As used herein, the relative terms "proximal" and "distal" shall be defined from the perspective of the implant. Thus, proximal refers to the direction of the articular component and distal refers to the direction of an anchor component, such as a stem of a humeral anchor or a thread or porous surface or other anchoring structure of a stemless anchor when the implant is assembled.

Conditional language, such as "can," "could," "might," or "may," unless specifically stated otherwise, or otherwise understood within the context as used, is generally intended to convey that certain embodiments include, while other embodiments do not include, certain features, elements, and/or steps. Thus, such conditional language is not generally intended to imply that features, elements, and/or steps are in any way required for one or more embodiments.

The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. In addition, the articles "a," "an," and "the" as used in this application and the appended claims are to be construed to mean "one or more" or "at least one" unless specified otherwise.

The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 1" includes "1." Phrases preceded by a term such as "substantially," "generally," and the like include the recited phrase and should be interpreted based on the circumstances (e.g., as much as reasonably possible under the circumstances). For example, "substantially spherical" includes "spherical." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y and at least one of Z to each be present.

Although certain embodiments and examples have been described herein, it should be emphasized that many variations and modifications may be made to the humeral head assembly shown and described in the present disclosure, the elements of which are to be understood as being differently combined and/or modified to form still further embodiments or acceptable examples. All such modifications and variations are intended to be included herein within the scope of this disclosure. A wide variety of designs and approaches are possible. No feature, structure, or step disclosed herein is essential or indispensable.

Some embodiments have been described in connection with the accompanying drawings. However, it should be understood that the figures are not drawn to scale. Distances, angles, etc. are merely illustrative and do not necessarily bear an exact relationship to actual dimensions and layout of the devices illustrated. Components can be added, removed, and/or rearranged. Further, the disclosure herein of any particular feature, aspect, method, property, characteristic, quality, attribute, element, or the like in connection with various embodiments can be used in all other embodiments set forth herein. Additionally, it will be recognized that any methods described herein may be practiced using any device suitable for performing the recited steps.

For purposes of this disclosure, certain aspects, advantages, and novel features are described herein. It is to be understood that not necessarily all such advantages may be achieved in accordance with any particular embodiment. Thus, for example, those skilled in the art will recognize that the disclosure may be embodied or carried out in a manner that achieves one advantage or a group of advantages as taught herein without necessarily achieving other advantages as may be taught or suggested herein.

Moreover, while illustrative embodiments have been described herein, it will be understood by those skilled in the art that the scope of the inventions extends beyond the specifically disclosed embodiments to any and all embodiments having equivalent elements, modifications, omissions, combinations or sub-combinations of the specific features and aspects of the embodiments (e.g., of aspects across various embodiments), adaptations and/or alterations, and uses of the inventions as would be appreciated by those in the art based on the present disclosure. The limitations in the claims are to be interpreted broadly based on the language employed in the claims and not limited to the examples described in the present specification or during the prosecution of the application, which examples are to be construed as non-exclusive. Further, the actions of the disclosed processes and methods may be modified in any manner, including by reordering actions and/or inserting additional actions and/or deleting actions. It is intended, therefore, that the specification and examples be considered as illustrative only, with a true scope and spirit being indicated by the claims and their full scope of equivalents.

Any methods disclosed herein need not be performed in the order recited. The methods disclosed herein include certain actions taken by a practitioner; however, they can also include any third-party instruction of those actions, either expressly or by implication. For example, actions such as "coupling a glenoid guide with the glenoid rim" include "instructing coupling of a glenoid guide with a glenoid rim."

What is claimed is:

1. A method comprising:
   exposing a glenoid of a patient;
   removing soft tissue from a surface of the glenoid;
   advancing a body of a glenoid guide toward the glenoid, the body of the glenoid guide comprising a lateral surface and a medial surface, the medial surface comprising a patient matched portion being configured as a negative surface of a glenoid portion of a scapula of a specific patient, the glenoid guide further comprising a plurality of peripheral members extending radially outward from an outer periphery of the body, each of the plurality of peripheral members comprising a contact member; and a channel extending through the body from a channel entrance on the lateral surface to a channel exit on the medial surface and adapted to receive a pin guide,
   wherein the channel is tapered to form a temporary interference fit connection with the pin guide, and
   wherein the medial surface of the body is configured to be spaced apart from the glenoid portion when each contact member contacts a rim of the glenoid portion;
   contacting a patient matched contact member of each of the plurality of peripheral members with a rim of the glenoid to which the patient matched contact member has been configured to conform;
   advancing a drill along a planned trajectory defined by an axis of a bone preparation channel defined through the body of the glenoid guide;
   forming an anchor channel in a scapula along the axis; and
   securing an implant component to the scapula by advancing the implant or a bone screw into the anchor channel.

2. The method of claim 1, further comprising assessing whether the patient matched portion of the medial surface contacts the surface of the glenoid portion.

3. The method of claim 2, wherein if the patient matched portion of the medial surface contacts the surface of the glenoid, removing additional soft tissue until the medial surface of the glenoid guide is spaced apart from the surface of the glenoid portion.

4. The method of claim 1, further comprising advancing the drill directly through the bone preparation channel defined through the body.

5. The method of claim 1, further comprising advancing the drill until the drill contacts a drill stop disposed in the body of the glenoid guide.

6. The method of claim 1, further comprising providing a locator on or in the scapula to orient the glenoid guide relative to the glenoid.

7. The method of claim 1, further comprising stabilizing the glenoid guide using a handle.

8. The method of claim 1, further comprising engaging a bushing with the guide to provide a guidewire guide channel to place a guide wire.

* * * * *